US009828633B1

(12) United States Patent
Etienne et al.

(10) Patent No.: US 9,828,633 B1
(45) Date of Patent: *Nov. 28, 2017

(54) MODIFIED NUCLEOTIDES METHODS AND KITS

(71) Applicant: Pierce Biotechnology, Inc., Rockford, IL (US)

(72) Inventors: Christopher L. Etienne, Fitchburg, WI (US); Kay K. Opperman, Rockton, IL (US); Barbara J. Kaboord, Oregon, WI (US); Scott D. Meier, Rockford, IL (US); Jean-Samuel Schultz, Rockford, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/883,810

(22) Filed: Oct. 15, 2015

Related U.S. Application Data

(60) Division of application No. 13/482,927, filed on May 29, 2012, now Pat. No. 9,206,216, which is a continuation-in-part of application No. 13/090,729, filed on Apr. 20, 2011, now Pat. No. 8,536,323.

(60) Provisional application No. 61/326,450, filed on Apr. 21, 2010.

(51) Int. Cl.
*C07H 19/20* (2006.01)
*C07H 19/10* (2006.01)
*C12Q 1/68* (2006.01)
*C12P 19/34* (2006.01)

(52) U.S. Cl.
CPC ........... *C12Q 1/6876* (2013.01); *C07H 19/10* (2013.01); *C07H 19/20* (2013.01); *C12P 19/34* (2013.01); *C12Y 605/01001* (2013.01); *C12Y 605/01002* (2013.01); *C12Y 605/01003* (2013.01)

(58) Field of Classification Search
None
See application file for complete search history.

(56) References Cited

U.S. PATENT DOCUMENTS

| | | |
|---|---|---|
| 4,914,210 A | 4/1990 | Levenson et al. |
| 5,047,519 A | 9/1991 | Hobbs, Jr. et al. |
| 5,151,507 A | 9/1992 | Hobbs, Jr. et al. |
| 5,247,081 A | 9/1993 | Edge |
| 5,558,991 A | 9/1996 | Trainor |
| 5,567,811 A | 10/1996 | Misiura et al. |
| 5,608,063 A | 3/1997 | Hobbs, Jr. et al. |
| 5,684,142 A | 11/1997 | Mishra et al. |
| 5,888,819 A | 3/1999 | Goelet et al. |
| 5,952,174 A | 9/1999 | Nikiforov et al. |
| 6,004,744 A | 12/1999 | Goelet et al. |
| 6,013,431 A | 1/2000 | Soderlund et al. |
| 6,114,350 A | 9/2000 | Randall et al. |
| 6,197,956 B1 | 3/2001 | Randall et al. |
| 6,204,389 B1 | 3/2001 | Randall et al. |
| 6,224,644 B1 | 5/2001 | Randall et al. |
| 7,361,465 B2 | 4/2008 | Murphy et al. |
| 7,491,818 B2 | 2/2009 | McGall et al. |
| 7,504,215 B2 | 3/2009 | Cole et al. |
| 7,524,942 B2 | 4/2009 | Wang et al. |
| 7,541,144 B2 | 6/2009 | Wang |
| 7,572,585 B2 | 8/2009 | Wang |
| 8,536,323 B2 * | 9/2013 | Opperman ............. C07H 19/10 536/26.3 |
| 9,206,216 B2 * | 12/2015 | Etienne .................. C07H 19/10 |
| 2003/0165849 A1 | 9/2003 | Zhang et al. |
| 2008/0045418 A1 | 2/2008 | Xia |
| 2009/0176732 A1 | 7/2009 | Beigelman et al. |
| 2009/0286753 A1 | 11/2009 | Kauppinen et al. |

FOREIGN PATENT DOCUMENTS

WO    2004052907    6/2004

OTHER PUBLICATIONS

United Kingdom Search Report, GB1106948.1, dated Jul. 28, 2011, 3 pages.
Extended European Search Report, EP 12187509.0, dated Jun. 4, 2013 (8 pages).
Barone et al. Novel Nucleoside Triphosphate Analogs for the Enzymatic Labeling of Nucleic Acids in *Nucleosides, Nucleotides & Nucleic Acids*, 20(4-7), 1141-1145 (2001).
Hall-Pogar, et al. Specific *trans*-acting proteins interact with auxiliary RNA polyadenylation elements in the COX-2 3'-UTR. *RNA* (2007), 13:1103-1115, Cold Spring Harbor Laboratory Press.
O'Connor, et al. Two Purified Domains of Telomerase Reverse Transcriptase Reconstitute Sequence-specific Interactions with RNA. *The Journal of Biological Chemistry*, vol. 280, No. 17, Apr. 29, pp. 17533-17539, 2005.
Ueda, C.T. and Roberts, R.W. Analysis of a long-range interaction between conserved domains of human telomerase RNA. *RNA* 2004 10: 139-147, pp. 139-147.
Leibold, E.A. and Munro, H.N. Cytoplasmic protein binds in vitro to a highly conserved sequence in the 5' untranslated region of ferritin heavy- and light-subunit mRNAs. *Cell Biology*, vol. 85, pp. 2171-2175, Apr. 1988.
Piskounova, et al. Determinants of MicroRNA Processing Inhibition by the Developmentally Regulated RNA-binding Protein Lin28. *Journal of Biological Chemistry*, vol. 283 No. 31 pp. 21310-21314, Aug. 1, 2008.
McKinley, B.A. and Sukhodolets, M.V. *Escherichia coli* RNA polymerase-associated SWI/SNF protein RapA: evidence for RNA-directed binding and remodeling activity. *Nucleic Acids Research*, 2007, vol. 35, No. 21, pp. 7044-7060, Oct. 2, 2007.
Sukhodolets, M.V. and Ding, J.J. RapA, A Novel RNA Polymerase-Associated Protein, Is a Bacterial Homolog of SWI2/SNF2. *The Journal of Biological Chemistry*, vol. 273, No. 12, pp. 7018-7023, Mar. 20, 1998.

(Continued)

*Primary Examiner* — Eric S Olson
(74) *Attorney, Agent, or Firm* — McNeill Baur PLLC

(57) ABSTRACT

Modified nucleotides, and methods to modify nucleotides with a moiety or label, such as biotin, that permits their detection and results in a modified nucleotide, and methods of use of the modified nucleotide in quantitative and qualitative assays.

23 Claims, 16 Drawing Sheets

(56) References Cited

OTHER PUBLICATIONS

England, T.E., et al. Dinucleoside pyrophosphates are substrates for T4-induced RNA ligase. *Proc. Natl. Acad. Sci. USA, Biochemistry*, vol. 74, No. 11, pp. 4839-4842, Nov. 1977.

Hinton, D.M., et al. The preparative synthesis of oligodeoxyribonucleotides using RNA ligase. *Nucleic Acids Research*, vol. 10, No. 6, pp. 18771894, 1982.

Romaniuk, E., et al. The Effect of Acceptor Oligoribonucleotide Sequence on the $T_4$ RNA Ligase Reaction. *Eur. J. Biochem*, 125, 639-643 (1982).

Richardson, Ross W. and Gumport, Richard I. Biotin and fluorescent labeling of RNA using T4 RNA ligase. *Nucleic Acids Research*, vol. 11, No. 18, pp. 6167-6184, 1983.

Walker, G.C., et al. T4-Induced RNA Ligase Joins Single-Stranded Oligoribonucleotides. *Proc. Nat. Acad. Sci. USA*, vol. 72, No. 1, pp. 122-126, Jan. 1975.

Brennan, Catherine A. and Gumport, Richard I. T4 RNA ligase catalyzed synthesis of base analogue-containing oligodeoxyribonucleotides and a characterization of their thermal stabilities. *Nucleic Acids Research*, vol. 13, No. 24, pp. 8665-8684, 1985.

England, TE, Bruce, AG, and OC Uhlenbeck. Specific labeling of 3' termini of RNA with T4 RNA ligase (1980) *Methods Enzym.* 65: 65-74.

G Keith. Optimization of conditions for labeling the 3' OH end of tRNA using T4 RNA ligase. (1983) *Biochimie* 65: 367-70.

Romaniuk, E. et al., Joining of RNA molecules with RNA ligase (1983) Methods Enzym 100: 52-59.

Hobbs, F. W. Jr. Palladium-Catalyzed Synthesis of Alkynylamino Nucleosides. A Universal Linker for Nucleic Acids. (1989) J. Org. Chem 54(14): 3420-3422.

Lee, S.E. et al., Enhancing the catalytic repertoire of nucleic acids: a systematic study of length and rigidity (2001) Nucleic Acids Res. 29(7): 1565-1573.

Langer, P. R. et al., Enzymatic synthesis of biotin-labelled polynucleotides: novel nucleic acid affinity probes. (1981) PNAS 78(11): 6633-6637.

Cole, K. et al., Direct labeling of RNA with multiple biotins allows sensitive expression profiling of acute leukemia class predictor genes (2004) Nucleic Acids Res 32(11); e86.

Park, K. D., Liu, R., and H. Kohn. Useful tools for biomolecule isolation, detection, and identification: acylhydrazone-based cleavable linkers. (2009) Chemistry & Biology 16: 763-772.

Shigdel, U. K., and Zhang, J., and C. He. Diazirine-based DNA photo-cross-linking probes for the study of protein-DNA interactions (2008) Angew. Chem. Int. 47: 90-93.

Costas, C., Yuriev, E., Meyer, K.L., Guion, T.S., and M.M. Hanna. RNA-protein crosslinking to AMP residues at internal positions in RNA with a new photocrosslinking ATP analog (2000) Nucl. Acids. Res. 28: 1849-1858.

Liu, D., and L. Sun. Direct isolation of specific RNA-interacting proteins using a novel affinity medium. (2005) Nucl. Acids Res. 33: 1-5.

Bachler, M., Schroeder, R., and U.W. Ahsen. StreptoTag: A novel method for the isolation of RNA-binding proteins. (1999). RNA 5: 1509-1516.

Khanam, T, et. al. (2006) Poly(A)-Binding Protein Binds to A-Rich Sequences via RNA Binding Domains 1+2 and 3+4. RNA Biology. 3: 170-177.

Rimmele, M.E., and J.G. Belasco. (1998) Target discrimination by RNA binding proteins: role of the ancillary protein U2A' and a critical leucine residue in differentiating the RNA-binding specificity of spliceosomal proteins U1A and U2B. RNA. 4: 1386-1396.

RiboTrap Kit, MBL International Corporation, available at http://www.mblintl.com/product/rn1011-rn1012 Code No. RN1011/RN1012, copyright 2010.

(D4) Hanna et al. Synthesis and characterization of a new photocrosslinking CTP analog and its use in photoaffinity labeling *E.coli* and T7 RNA polymerases. Nucleic Acids Research, vol. 21, No. 9 (1993), pp. 2073-2079.

\* cited by examiner

Preparation of Biotin-PEG₄-Alkane-3′, 5′-Cytidine Bisphosphate

Synthesis of Biotin-Linker-Alkyne-3′, 5′-Cytidine Bisphosphate

Synthesis of Biotin Linker-Alkene-3´, 5´-Cytidine Bisphosphate

A.      B.      C.

Nucleotide Alkene Linkage Reactivity in Cell Extract

3',5'-Bisphosphorylated Cytidine-Alkene-LC-Biotin

Functionality of Biotin-PEG₄-Alkane-3´, 5´-Cytidine Bisphosphate

IB: Anti-HA

MODIFIED NUCLEOTIDES METHODS AND KITS

This application is a Continuation of co-pending U.S. application Ser. No. 13/482,927 filed May 29, 2012, which is a Continuation-In-Part of U.S. application Ser. No. 13/090,729 filed Apr. 20, 2011 now U.S. Pat. No. 8,536,323; which claims priority from U.S. Provisional application Ser. No. 61/326,450 filed Apr. 21, 2010, each of which is expressly incorporated by reference herein in its entirety.

Modified nucleotides, methods to modify nucleotides with a moiety or label, such as biotin, that permit their detection and result in a modified nucleotide, methods of use of the modified nucleotide in quantitative and qualitative assays, and methods of synthesizing the disclosed modified nucleotides.

The modified nucleotides have the structure P1-P2-Nus-Alk-Lnk-Obs, and include a salt, conjugate base, tautomer, or ionized form, where P1 is a phosphate group; P2 is a phosphate group; Nus is a nucleoside moiety comprising a sugar bound to a purine or pyrimidine base; Alk is a connecting group having the structure -//—$(CH_2)_m$—Y—//- where Y is a bond or bond forming group selected from

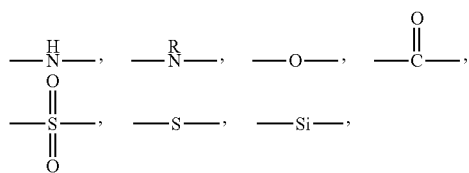

and m is an integer ranging from 3 to 6 inclusive, and where the leftmost bond is to Nus and the rightmost bond is to Lnk; Lnk is a linking group having the structure

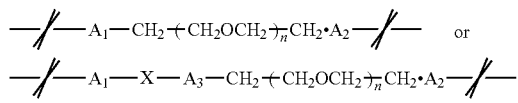

where n is an integer ranging from 2 to 48 inclusive; $A_1$ is a bond forming group selected from

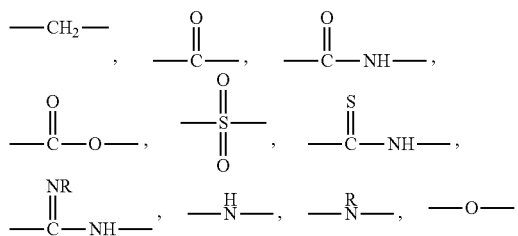

$A_2$ is a bond forming group selected from

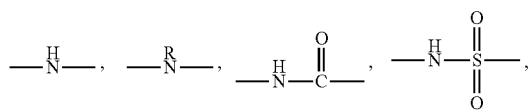

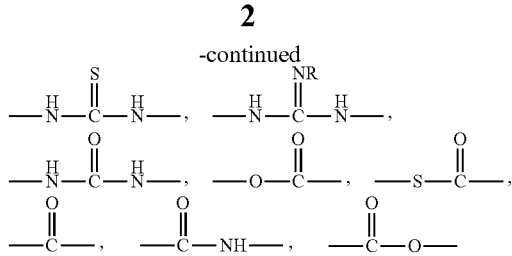

$A_3$, when present, is a bond forming group selected from

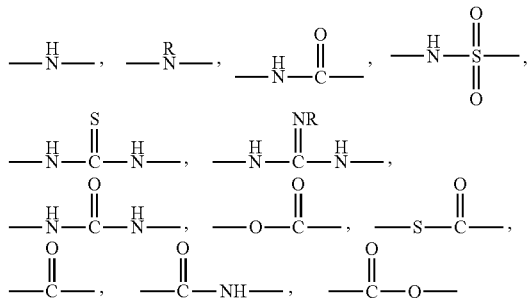

X is a cleavable group that can undergo silicon-carbon cleavage, nucleophilic cleavage, redox cleavage, photochemical cleavage, enzymatic cleavage, or exchange-based cleavage, and the leftmost bond is to Alk and the rightmost bond is to Obs; and Obs is an observable label moiety.

Such modified nucleotides, also termed nucleotide analogs, retain biological activity. For example, they are substrates for a variety of DNA and/or RNA polymerases. The modified nucleotide is added to an oligonucleotide or nucleic acid by routine methods, e.g., nick translation, random priming, polymerase chain reaction (PCR), 3'-end labeling, transcribing RNA using SP6, T3, or T7 RNA polymerases, etc.

Modified nucleotides may be used to form labeled probes that may be used in, e.g., biological screening, diagnosis, etc. As one example, screening an array permits different constituents of a complex sample to be determined. For example, an oligonucleotide probe containing a biotinylated nucleotide specifically binds to analytes in the sample that contain a complementary sequence, yielding an observable binding pattern detectable upon interrogating the array. As another example, an oligonucleotide probe containing a biotinylated nucleotide can be used to investigate small ribonucleic acids (RNAs) such as microRNAs (miRNAs), and their functional interactions with other RNA molecules or cellular proteins.

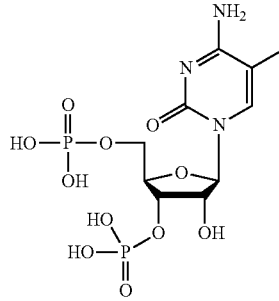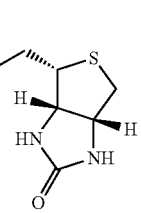

Figure 10:
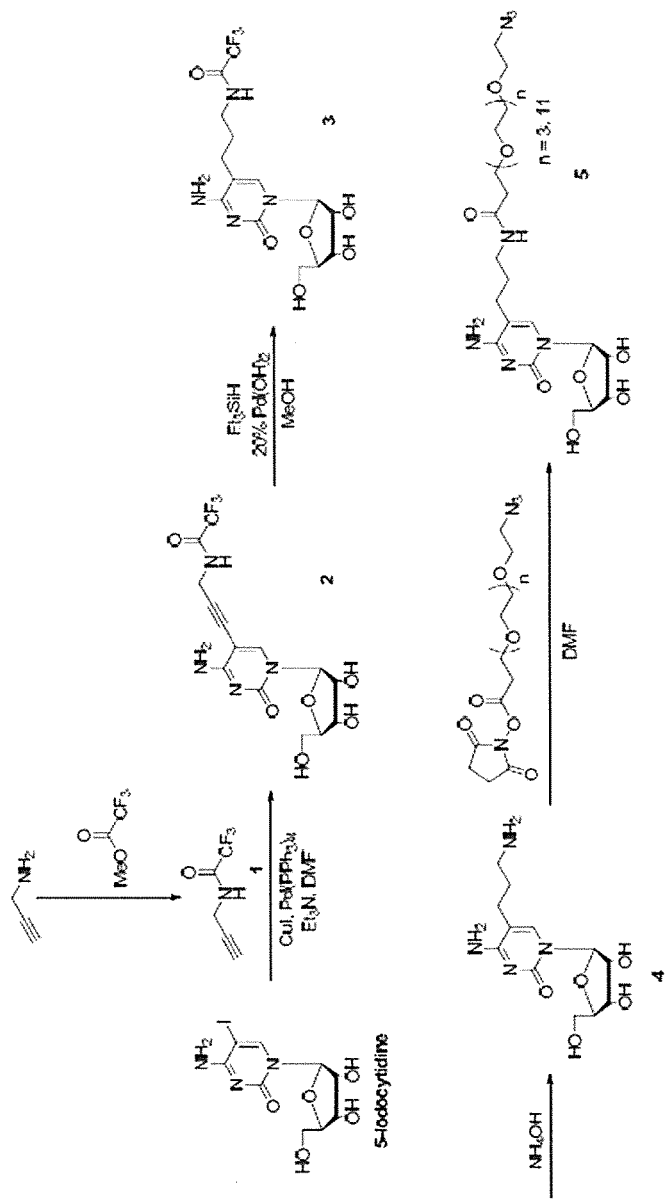

FIG. 10 shows synthesis of azide-(poly)ethylene glycol $(PEG)_{(n)}$-alkane cytidine intermediate.

Figure 11:
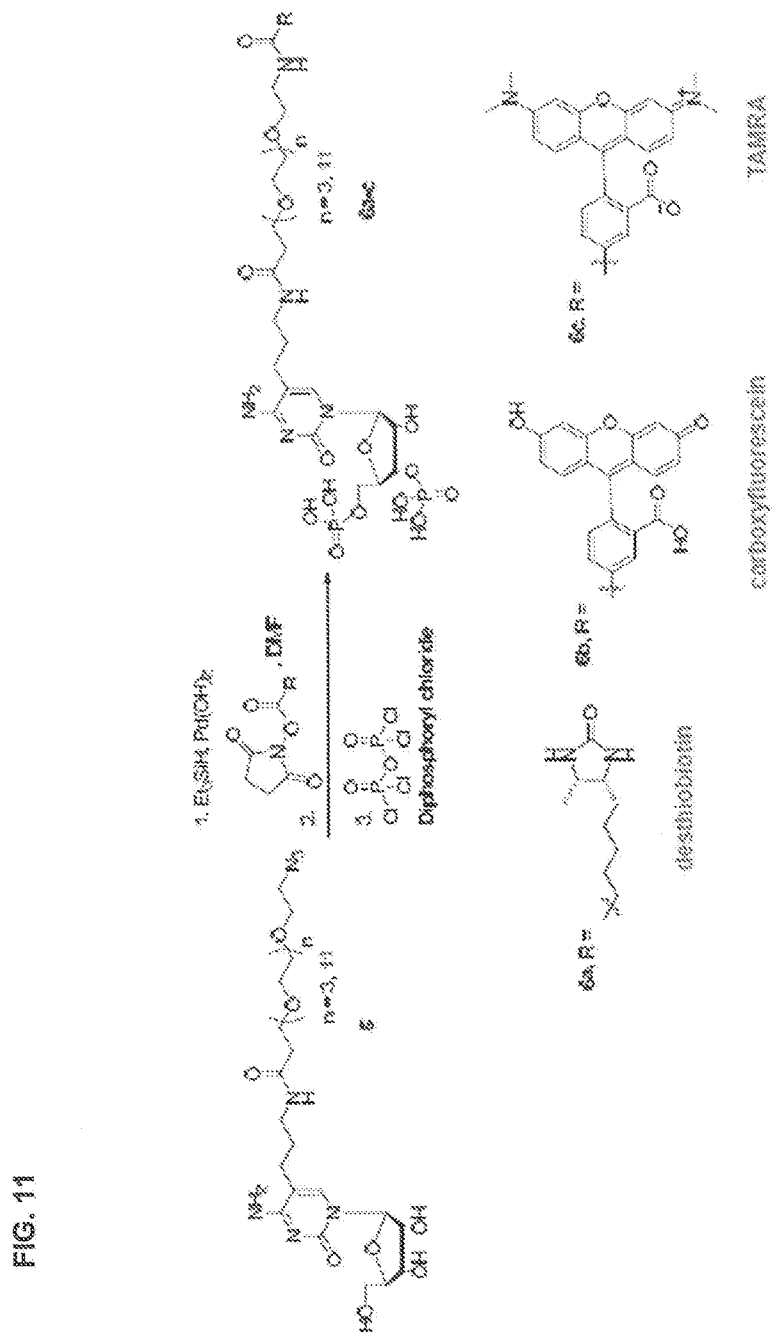

FIG. 11 shows synthesis of R-$PEG_{(n)}$-alkane-3'5'-bisphosphate cytidine.

Figure 12:
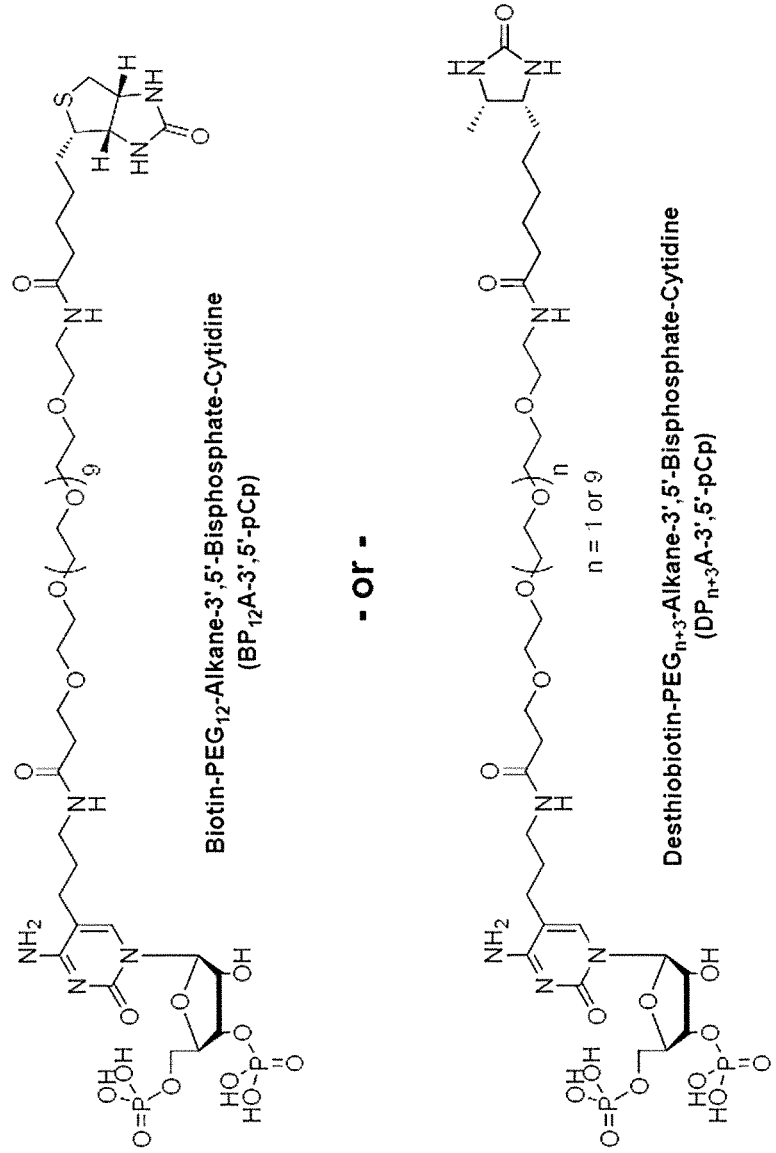

FIG. 12 shows two RNA pull-down labeling reagents.

Figure 13:
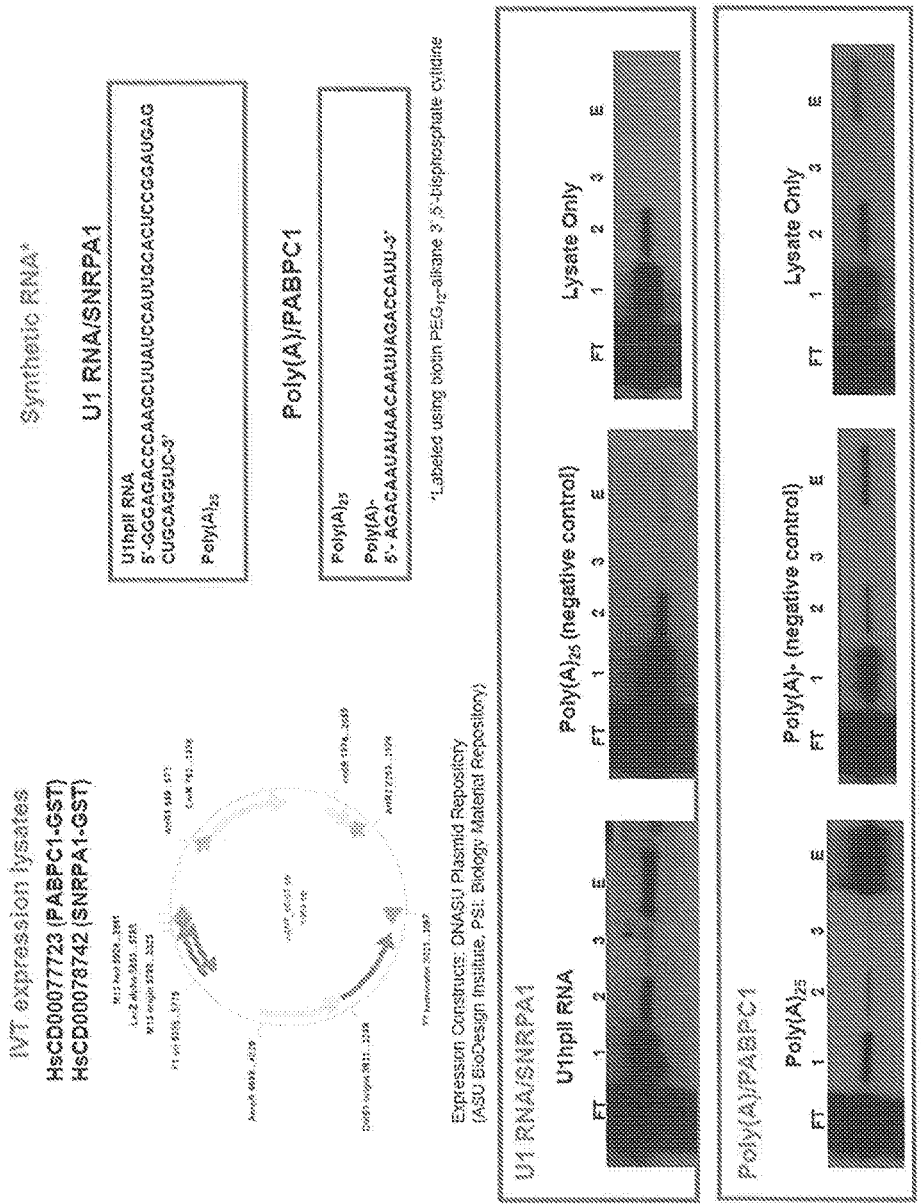

FIG. 13 shows RNA binding protein enrichment using overexpression lysate.

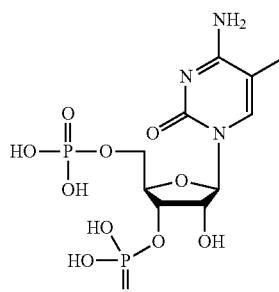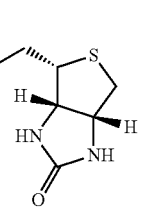

Figure 14:
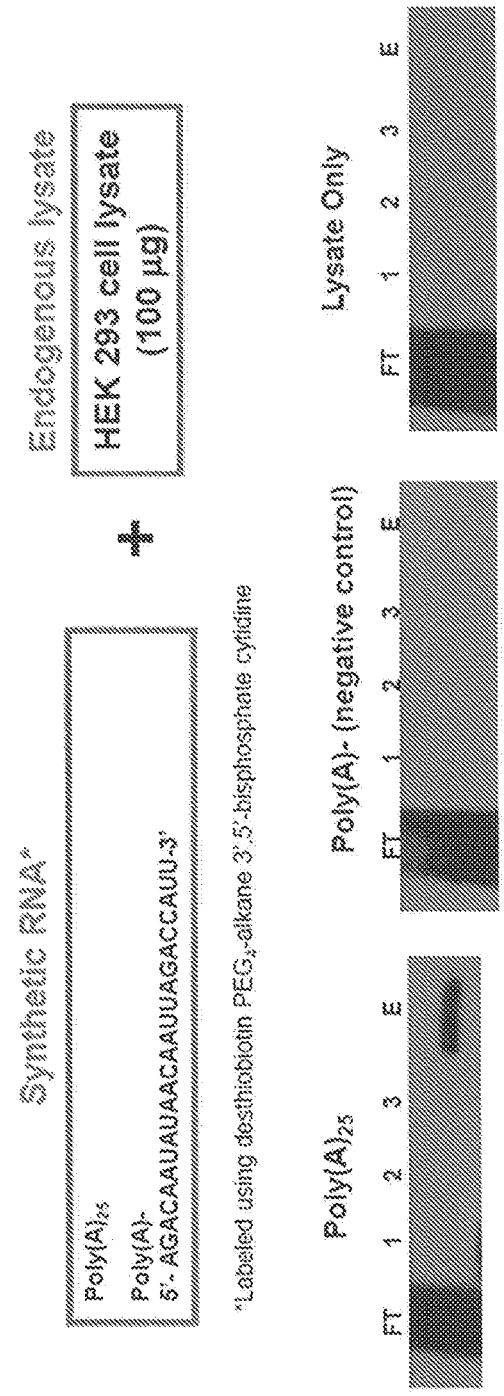

FIG. 14 shows RNA binding protein enrichment using cell lysate.

Figure 15:
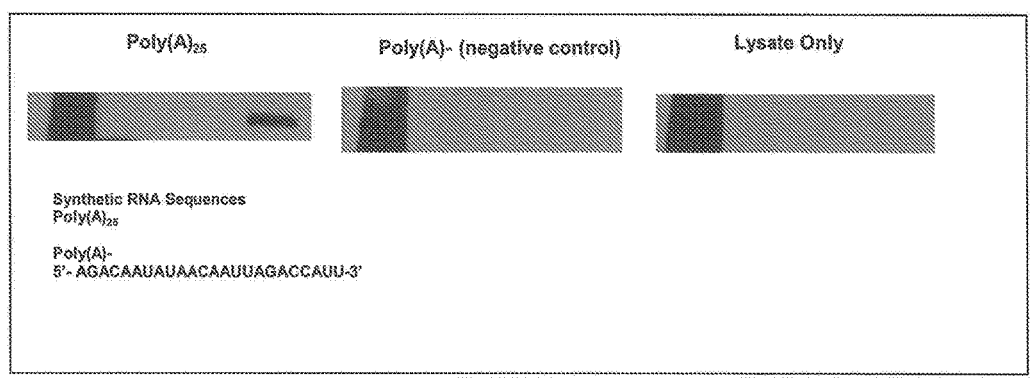

FIG. 15 shows RNA binding protein enrichment using endogenous lysate and desthiobiotin-$PEG_4$-alkane-3'5'-bisphosphate cytidine.

Figure 16:
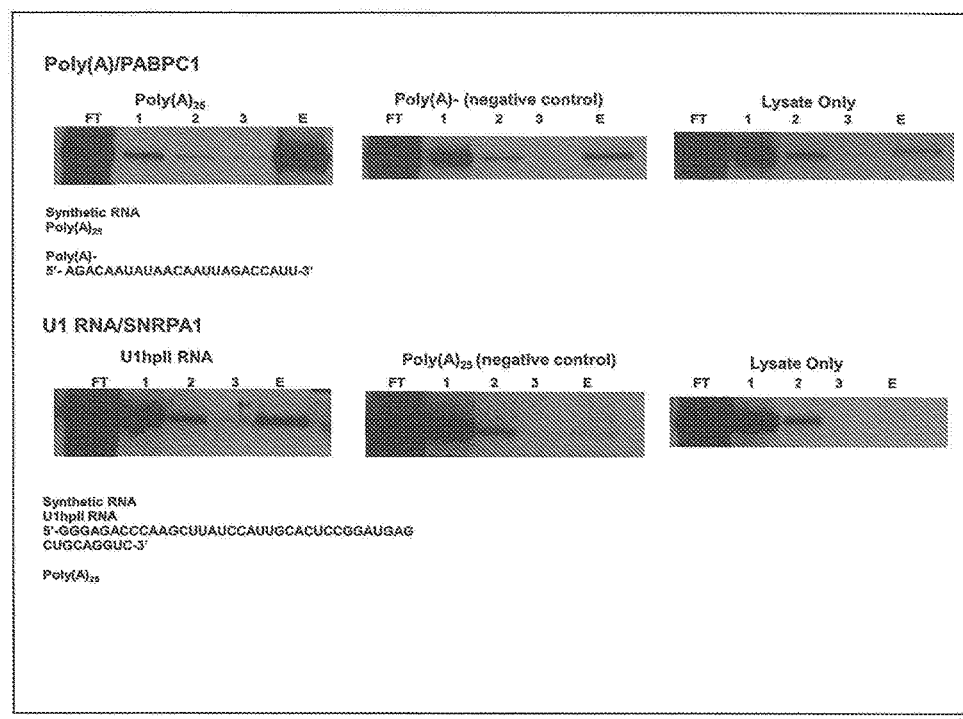

FIG. 16 shows RNA binding protein enrichment using overexpression lysate and biotin-$PEG_{12}$-alkane-3'5'-bisphosphate cytidine.

Figure 17:
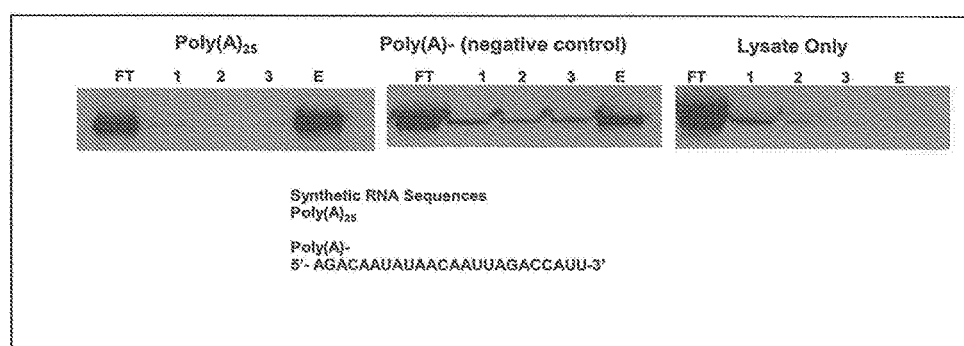

FIG. 17 shows RNA binding protein enrichment using crosslinking and biotin-$PEG_{12}$-alkane-3'5'-bisphosphate cytidine.

As subsequently disclosed, the nucleotide can be modified by adding at least one of the following substituents that function as detector molecules, either directly or indirectly: biotin and derivatives, azide, alkyne, aldehyde, diene, amine, disulfide, fluorophore, spin label, polyethyleneglycol (PEG). These substituents are added in various permutations, specific entities, and chain lengths.

In one embodiment, the modified nucleotide is a biotinylated nucleotide having the formula biotin-polyethylene glycol (PEG)-alkane-nucleotide with PEG having at least 7 carbon atoms and up to 100 carbon atoms. For any of the disclosed inventive compounds, the compound includes the salt form, conjugate base, tautomer, and/or ionized form. In one embodiment, the modified nucleotide is a ribonucleotide. In one embodiment, the ribonucleotide can be, but is not limited to, cytidine.

In one embodiment, the biotinylated nucleotide is a cytidine 3'-5'-bisphosphate having a $PEG_4$ linker with the structure shown below.

This structure had enhanced ligation efficiency over prior art biotinylated compounds due to the presence of the alkane adjacent to cytidine.

One embodiment is a method for labeling an RNA probe with a biotinylated nucleotide having the structure under conditions that label the RNA probe. The modified ribonucleotide is incubated with an enzyme capable of ligating the biotinylated ribonucleotide to the RNA probe (e.g., a ligase such as T4 ligase), to result in a biotin-labeled RNA probe. In one embodiment, single stranded T4 ligase is used. In one embodiment, double stranded T4 ligase is used. In one embodiment, thermostable T4 ligase is used. Examples of suitable ligases include T4 RNA Ligase 1 (applications include labeling of 3'-termini of RNA with 5'-[$^{32}$P] pCp, inter- and intramolecular joining of RNA and DNA molecules; synthesis of single-stranded oligodeoxyribonucleotides; and incorporation of unnatural amino acids into proteins); T4 RNA Ligase 2 (applications include ligating a nick in dsRNA, splintered RNA ligation, and ligating the 3' OH of RNA to the 5' phosphate of DNA in a double stranded structure); T4 RNA Ligase 2, truncated (applications include joining a single stranded adenylated primer to RNAs for cloning, and small RNA cloning); T4 RNA Ligase 2, truncated K227Q (applications include joining a single stranded adenylated primer to RNAs for cloning, small RNA cloning, and ligating with the lowest possible ligation byproduct); each of which is commercially available from New England BioLab; and thermostable RNA ligase, which is able to perform ligations at elevated temperatures, such as above about 40°, commercially available from Epicentre. In one embodiment, the modified nucleotide is purified prior to ligation. Subsequent assaying for the biotinylated probe permits detection of the presence, quantity, etc. of the ribonucleotide in the sample. The method is used with, e.g., and without limitation, mobility shift assays, Northern blots, in situ hybridization, etc. Biotin-labeled RNA probe can be detected using a streptavidin-conjugated reporter molecule such as, e.g. and without limitation, enzymes (e.g., peroxidases), fluorescent dyes, etc.

One embodiment is a method of synthesizing biotin-PEG-4-alkane-3',5'-cytidine-bisphosphate.

One embodiment is a kit containing a compound having the structure

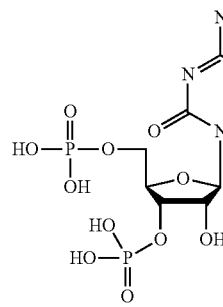

and instructions for labeling a nucleic acid using the compound. The kit can also contain an enzyme, a control RNA (either labeled or unlabeled with the modified nucleotide), and buffer.

The modified nucleotide has enhanced ligation efficiency over known compounds due to the presence of an alkane linkage. The alkane linkage also improves functionality of the modified nucleotide by decreasing reactivity of the modified nucleotide with cell lysates. The PEG spacer increases hydrophilicity of the modified nucleotide to increase accessibility of the biotin for detection.

In one embodiment, the biotinylated nucleotide compounds have the following structure: P1-P2-Nus-Alk-Lnk-Obs (I) or its salt, conjugate base, tautomer, or ionized form where P1 and P2 are phosphate groups;

Nus is a nucleoside (a sugar (e.g., ribose) bound to a purine or pyrimidine base);

Alk is a connecting group that can be directly or indirectly bonded between Nus and Lnk, having the structure -//—$(CH_2)_m$—Y—//- in which Y is a bond forming group selected from

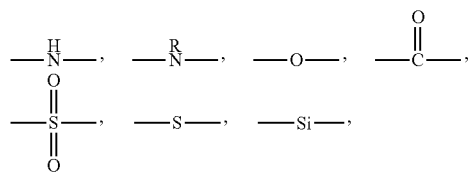

and m is an integer ranging from 3 to 6 inclusive, and the leftmost bond is to Nus and the rightmost bond is to Lnk;

Lnk is a linking group between Alk and Obs, having the following structures

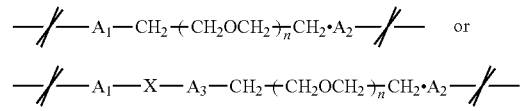

in which n is an integer ranging from 2 to 48 inclusive;

$A_1$ is a bond forming group selected from

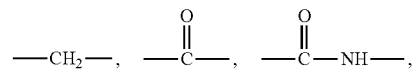

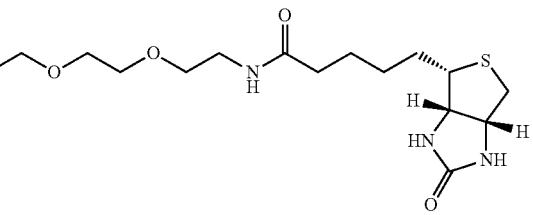

$A_2$ is a bond forming group selected from

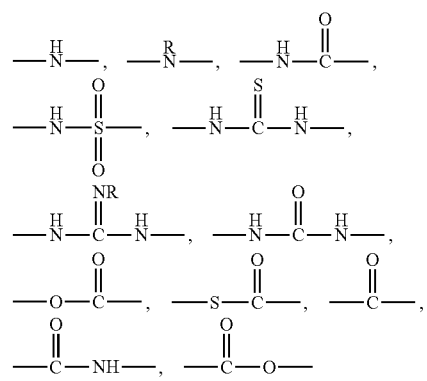

$A_3$ is a bond forming group selected from

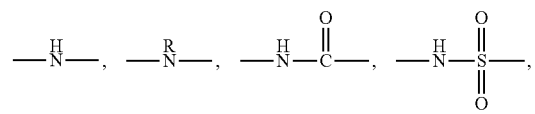

-continued

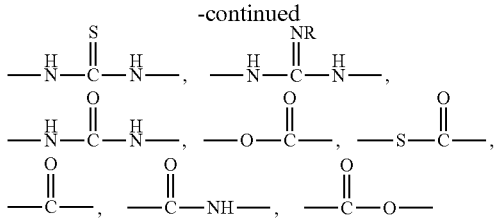

X is a cleavable group that can undergo silicon-carbon cleavage, nucleophilic cleavage, redox cleavage, photochemical cleavage, enzymatic cleavage, or exchange-based cleavage; and Obs is an observable label.

Y functions as a handle to permit attachment of detector molecules (e.g., fluorophore, biotin, etc.)

When the sugar is ribose, it has the following attachments: P1 is attached at the 5' position; P2 is attached at the 3' position; and the purine or pyrimidine base is attached at the 1' position.

The purine or pyrimidine base is selected from cytosine (C), uracil (U), adenine (A), thymine (T), guanine (G), or inosine (I) and may be modified or unmodified. Embodiments include, but are not limited to, 1-methyladenine, N6-methyladenine, N6-isopentyladenine, N,N-dimethyladenine, 7-deazaadenine, 2-thiocytosine, 3-methylcytosine, N4-acetylcytosine, 2-thiocytosine, 1-methylguanine, 2-methylguanine, 7-methylguanine, N2,N2-dimethylguanine, 7-deazaguanine, 2-thiouracil, 6-thiopurine, or 2,6-diaminopurine.

The modification may be an observable label. Observable labels include, but are not limited to, a chromogenic moiety, a fluorophore such as fluorescein, rhodamine, a commercial dye (e.g., DyLight® (Dyomics), Alexa®, Cy3, Cy5), a mass label, a spin label, or a moiety capable of binding an observable label, such as a streptavidin-binding label such as biotin, desthiobiotin or iminobiotin, or a secondary detection label such as azide, alkyne, aldehyde, or diene, which are capable of forming a covalent bond with an alkyne, phosphine, azide, hydrazide, alkoxyamine, or alkene present on an observable label. In one embodiment, the observable label is biotin, and the compound is biotin-PEG$_4$-alkane-3', 5'-cytidine-bisphosphate. In one embodiment, the observable label is an azide, and the compound is azido-PEG$_4$-alkane-3',5'-cytidine-bisphosphate. In one embodiment, the observable label is a fluorophore, and the compound is Cy5-PEG$_4$-alkane-3',5'-cytidine-bisphosphate. Labeling occurs with high efficiency and comparable sensitivity to radioisotope labeling, yet avoids the use of radioactivity with its concomitant disadvantages.

In one embodiment, n is an integer ranging from 2 to 24 inclusive, the sugar is ribose, the purine or pyrimidine base is A, C, G, U, or I, m is 3, n is 4, and the observable label is a streptavidin-binding label selected from biotin, desthiobiotin, or iminobiotin.

In one embodiment, the modified nucleotide compounds have the following structure (II):

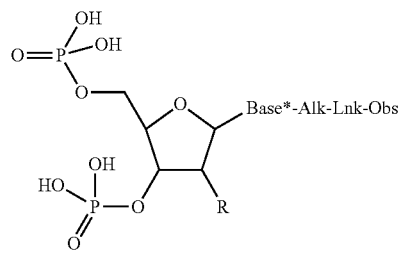

or its salt, conjugate base, tautomer, or ionized form where
Base is a purine or pyrimidine base;
R is H, OH, CH$_3$, or a hydroxyl protecting group;
Alk is a connecting group between Base* and Lnk, having the structure -//—(CH$_2$)$_m$—Y—//- in which Y is a bond forming group selected from

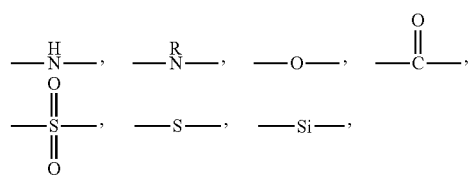

m is an integer ranging from 3 to 6 inclusive;
Lnk is a linking group having the following structures:

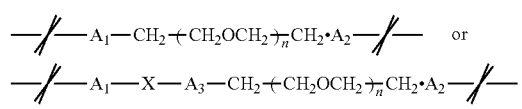

in which n is an integer ranging from 2 to 48 inclusive;
A$_1$ is a bond forming group selected from

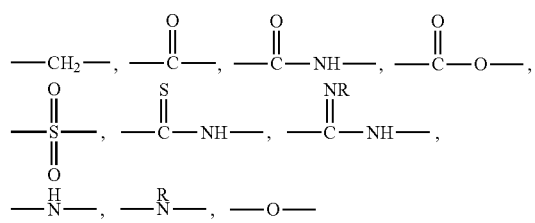

A$_2$ is a bond forming group selected from

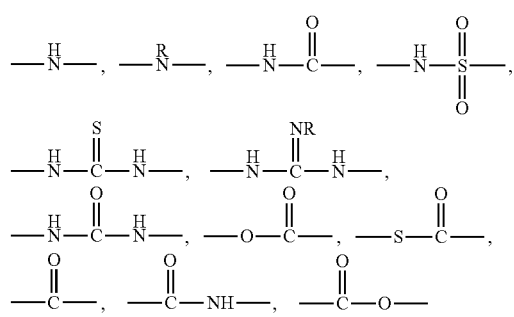

$A_3$ is a bond forming group selected from

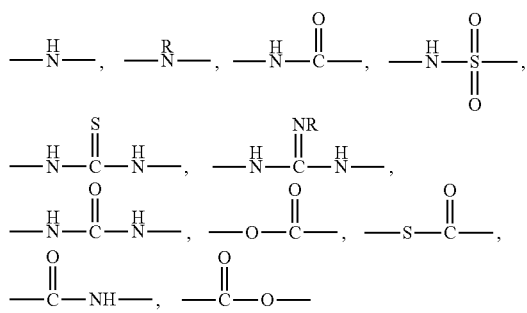

X is a cleavable group that can undergo silicon-carbon cleavage, nucleophilic cleavage, redox cleavage, acid cleavage, base cleavage, photochemical cleavage, enzymatic cleavage, or exchange-based cleavage;

Obs is an observable label moiety.

The sugar group may be ribose or deoxyribose. The purine or pyrimidine base is selected from C, U, A, G, T, or I and may be modified or unmodified. Embodiments include, but are not limited to, 1-methyladenine, N6-methyladenine, N6-isopentyladenine, N,N-dimethyladenine, 7-deazaadenine, 2-thiocytosine, 3-methylcytosine, N4-acetylcytosine, 2-thiocytosine, 1-methylguanine, 2-methylguanine, 7-methylguanine, N2,N2-dimethylguanine, 7-deazaguanine, 2-thiouracil, 6-thiopurine, or 2,6-diaminopurine.

The observable label may be a chromogenic moiety, a fluorophore such as fluorescein, rhodamine, a commercial dye (e.g., DyLight® (Dyomics), Alexa®, Cy3, Cy5), a mass label, a spin label, or a moiety capable of binding an observable label, such as a streptavidin-binding label such as biotin, desthiobiotin or iminobiotin, or a secondary detection label such as azide, alkyne, aldehyde, or diene.

In one embodiment, n is an integer ranging from 2 to 24 inclusive. In one embodiment, the sugar is ribose, the purine or pyrimidine base is A, C, G, U, or I, m is 3, n is 4, and the observable label is a streptavidin-binding label selected from biotin, desthiobiotin, or iminobiotin.

In one embodiment, the sugar is ribose, the purine or pyrimidine base is C, m is 3, Lnk is

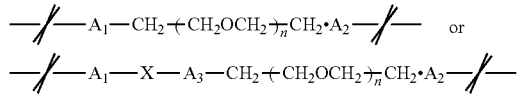

n is 4, $A_1$ is

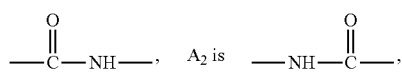

and when present, $A_3$ is 

and Obs is selected from the group consisting of biotin, a fluorophore, and an azide.

One embodiment is a method of labeling RNA by heating the desired RNA sample to at least 75° C. up to 95° C. In one embodiment, the solution containing the RNA sample contained dimethylsulfoxide (DMSO) at a concentration ranging from 0% to 25%. The RNA sample was heated for 1 minute to 5 minutes, then rapidly cooled on ice to between 2° C. and 10° C. for at least one minute. The RNA then was contacted with one of the modified nucleotide compounds having the structure P1-P2-Nus-Alk-Lnk-Obs as described above. The nucleotide was ligated to the RNA to result in a labeled RNA.

The modified nucleotide was ligated to the RNA using an enzyme such as, but not limited to, T4 RNA ligase, to result in a labeled RNA. In this embodiment, RNA was heated to at least 75° C., and up to 95° C., then cooled for at least one minute to less than 10° C. The cooled RNA was then contacted with the biotinylated cytidine bisphosphate under reaction conditions using T4 RNA ligase and including PEG having molecular weight between about 1500 and 24,000 inclusive and at a concentration ranging from 5% PEG to 20% PEG inclusive. The reaction was incubated between 30 minutes and 16 hours at temperature ranging between 16° C. and 37° C. to ligate the biotinylated cytidine bisphosphate to the RNA, resulting in a modified RNA.

Synthesis of exemplary specific compounds among each of the following modified nucleotides is subsequently described. One skilled in the art will appreciate that such synthesis schemes are representative and not limiting; one skilled in the art will know how to synthesize other specific examples using known methods and without undue experimentation. They include, but are not limited to: biotin-$PEG_4$ modifications: overview of biotin-$PEG_4$-alkane-3',5'-cytidine-bisphosphate (BPA-3',5'-pCp, compound 6), overview of biotin-$PEG_4$-SS-alkane-3',5'-cytidine-bisphosphate ($BP_4SSA$-3',5'-pCp, compound 12), biotin-$PEG_4$-SS-alkane-cytidine ($BP_4SSAC$, compound 11), and detailed reactions for biotin-$PEG_4$-SS-alkane-3',5'-cytidine-bisphosphate ($BP_4SSA$-3',5'-pCp, compound 12); biotin-$PEG_{12}$ modifications; azido-$PEG_4$ modifications; fluorophore-$PEG_4$ modifications, DyLight 550-$PEG_4$-alkane-3',5'-cytidine-bisphosphate ($Dy550P_4A$-3',5'-pCp, compound 14).

Biotin-$PEG_4$ Modification

One embodiment is a method of preparing biotin-polyethylene glycol (PEG)-alkane-3',5'-cytidine-bisphosphate. The method reacts propargyl amine with methyl trifluoroacetate to result in propargyltrifluoroacetamide. The propargyltrifluoroacetamide reacts with 5-iodocytidine to result in 5-[3-(trifluoroacetamido)propynyl]cytidine. The 5-[3-(trifluoroacetamido)propynyl]cytidine then is converted to 5-[3-(trifluoroacetamido)propyl]cytidine. The 5-[3-(trifluoroacetamido)propyl]cytidine then is converted to 5-(3-aminopropyl)cytidine. The 5-(3-aminopropyl)cytidine then is reacted with NHS-PEG-biotin to result in biotin-PEG-alkane-cytidine. The biotin-PEG-alkane-cytidine then is reacted with diphosphoryl chloride to result in biotin-polyethylene glycol (PEG)-alkane-3',5'-cytidine-bisphosphate.

Propargyltrifluoroacetamide (1) was prepared according to the following reaction:

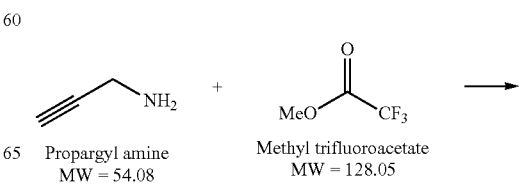

Propargyl amine
MW = 54.08

Methyl trifluoroacetate
MW = 128.05

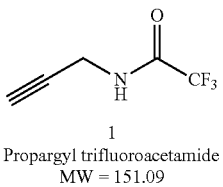

1
Propargyl trifluoroacetamide
MW = 151.09

Propargyl amine Methyl trifluoroacetate Propargyl trifluoroacetamide MW=54.08 MW=128.05 MW=151.09 Propargyl amine (4.00 g, 72.62 mmol, 1.00 equiv.) was added dropwise to methyl trifluoroacetate (11.16 g, 87.15 mmol, 1.20 equiv.) at 0° C. The reaction mixture was stirred at 0° C. for 2 h and then concentrated under reduced pressure to remove methanol. The product was purified by vacuum distillation yielding propargyltrifluoroacetamide as a colorless liquid (9.59 g, 87%). The structure was confirmed by $^1$H- and $^{19}$F-NMR.

5-[3-(trifluoroacetamido)propynyl]cytidine (2) was prepared according to the following reaction:

A 100-mL three-necked flask was charged with 5-iodocytidine (2.66 g, 7.00 mmol, 1.00 equiv.), cuprous iodide (0.267 g, 1.40 mmol, 0.20 equiv.) and dry DMF (35 mL). After complete dissolution of the reaction mixture, propargyltrifluoroacetamide (3.17 g, 21.00 mmol, 3.00 equiv.), triethylamine (1.42 g, 14.00 mmol, 2.00 equiv.) and finally tetrakis(triphenylphosphine)palladium(0) (0.809 g, 0.70 mmol, 0.10 equiv.) were added to the reaction mixture under $N_2$. The reaction was stirred at ambient temperature (around 19° C. to around 22° C.) under $N_2$ for 18-24 h. The reaction was then diluted with 70 mL of 1:1 methanol-dichloromethane and the bicarbonate form of AGI X8 resin (12.00 g) was added. After stirring for about one h, the reaction mixture was filtered and the resin was washed with 1:1 methanol-dichloromethane. The combined filtrates were rapidly concentrated with a rotary evaporator. The residue was immediately purified by flash chromatography. Removal of solvent from the appropriate fractions afforded 1.84 g (67%) of 5-[3-(trifluoroacetamido)propynyl]cytidine as a light brown solid, which was confirmed by $^1$H-NMR.

5-[3-(trifluoroacetamido)propyl]cytidine (3) was prepared according to the following reaction:

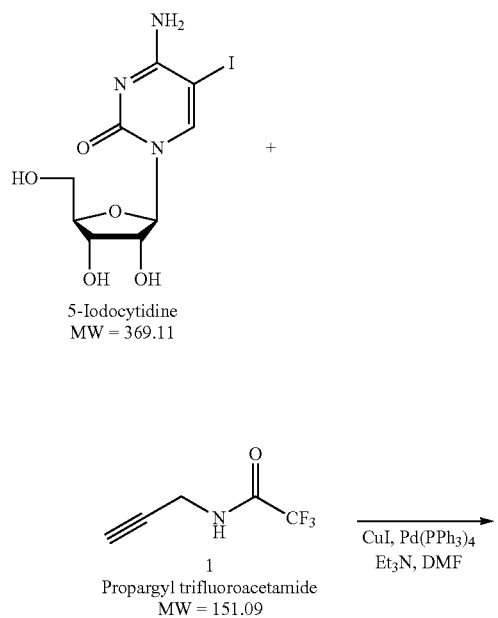

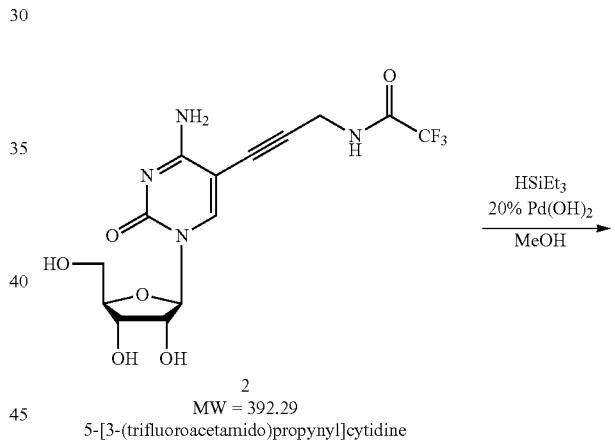

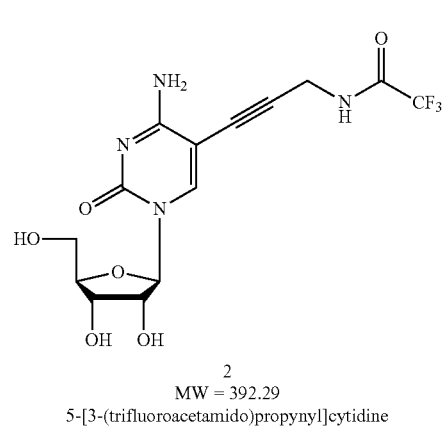

2
MW = 392.29
5-[3-(trifluoroacetamido)propynyl]cytidine

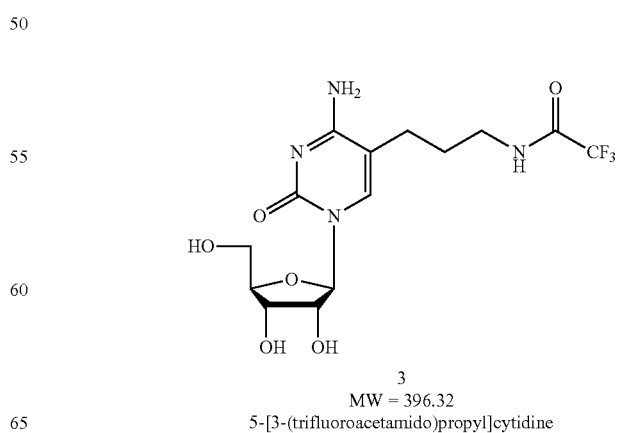

3
MW = 396.32
5-[3-(trifluoroacetamido)propyl]cytidine

5-[3-(trifluoroacetamido)propynyl]cytidine (1.25 g, 3.19 mmol, 1.00 equiv.) was dissolved in methanol (30 mL). Palladium hydroxide (0.25 g, 20 wt./wt. % based on propynyl cytidine) and triethylsilane (3.71 g, 31.90 mmol, 10.00 equiv.) were added to the reaction mixture. After 20-24 hours at ambient temperature, the reaction mixture was filtered through glass fiber and the filtrate was concentrated under reduced pressure giving a dark brown residue. The residue was purified by flash chromatography. Removal of solvent from the appropriate fractions afforded 0.85 g (71%) of 5-[3-(trifluoroacetamido)propyl]cytidine as a cream colored solid, which was confirmed by $^1$H-NM.

5-(3-aminopropyl)cytidine (4) was prepared according to the following reaction:

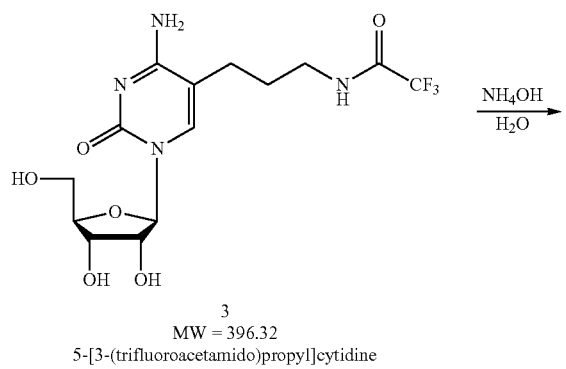

3
MW = 396.32
5-[3-(trifluoroacetamido)propyl]cytidine

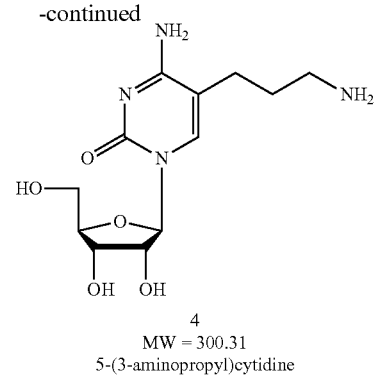

4
MW = 300.31
5-(3-aminopropyl)cytidine

5-[3-(trfluoroacetamido)propyl]cytidine (0.69 g, 1.74 mmol) was dissolved in DI H$_2$O (8.5 mL). After complete dissolution, concentrated ammonium hydroxide (NH$_4$OH) (8.5 mL) was added to the reaction mixture. The reaction solution was stirred at ambient temperature for 2-3 h and then concentrated under reduced pressure giving the crude product as yellow-orange residue. The crude product was dissolved in deionized H$_2$O (10 mL) and AG50W-X8 resin (2.5 g) was added to the solution. The suspension was stirred for 15 min and filtered over a bed of AG50W-X8 resin (2.5 g). The resin was washed with DI H$_2$O and the product was then eluted off of the resin by washing the resin with deionized H$_2$O/conc. NH$_4$OH, 4:1, collecting fractions (monitored by TLC). Removal of solvent from the appropriate fractions afforded 0.51 g (98%) of 5-(3-aminopropyl)cytidine as light tan solid, which was confirmed by $^1$H-NMR.

Biotin-PEG$_4$-alkane-cytidine (BPAC, 5) was prepared according to the following reaction:

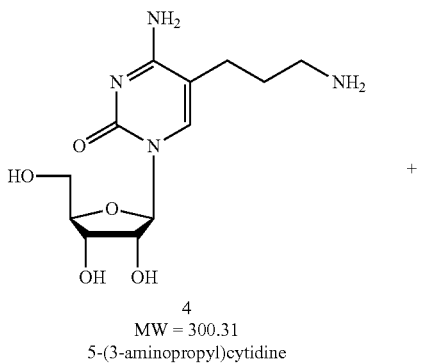

4
MW = 300.31
5-(3-aminopropyl)cytidine

+

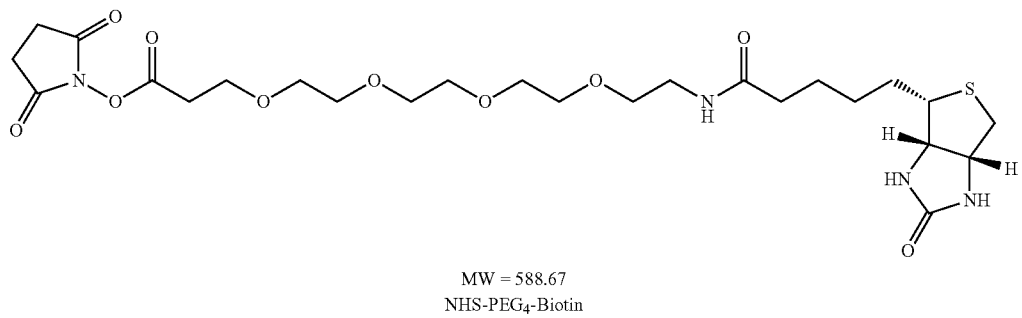

MW = 588.67
NHS-PEG$_4$-Biotin

↓ DMF

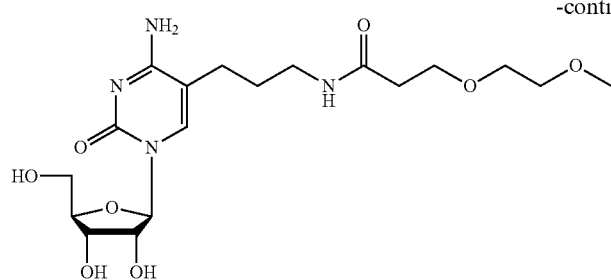
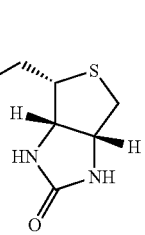

5
MW = 773.89
BPAC

NHS-PEG$_4$-biotin (0.196 g, 0.333 mmol, 1.00 equiv.) was dissolved in DMF (10 mL). 5-(3-aminopropyl)cytidine) (0.100 g, 0.333 mmol, 1.00 equiv.) was added to the reaction solution. The reaction solution was stirred at ambient temperature under N$_2$ atmosphere. After 20-24 h, the reaction mixture was concentrated under reduced pressure giving the crude product. The crude product was purified by flash chromatography. Removal of solvent from the appropriate fractions afforded 0.18 g (69%) of BPAC as a white solid, which was confirmed by $^1$H-NMR.

Biotin-PEG$_4$-alkane-3',5'-cytidine-bisphosphate (BPA-3', 5'-pCp, 6) was prepared according to the following reaction:

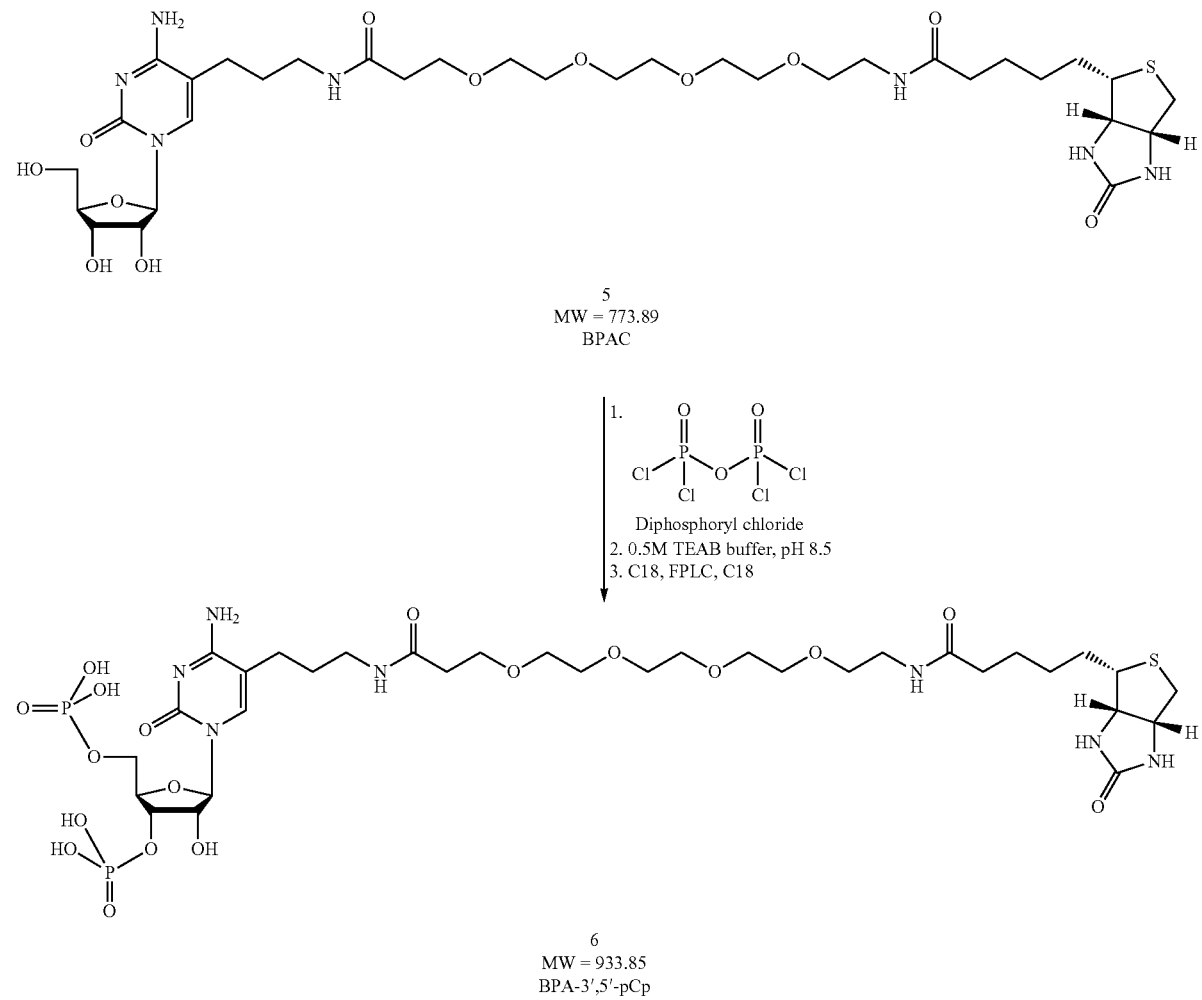

BPAC (0.061 g, 0.079 mmol, 1.00 equiv.) was partially dissolved in diphosphoryl chloride (196 μL, 1.66 mmol, 21.00 equiv.), previously cooled to −10° C. to −15° C. in a 1-mL Reacti-Vial™. The mixture was then stirred at −10° C.

to −15° C. After 5 h, the reaction was quenched by addition of ice cold water (1-2 mL) and, immediately thereafter, with a chilled solution of 0.5 M TEAB buffer, pH 8.5 (17 mL). Upon stabilization at neutral pH, the colorless solution was stirred at ambient temperature for 30 min and concentrated using a rotary evaporator until complete removal of TEAB. The solution was desalted using a C18 cartridge (Waters) and purified by FPLC (MonoQ 10/100GL column, GE) using a pH gradient. After a final desalting using again a C18 cartridge (Waters), BPA-3',5'-pCp was isolated after lyophilization as a white solid (10 mg, 9%), which was confirmed by $^1$H-NMR & HPLC.

Overview of Preparation of BIOTIN-PEG$_4$-SS-AL-KANE-3',5'-CYTIDINE-BISPHOSPHATE (BP$_4$SSA-3',5'-pCp, Compound 12)

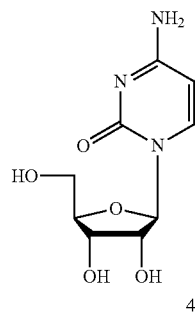

4

+

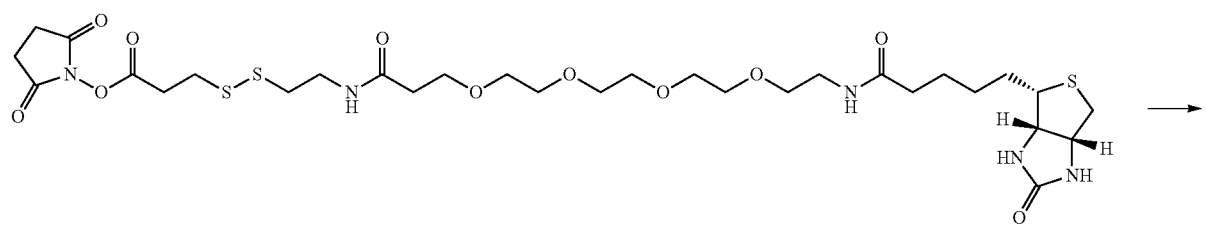

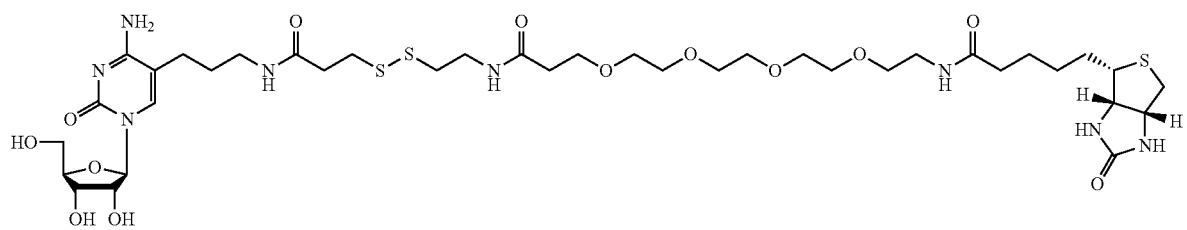

11

11  $\xrightarrow{\begin{array}{c}\text{1. Phosphorylation}\\\text{2. C18, FPLC, C18}\end{array}}$

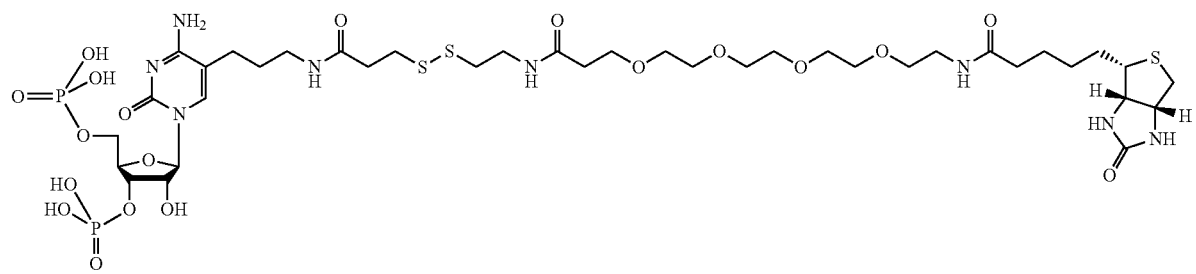

12

The reaction scheme to prepare biotin-polyethylene glycol (PEG)-SS-alkane-3',5'-cytidine-bisphosphate is as follows. The 5-(3-aminopropyl)cytidine (compound 4) is reacted with NHS—SS-PEG-biotin to result in biotin-PEG-SS-alkane-cytidine (compound 11). The biotin-PEG-SS-alkane-cytidine (compound 11) then is reacted with diphosphoryl chloride to result in biotin-polyethylene glycol (PEG)-SS-alkane-3',5'-cytidine-bisphosphate (compound 12).

Preparation of
BIOTIN-PEG$_4$-SS-ALKANE-CYTIDINE
(BP$_4$SSAC, Compound 11)

NHS—SS-PEG$_4$-biotin (0.250 g, 0.333 mmol, 1.00 equiv.) was dissolved in DMF (10 mL). 5-(3-aminopropyl)cytidine) (0.100 g, 0.333 mmol, 1.00 equiv.) was added to the reaction solution. The reaction solution was stirred at ambient temperature under N$_2$ atmosphere. After 20-24 hours, the reaction mixture was concentrated under reduced pressure giving the crude product. The crude product was purified by flash chromatography. Removal of solvent from the appropriate fractions afforded 0.19 g (61%) of BP$_4$SSAC (compound 11) as a white solid, which was confirmed by $^1$H-NMR.

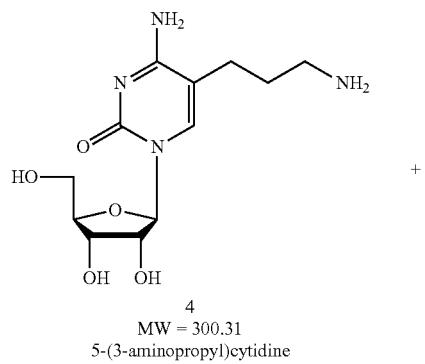

4
MW = 300.31
5-(3-aminopropyl)cytidine

+

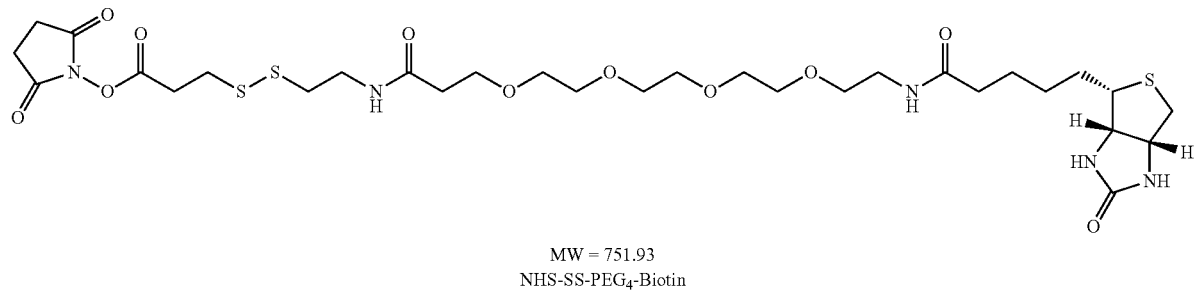

MW = 751.93
NHS-SS-PEG$_4$-Biotin

↓ DMF

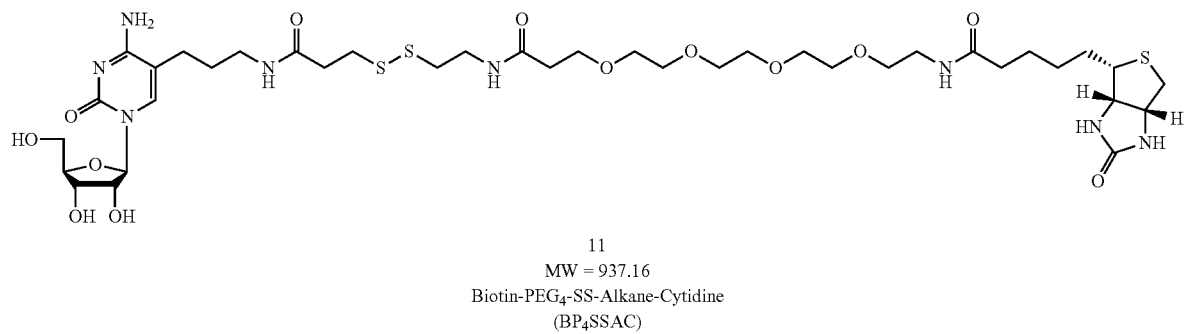

11
MW = 937.16
Biotin-PEG$_4$-SS-Alkane-Cytidine
(BP$_4$SSAC)

Preparation of BIOTIN-PEG$_4$-SS-ALKANE-3',5'-CYTIDINE-BISPHOSPHATE (BP$_4$SSA-3',5'-pCp, Compound 12)

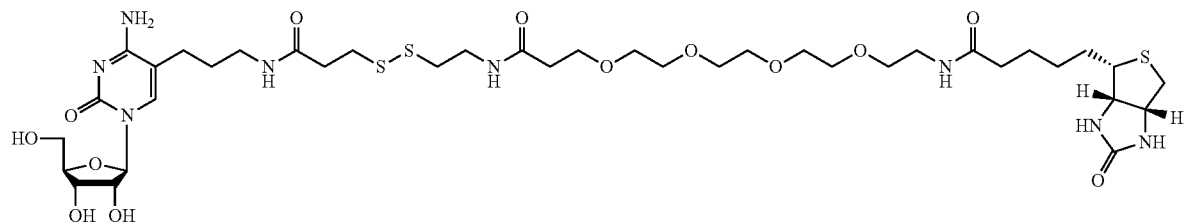

11
MW = 937.16
Biotin-PEG$_4$-SS-Alkane-Cytidine
(BP$_4$SSAC)

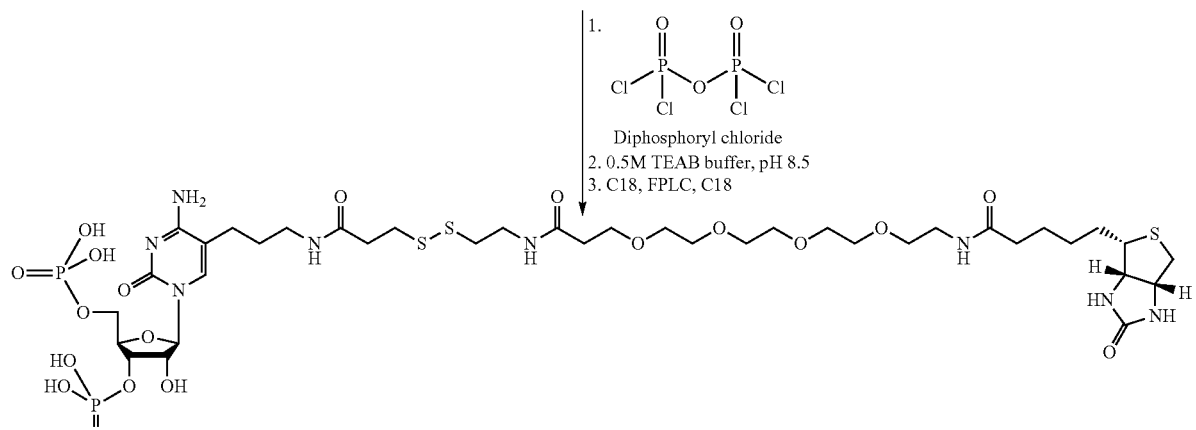

12
MW = 1097.12
Biotin-PEG$_4$-SS-Alkane-3',5'-Bisphosphate-Cytidine
(BP$_4$SSA-3',5'-pCp)

BP$_4$SSAC (0.074 g, 0.079 mmol, 1.00 equiv.) was partially dissolved in diphosphoryl chloride (196 µL, 1.66 mmol, 21.00 equiv.), previously cooled to −10° C. to −15° C. in a 1-mL Reacti-Vial™. The mixture was then stirred at −10° C. to −15° C. After five hours, the reaction was quenched by addition of ice cold water (1-2 mL) and, immediately thereafter, with a chilled solution of 0.5M TEAB buffer, pH 8.5 (17 mL). Upon stabilization at neutral pH, the colorless solution was stirred at ambient temperature for 30 min and concentrated using a rotary evaporator until complete removal of TEAB. The solution was desalted using a C18 cartridge (Waters) and purified by FPLC (MonoQ 10/100GL column, GE) using a pH gradient. After a final desalting using again a C18 cartridge (Waters), BP$_4$SSA-3',5'-pCp (compound 12) was isolated after lyophilization as a white solid (5 mg, 6%), which was confirmed by $^1$H-NMR and HPLC.

Biotin-PEG$_1$, Modification

Preparation of BIOTIN-PEG$_{12}$-ALKANE-CYTIDINE (BP$_{12}$AC, Compound 7)

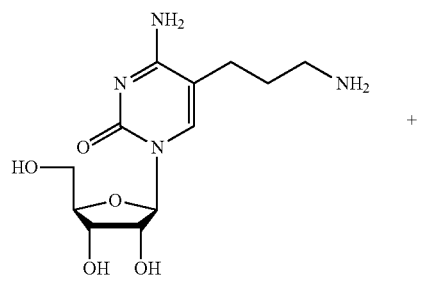

4
MW = 300.31
5-(3-aminopropyl)cytidine

-continued

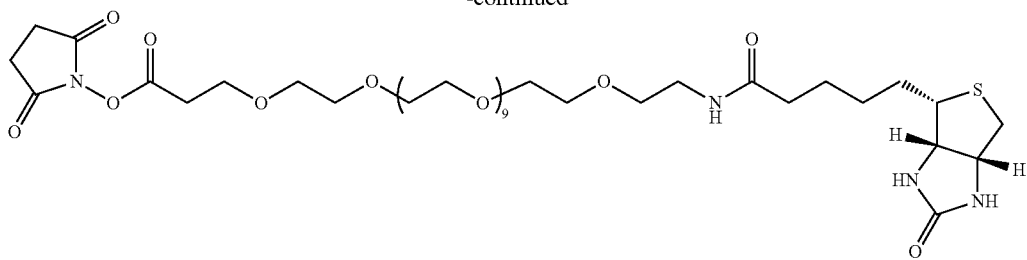

MW = 941.09
NHS-PEG$_{12}$-Biotin

↓ DMF

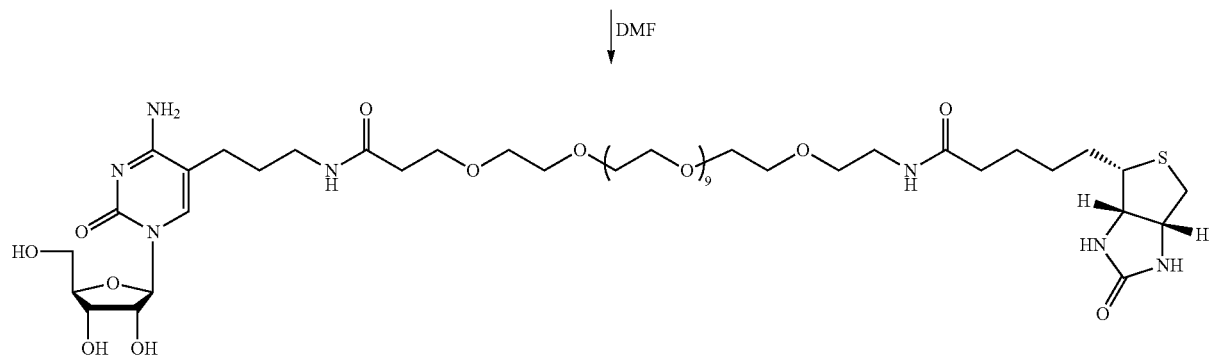

7
MW = 1126.31
Biotin-PEG$_{12}$-Alkane-Cytidine
(BP$_{12}$AC)

NHS-PEG$_{12}$-biotin (0.313 g, 0.333 mmol, 1.00 equiv.) was dissolved in DMF (10 mL). 5-(3-aminopropyl)cytidine) (0.100 g, 0.333 mmol, 1.00 equiv., compound 4) was added to the reaction solution. The reaction solution was stirred at ambient temperature under N$_2$ atmosphere. After 20-24 h, the reaction mixture was concentrated under reduced pressure giving the crude product. The crude product was purified by flash chromatography. Removal of solvent from the appropriate fractions afforded 0.27 g (72%) of BP$_{12}$AC (compound 7) as a light yellow foam, which was confirmed by $^1$H-NMR.

Preparation of BIOTIN-PEG$_{12}$-ALKANE-3',5'-BIS-PHOSPHATE-CYTIDINE (BP$_{12}$A-3',5'-pCp, Compound 8)

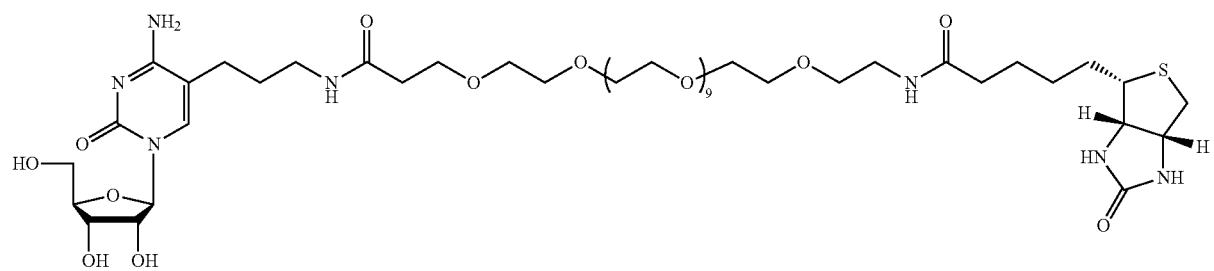

7
MW = 1126.31
Biotin-PEG$_{12}$-Alkane-Cytidine
(BP$_{12}$AC)

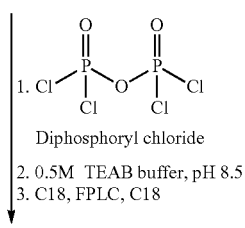

Diphosphoryl chloride 2. 0.5M TEAB buffer, pH 8.5
3. C18, FPLC, C18

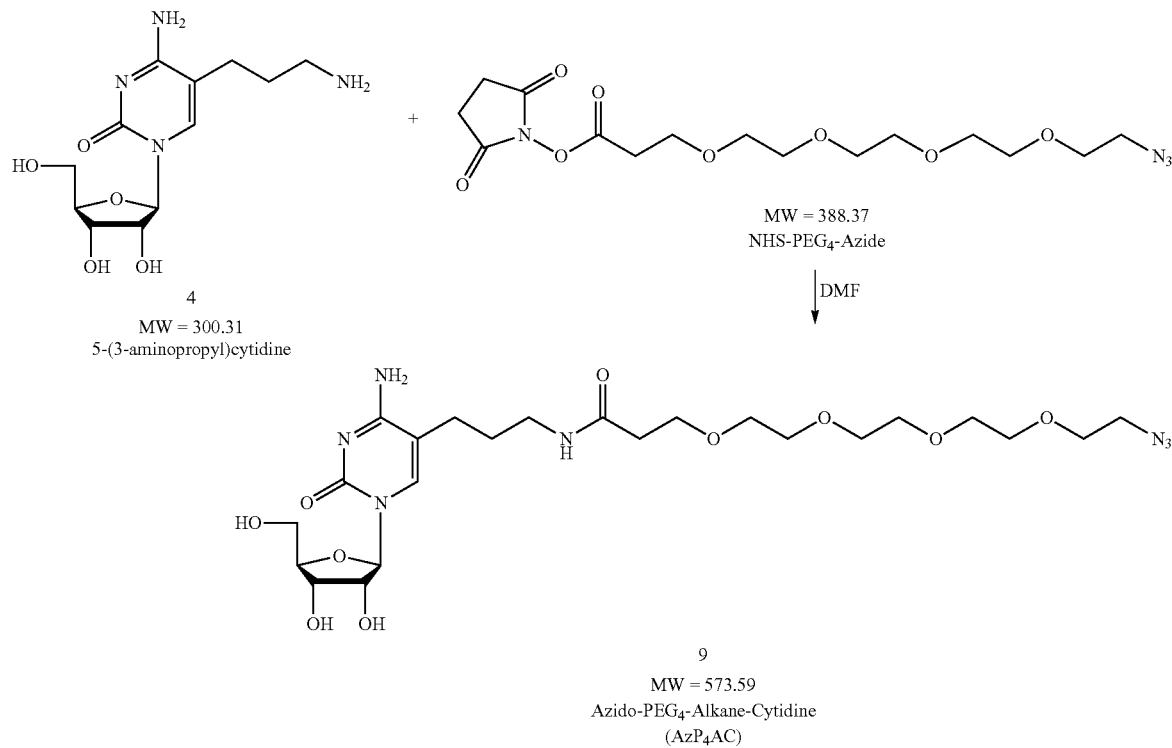

8
MW = 1286.27
Biotin-PEG$_{12}$-Alkane-3',5'-Bisphosphate-Cytidine
(BP$_{12}$A-3',5'-pCp)

Biotin-PEG$_{12}$-alkane-cytidine (0.135 g, 0.120 mmol, 1.00 equiv., compound 7) was partially dissolved in diphosphoryl chloride (315 μL, 2.40 mmol, 20.00 equiv.), previously cooled to −10 to −15° C. in a 1-mL Reacti-Vial™. The mixture was stirred at −10 to −15° C. After five hours, the reaction was quenched by adding ice cold water (1-2 mL) and immediately after with a chilled solution of 0.5M TEAB buffer, pH 8.5 (40 mL). Upon stabilization at neutral pH, the colorless solution was stirred at ambient temperature for 30 min and concentrated using a rotary evaporator until TEAB was completely removed. The solution was desalted using a C18 cartridge (Waters) and purified by FPLC (MonoQ 10/100GL column, GE) using a pH gradient. After final desalting using a C18 cartridge (Waters), biotin-PEG$_{12}$-alkane-3',5'-cytidine-bisphosphate (compound 8) was isolated after lyophilization as a sticky white solid (8 mg, 5%), which was confirmed by 1H-NMR and HPLC.

Azido-PEG$_4$ Modification

Azido-PEG$_4$-alkane-3',5'-cytidine-bisphosphate, Compound 9

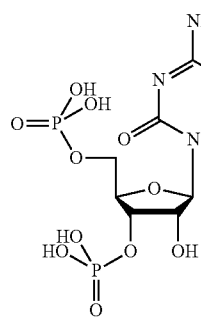

4
MW = 300.31
5-(3-aminopropyl)cytidine

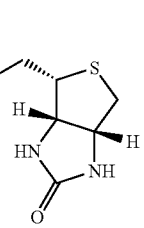

MW = 388.37
NHS-PEG$_4$-Azide

|DMF

9
MW = 573.59
Azido-PEG$_4$-Alkane-Cytidine
(AzP$_4$AC)

One embodiment is a method of preparing azido-PEG$_4$-alkane-3',5'-cytidine-bisphosphate. The 5-(3-aminopropyl)cytidine was synthesized as described above, then was reacted with NHS-PEG$_4$-azide to result in azido-PEG$_4$-alkane-cytidine. The azido-PEG$_4$-alkane-cytidine was then reacted with diphosphoryl chloride to result in azido-PEG$_4$-alkane-3',5'-cytidine-bisphosphate.

NHS-PEG₄-azide (0.408 g, 1.05 mmol, 1.00 equiv.) was dissolved in DMF (32 mL). The 5-(3-aminopropyl)cytidine) (0.315 g, 1.05 mmol, 1.00 equiv.) was added to the reaction solution. The reaction solution was stirred at ambient temperature under N₂ atmosphere. After 20-24 hours, the reaction mixture was concentrated under reduced pressure giving the crude product. The crude product was purified by flash chromatography. Removal of solvent from the appropriate fractions afforded 0.378 g (63%) of azido-PEG₄-alkane-cytidine (compound 9) as a near colorless glass, which was confirmed by 1H-NMR.

Azido-PEG₄-alkane-3',5'-Bisphosphate-Cytidine (AzP₄A-3',5'p-C-p), Compound 10 chloride (688 μL, 5.24 mmol, 20.00 equiv.), previously cooled to −10 to −15° C. in a 1 mL Reacti-Vial™. The mixture was then stirred at −10 to −15° C. After five hours, the reaction was quenched by adding ice cold water (2-3 mL) and then immediately with a chilled solution of 0.5M TEAB buffer, pH 8.5 (87 mL). Upon stabilization at neutral pH, the colorless solution was stirred at ambient temperature for 30 min and concentrated using a rotary evaporator until TEAB was complete removed. The solution was desalted using a C18 cartridge (Waters) and purified by FPLC (MonoQ 10/100GL column, GE) using a pH gradient. After final desalting using again a C18 cartridge (Waters), azido-PEG₄-alkane-3',5'-cytidine-bisphosphate (compound 10)

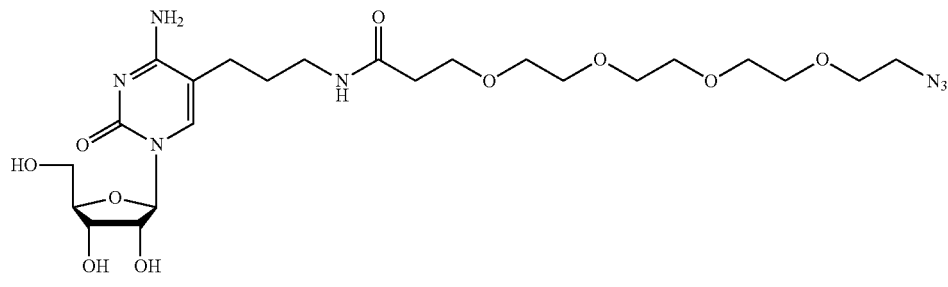

9
MW = 573.59
Azido-PEG₄-Alkane-Cytidine
(AzP₄AC)

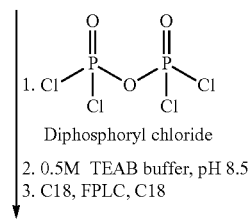

Diphosphoryl chloride 2. 0.5M TEAB buffer, pH 8.5
3. C18, FPLC, C18

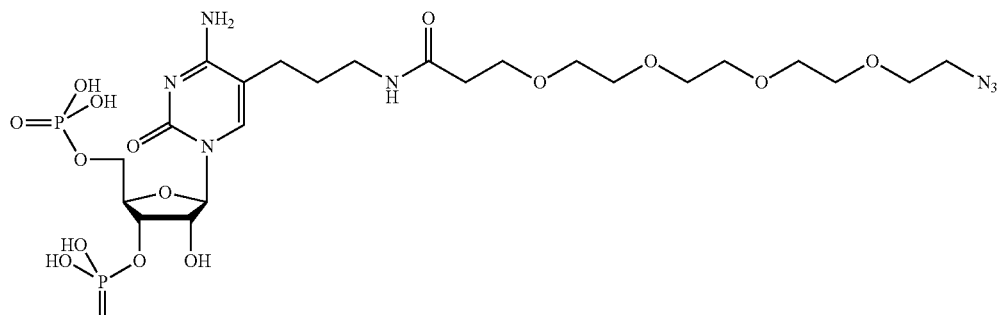

10
MW = 733.55
Azido-PEG₄-Alkane-3',5'-Bisphosphate-Cytidine
(AzP₄A-3',5'-pCp)

Azido-PEG₄-alkane-cytidine (0.150 g, 0.262 mmol, 1.00 equiv., compound 9) was partially dissolved in diphosphoryl was isolated after lyophilization as a sticky white solid (10 mg, 6%), confirmed by 1H-NMR and HPLC.

Fluorophore-PEG$_4$ Modifications

Overview—Preparation of DyLight 550-PEG$_4$-ALKANE-3',5'-CYTIDINE-BISPHOSPHATE (Dy550P$_4$A-3',5'-pCp, 14)

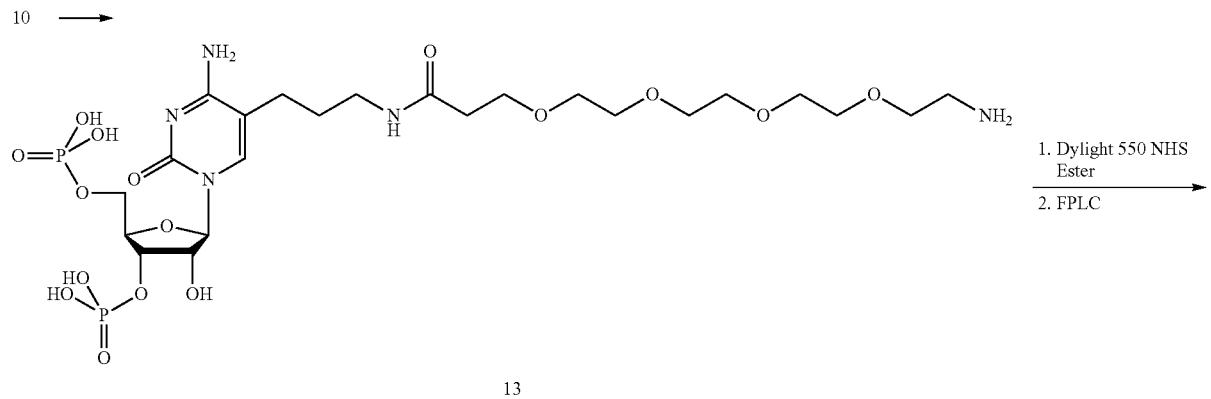

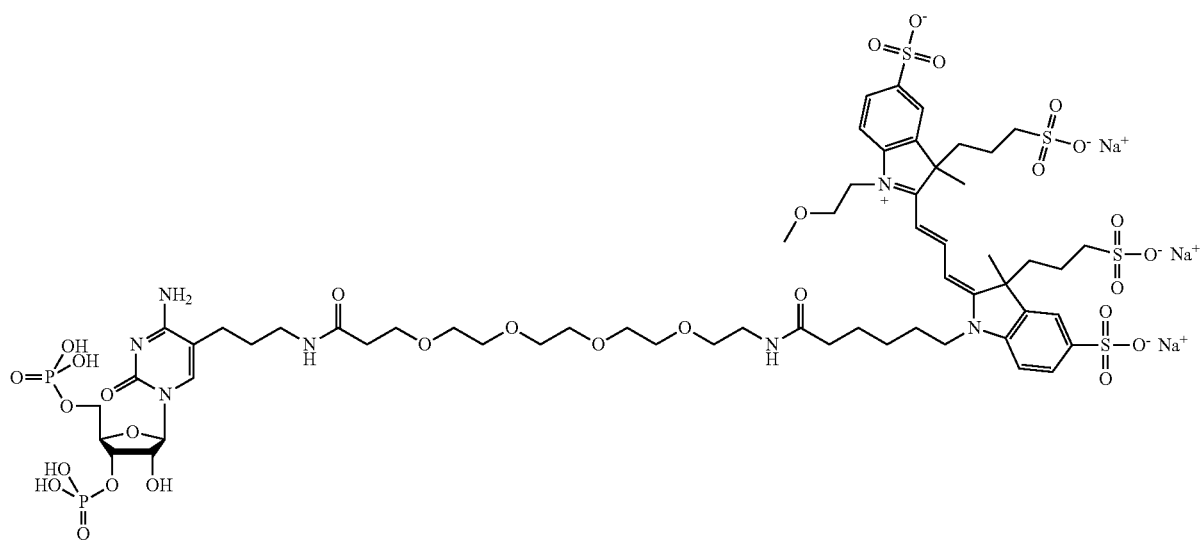

DyLight 550-polyethylene glycol (PEG)-alkane-3',5'-cytidine-bisphosphate (compound 14) is prepared as follows. The azido-PEG$_4$-alkane-3',5'-cytidine-bisphosphate (compound 10) was synthesized as described above, then allowed to react with tris(2-carboxyethyl)phosphine hydrochloride (TCEP) to result in amino-PEG$_4$-alkane-3,'5'-cytidine bisphosphate (compound 13). The amino-PEG$_4$-alkane-3,'5'-cytidine bisphosphate (compound 13) was then reacted with DyLight 550 NHS ester to result in 550-polyethylene glycol (PEG)-alkane-3',5'-cytidine-bisphosphate (compound 14).

Preparation of AMINO-PEG₄-ALKANE-3',5'-BIS-PHOSPHATE-CYTIDINE (AmP₄A-3',5'-pCp, 13)

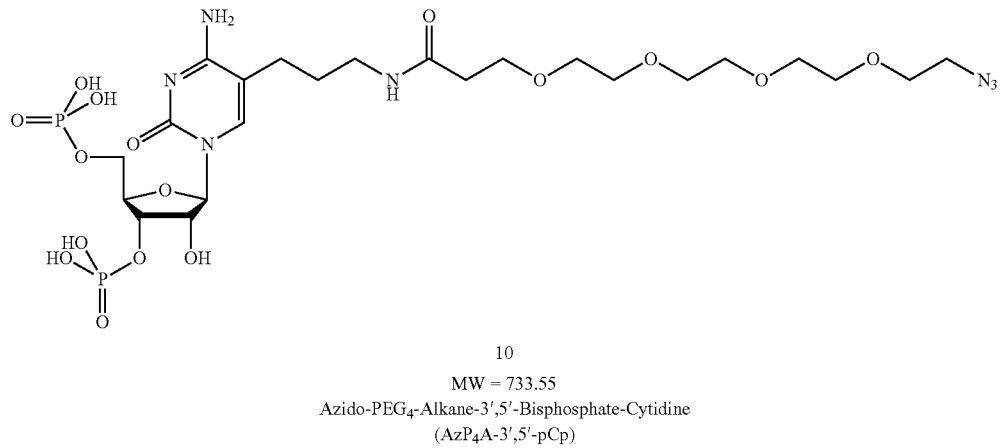

10
MW = 733.55
Azido-PEG₄-Alkane-3',5'-Bisphosphate-Cytidine
(AzP₄A-3',5'-pCp)

1. TCEP
2. FPLC

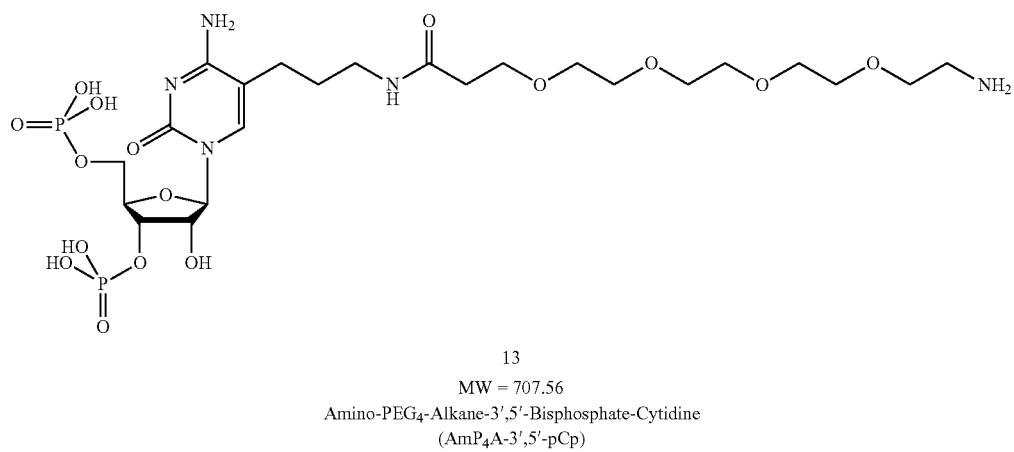

13
MW = 707.56
Amino-PEG₄-Alkane-3',5'-Bisphosphate-Cytidine
(AmP₄A-3',5'-pCp)

Azido-PEG₄-alkane-3',5'-bisphosphate-cytidine (3.56 µmol, 1.00 equiv., compound 10) was dissolved in 200 mM Tris/HCl, pH 7.5 (800 µL). Tris(2-carboxyethyl)phosphine hydrochloride (TCEP) (17.54 mg, approx. 5.00 equiv.) was dissolved in 200 mM Tris/HCl, pH 7.5 (688 µL). The TCEP solution (200 µL) was added to the solution of azide and the reaction was mixed at ambient temperature. After 1-3 h, the reaction mixture was purified by FPLC and the fractions containing product were treated directly with DyLight 550 NHS ester to result in amino-PEG₄-alkane-3',5'-bisphosphate cytidine (compound 13).

Preparation of DyLight550-PEG$_4$-ALKANE-3',5'-BISPHOSPHATE-CYTIDINE (Dy550P$_4$A-3',5'-pCp, 14)

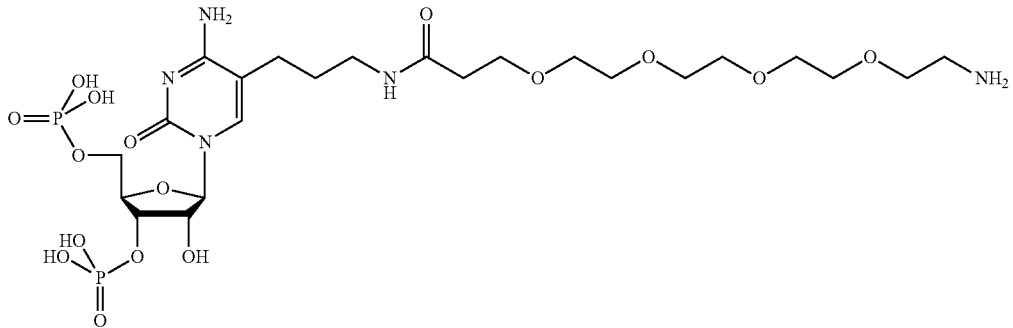

13
MW = 707.56
Amino-PEG$_4$-Alkane-3',5'-Bisphosphate-Cytidine
(AmP$_4$A-3',5'-pCp)

1. Dylight 550 NHS Ester
2. FPLC

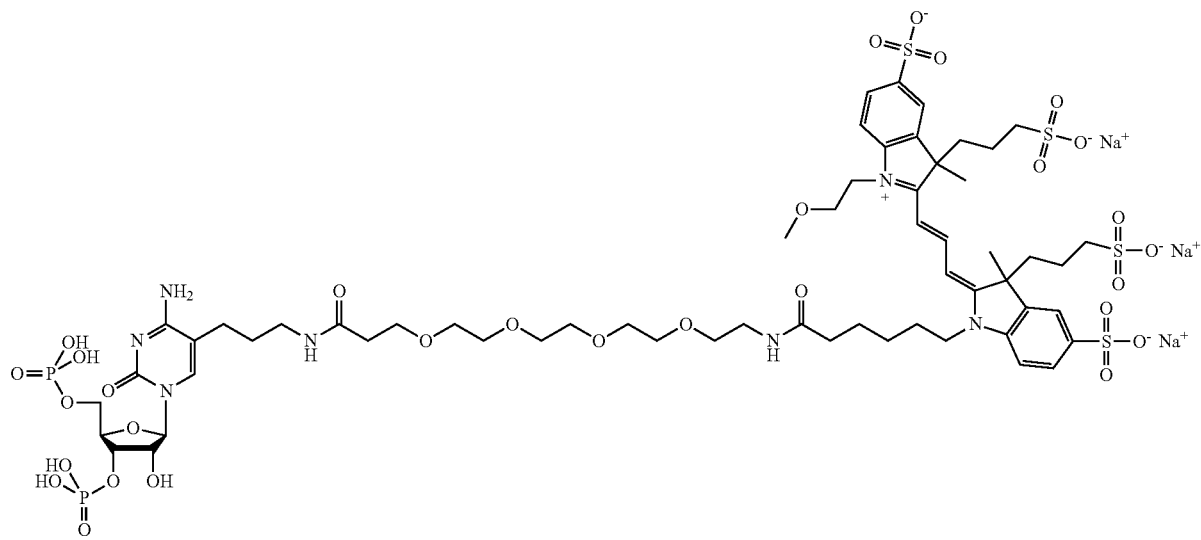

14
MW = 1632.52
DyLight550-PEG$_4$-Alkane-3',5'-Bisphosphate-Cytidine
(Dy550P$_4$A=3',5'-pCp)

The pH of an FPLC fraction (2 mL) containing amino-PEG$_4$-alkane-3',5'-bisphosphate-cytidine (compound 13) was adjusted to pH 7.0 by adding 1M HEPES, pH 7.3. Separately, a 1 mM solution of DyLight 550 NHS ester was prepared by dissolving DyLight 550 NHS ester (MW=1040.05, 1 mg) in ultra pure water (960 µL). Amino-PEG$_4$-alkane-3',5'-bisphosphate-cytidine (0.25 mL) and DyLight 550 NHS ester (0.25 mL) were combined in a separate reaction vessel and were mixed with rotation for 1 h at ambient temperature. The reaction mixture was purified by FPLC (MonoQ 10/100GL column, GE) using a pH and salt gradient. Fractions containing product were dialyzed and subsequently lyophilized, yielding DyLight550-PEG$_4$-alkane-3',5'-cytidine-bisphosphate (compound 14) as a dark pink residue.

Other exemplary compounds follow. Examples of fluorescent compounds include, but are not limited to, the following:

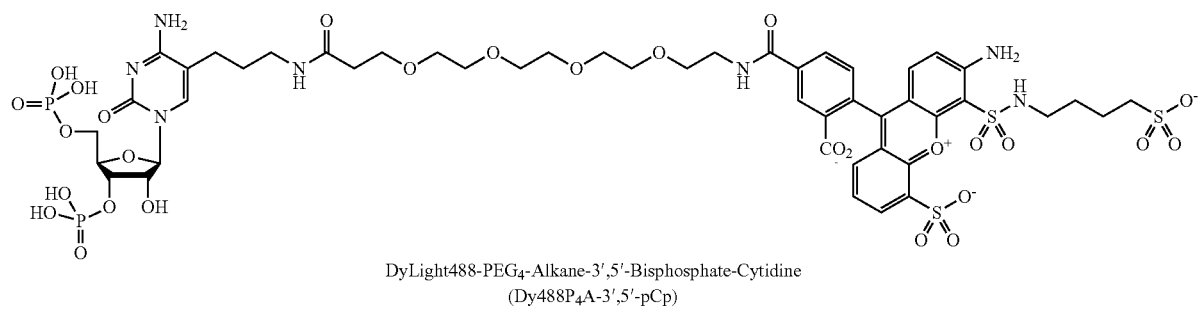
DyLight488-PEG$_4$-Alkane-3′,5′-Bisphosphate-Cytidine
(Dy488P$_4$A-3′,5′-pCp)
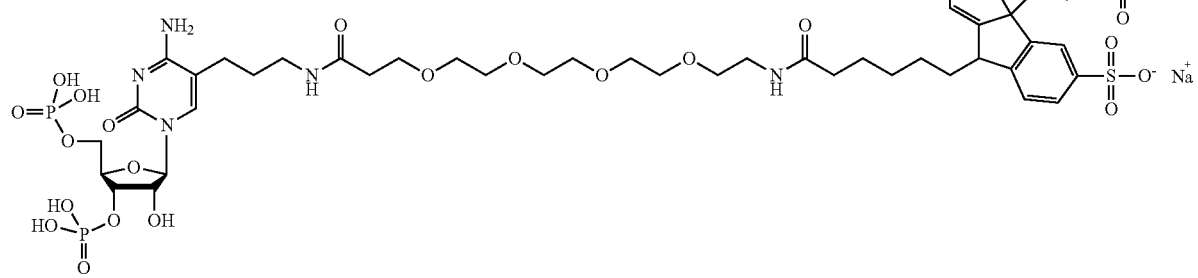
DyLight650-PEG$_4$-Alkane-3′,5′-Bisphosphate-Cytidine
(Dy650P$_4$A-3′,5′-pCp)
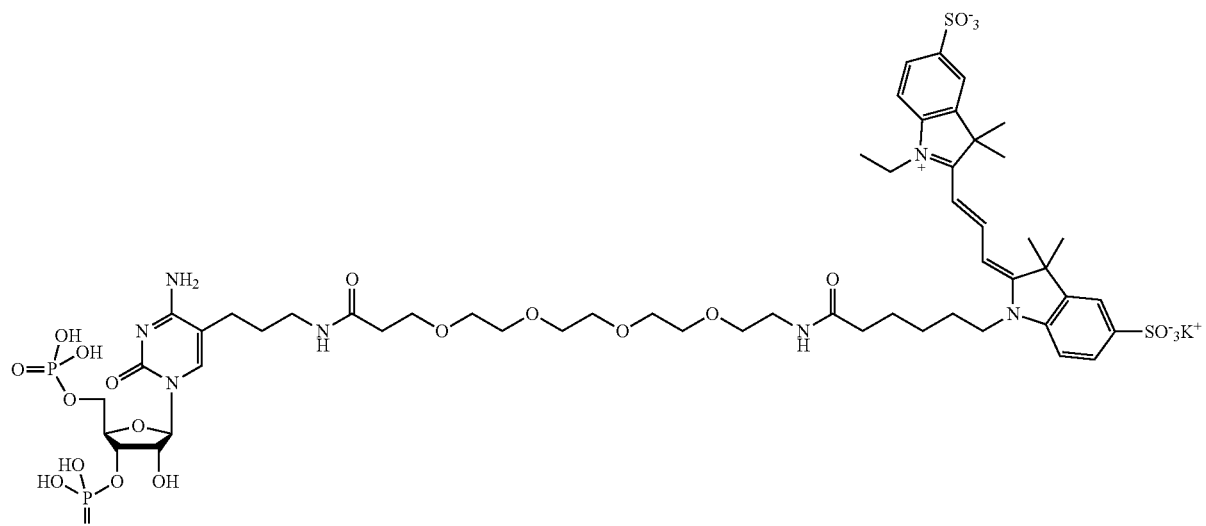
Cy3-PEG$_4$-Alkane-3′,5′-Bisphosphate-Cytidine
(Cy3P$_4$A-3′,5′-pCp)

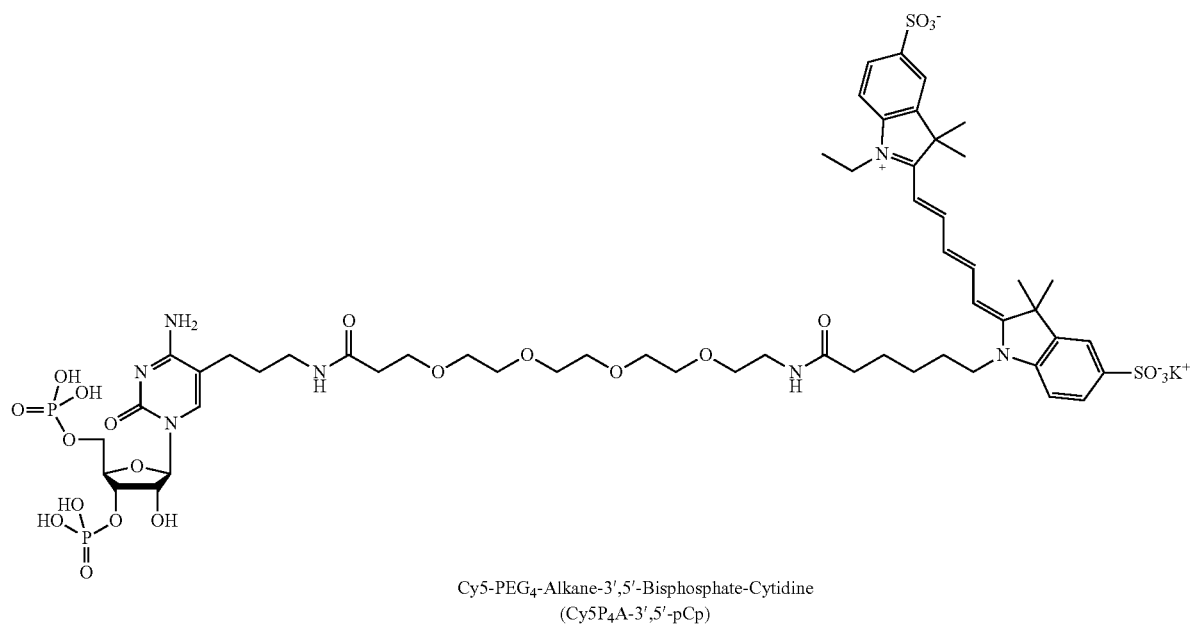
Cy5-PEG₄-Alkane-3′,5′-Bisphosphate-Cytidine
(Cy5P₄A-3′,5′-pCp)
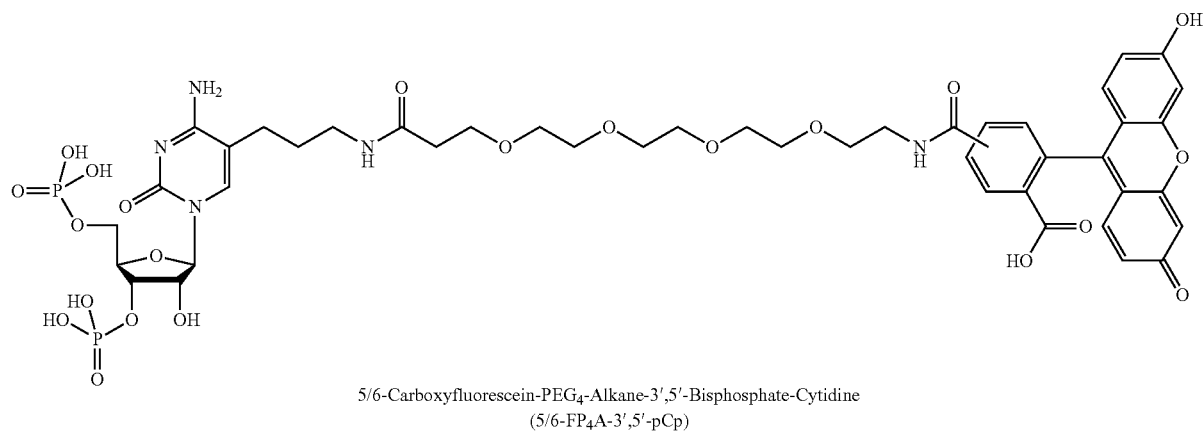
5/6-Carboxyfluorescein-PEG₄-Alkane-3′,5′-Bisphosphate-Cytidine
(5/6-FP₄A-3′,5′-pCp)
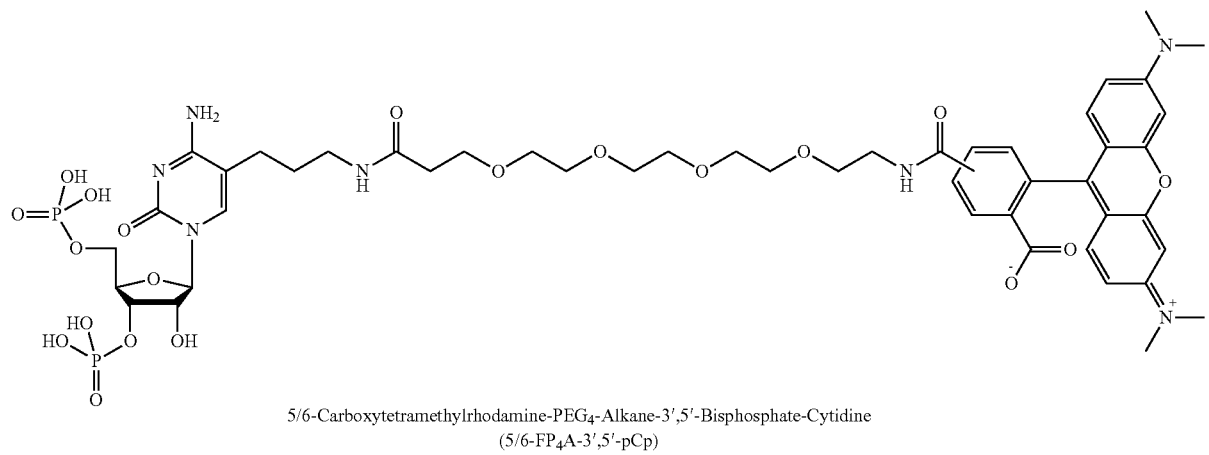
5/6-Carboxytetramethylrhodamine-PEG₄-Alkane-3′,5′-Bisphosphate-Cytidine
(5/6-FP₄A-3′,5′-pCp)

-continued

Examples of compounds with mass labels include, but are not limited to, the following:

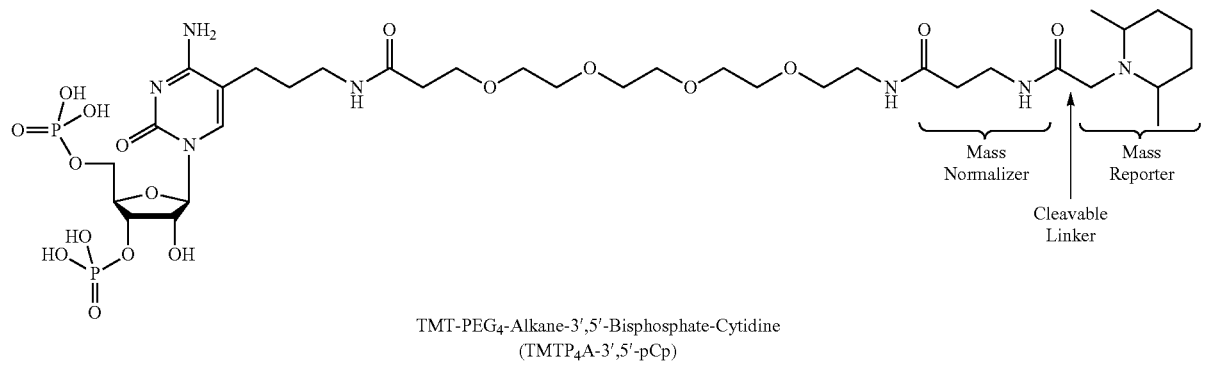

TMT-PEG$_4$-Alkane-3′,5′-Bisphosphate-Cytidine
(TMTP$_4$A-3′,5′-pCp)

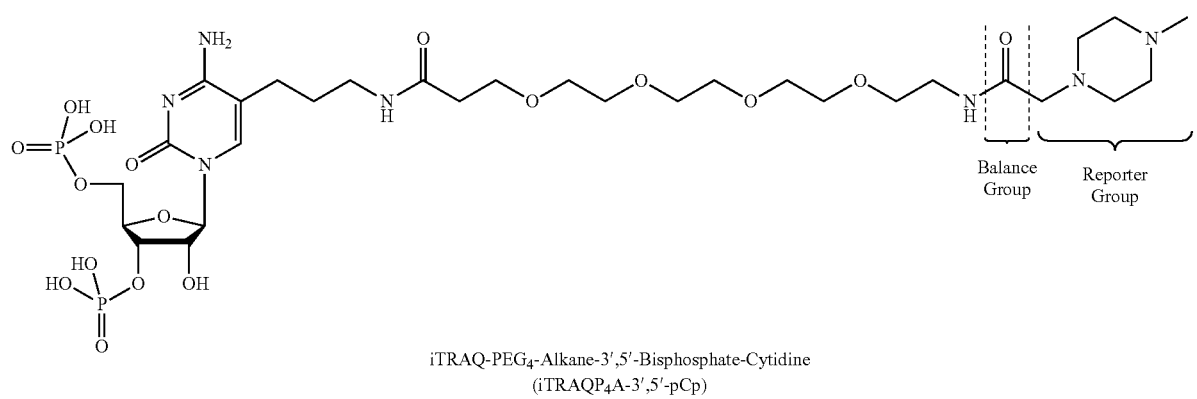

iTRAQ-PEG$_4$-Alkane-3′,5′-Bisphosphate-Cytidine
(iTRAQP$_4$A-3′,5′-pCp)

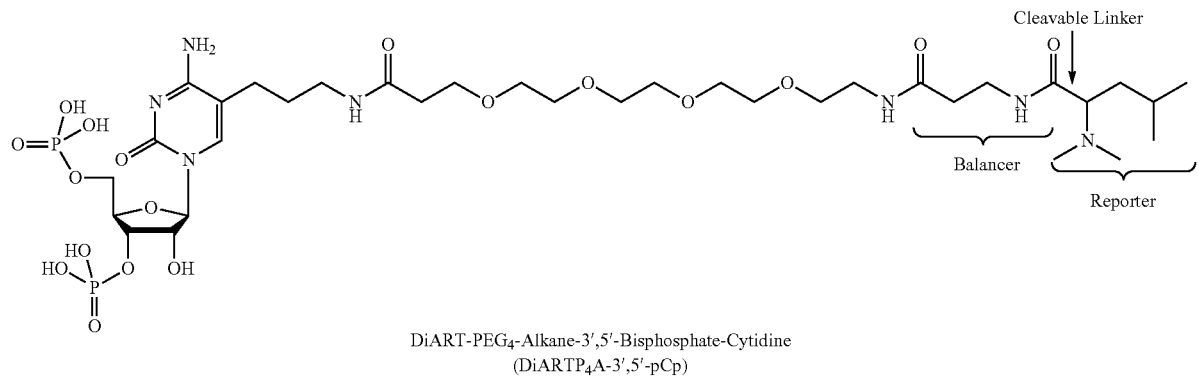

DiART-PEG$_4$-Alkane-3′,5′-Bisphosphate-Cytidine
(DiARTP$_4$A-3′,5′-pCp)

Examples of compounds with a spin label include, but are not limited to, the following:

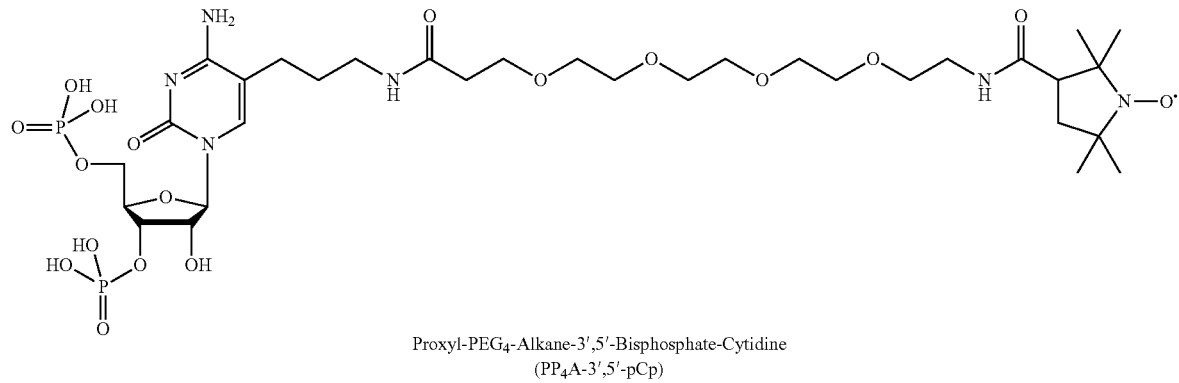

Proxyl-PEG$_4$-Alkane-3′,5′-Bisphosphate-Cytidine
(PP$_4$A-3′,5′-pCp)

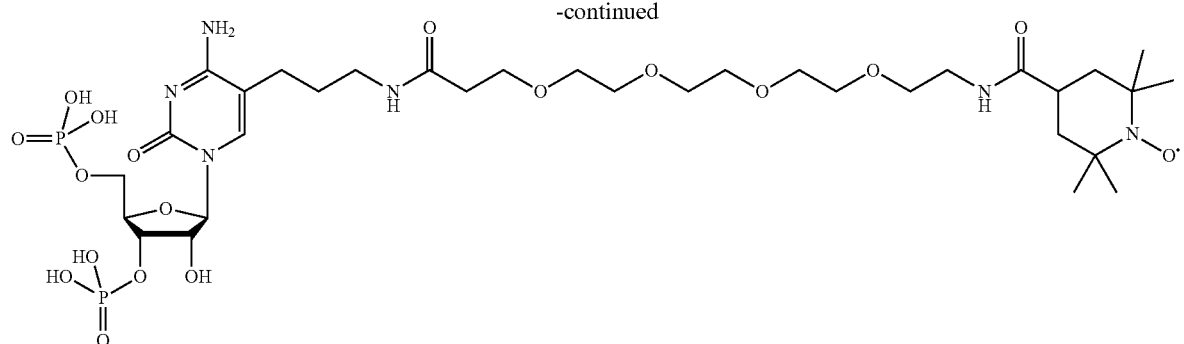
TEMPO-PEG₄-Alkane-3′,5′-Bisphosphate-Cytidine
(TP₄A-3′,5′-pCp)
An example of a desthiobiotin-containing compound is:
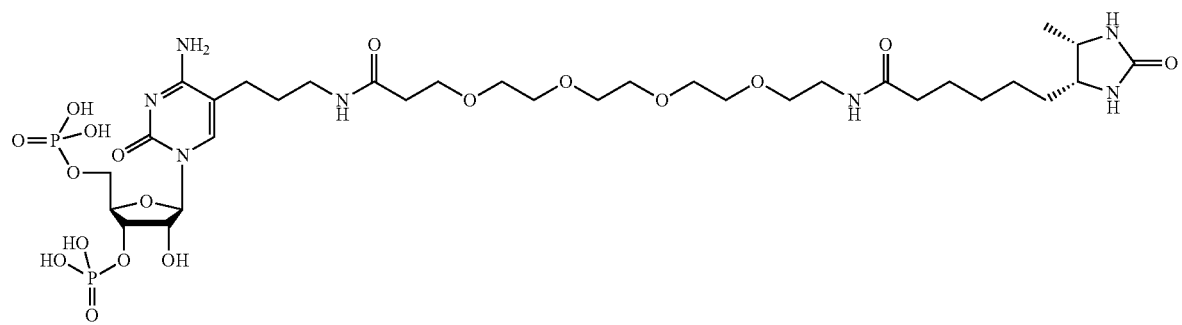
Desthiobiotin-PEG₄-Alkane-3′,5′-Bisphosphate-Cytidine
(DP₄A-3′,5′-pCp)
Examples of compounds with alternative cleavage include, but are not limited to, the following:
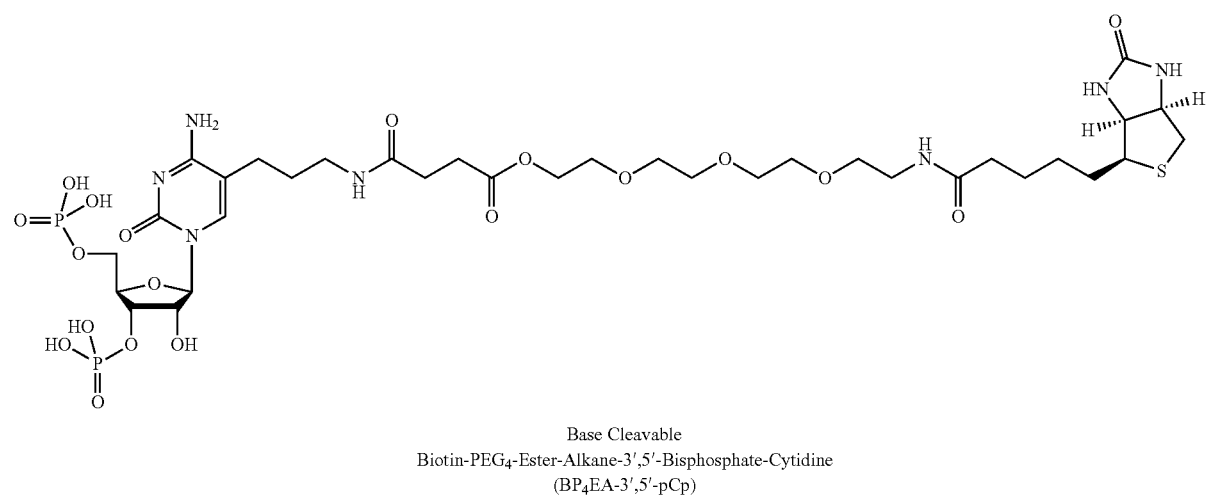
Base Cleavable
Biotin-PEG₄-Ester-Alkane-3′,5′-Bisphosphate-Cytidine
(BP₄EA-3′,5′-pCp)

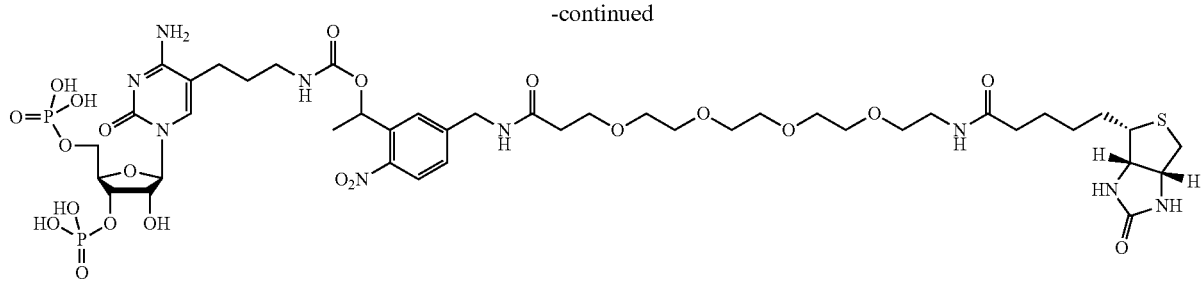

Photocleavable
Biotin-PEG$_4$-Ester-Alkane-3',5'-Bisphosphate-Cytidine
(BP$_4$EA-3',5'-pCp)

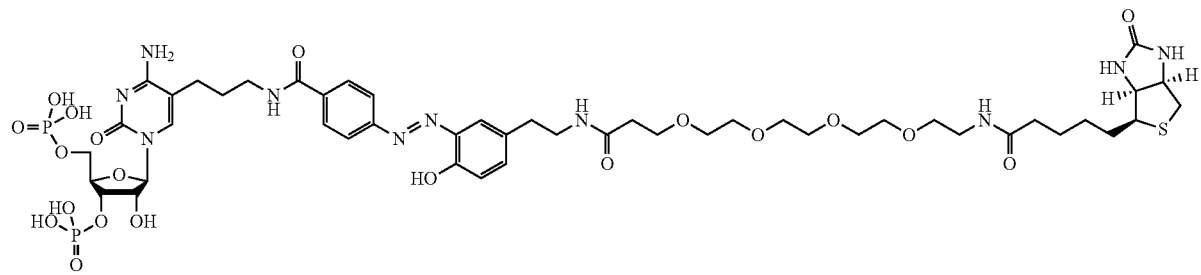

Reduction Cleavable
Biotin-PEG$_4$-Ester-Alkane-3',5'-Bisphosphate-Cytidine
(BP$_4$EA-3',5'-pCp)

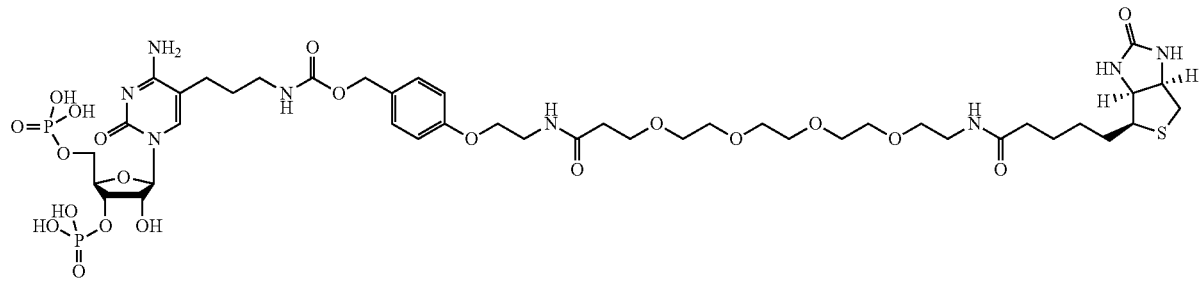

Acid Cleavable
Biotin-PEG$_4$-Ester-Alkane-3',5'-Bisphosphate-Cytidine
(BP$_4$EA-3',5'-pCp)

One embodiment is a kit to label RNA with the compound described above. In one embodiment, the kit contains the compound(s), ligase, ligase buffer, and labeling instructions. In one embodiment, the kit contains additional kit components to enhance ligation efficiency including polyethylene glycol as a size exclusion reagent and DMSO to relax secondary structure. In one embodiment, the kit also includes a control RNA that ligates with greater than 75% efficiency, and a synthetic biotinylated RNA control to assess ligation efficiency. Instructions include methods for a typical ligation reaction using the reagents listed and/or instructions for using a nucleic acid comprising the labeled nucleotide in a method, such as mobility shift, Northern blot, pull-down assay, or in situ hybridization. In one embodiment, the kit contains a described compound where the sugar is ribose, the purine or pyrimidine base is C, m is 3, Lnk is

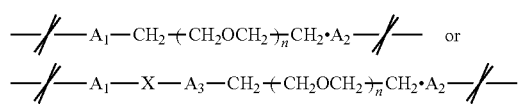

n is 4, A$_1$ is

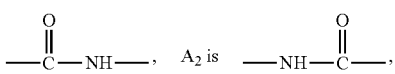

and when present, A$_3$

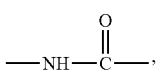

and Obs is selected from the group consisting of biotin, a fluorophore, and an azide.

For mobility shift assays, an excess of the labeled RNA was incubated with a solution containing the protein, RNA, or DNA of interest in an optimized binding buffer. The incubation conditions were empirically determined; incubation time typically ranged from 5 minutes to 1 hour, incubation temperatures typically ranged from 4° C. to room temperature (19° C. to 22° C.). The binding reaction was then subjected to electrophoresis to separate RNA binding complexes from free probe. The shifted RNA complex was then detected in-gel, or transferred to a positively charged membrane and detected using secondary detection reagents (i.e., with a chromogen, or by chemiluminescence).

For Northern blotting, the labeled RNA was used for the detection of RNA that had been separated by electrophoresis and transferred onto a membrane. The labeled RNA was denatured for 5-10 minutes at 95° C. and quickly cooled on ice to less than 10° C. The denatured probe was then added to an optimized hybridization solution and incubated with the membrane at an empirically determined temperature for at least 1 hour, but up to overnight. The membrane was then washed and RNA was detected using secondary detection reagents (i.e., chromogen, by chemiluminescence).

For an assay using a labeled RNA to enrich for a component, whether the substance containing the component was bound to a chip, resin, etc. (e.g., a "pull-down" assay), labeled RNA was incubated in a binding reaction containing the protein, RNA, or DNA of interest, an optimized binding buffer, and affinity resin. The resin was then washed, the RNA complex was eluted, and the protein, DNA, or RNA of interest was detected using techniques including but not limited to PCR, RT-PCR, Western blot, or microarray.

For in situ hybridization, the labeled RNA is used as a probe for the detection of the RNA or RNA complex of interest in cells. The labeled RNA may be used after cells have been fixed onto a support (i.e., a microscope slide, coverslip, tissue dish, microwell, etc.), or in suspension for flow cytometric analysis. Similarly, the labeled RNA may be transfected into live cells, and detected directly or using secondary reagents. The RNA or RNA complex is visualized using techniques including but not limited to light or fluorescent microscopy, flow cytometric analysis, or microarray.

Figure 1:
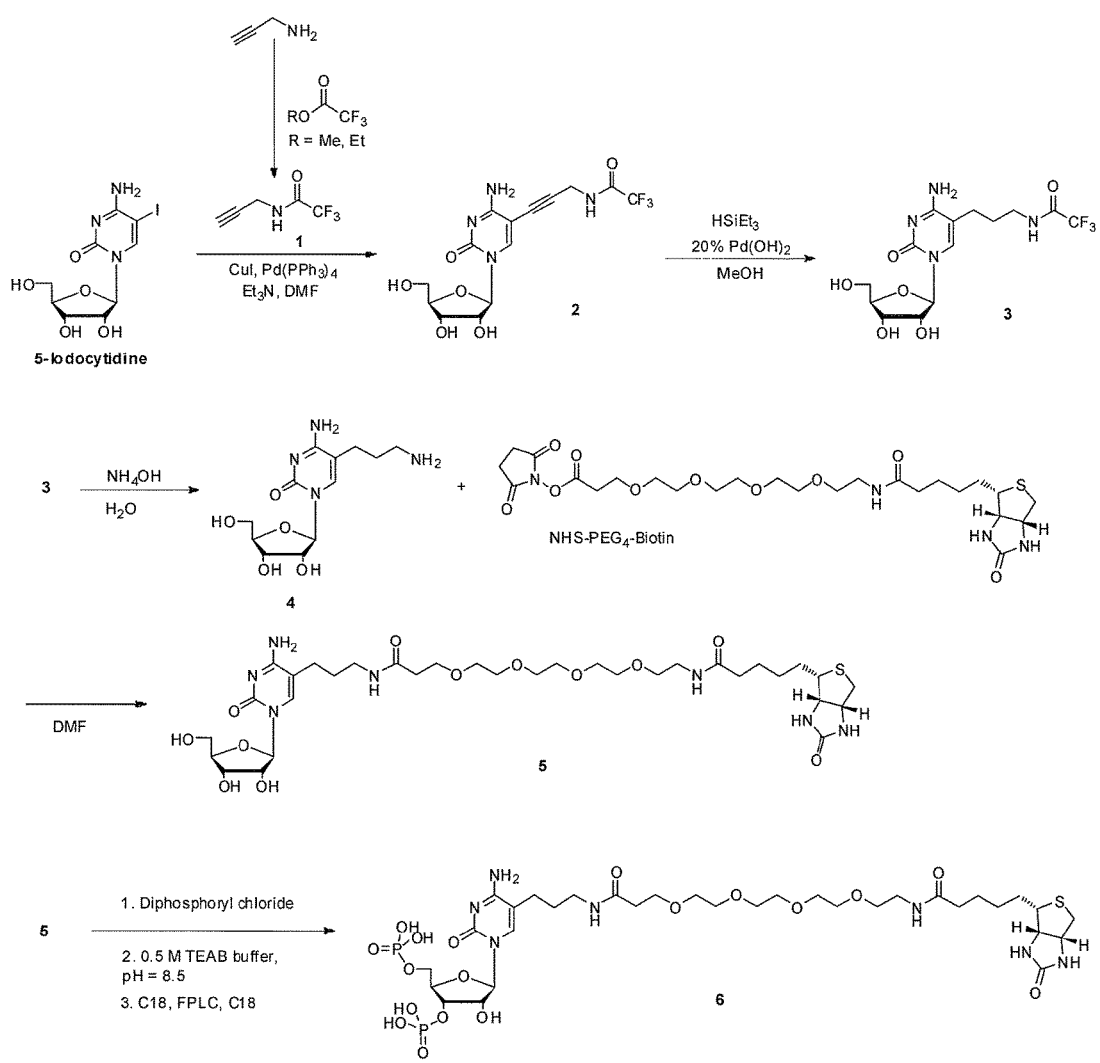
FIG. 1 shows synthesis of biotin-polyethylene glycol (PEG)-alkane-3',5'-cytidine bisphosphate.
Figure 2:
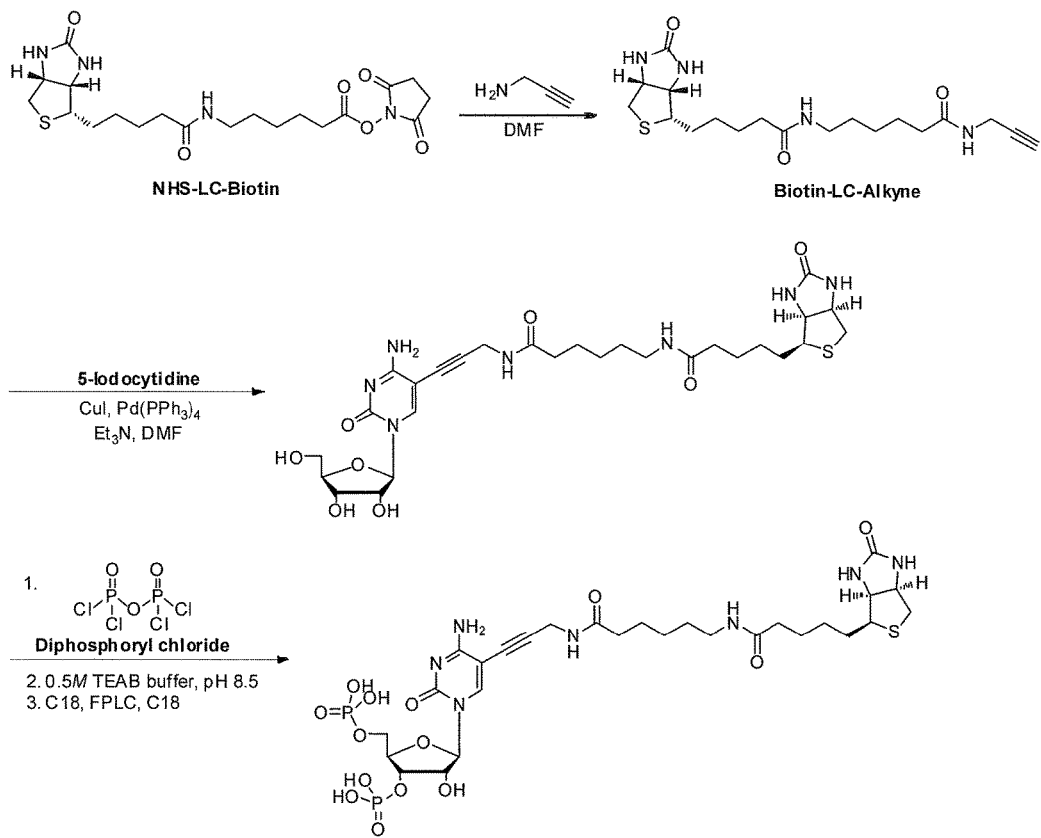
FIG. 2 shows synthesis of biotin-linker-alkyne-3', 5' cytidine bisphosphate.
Figure 3:
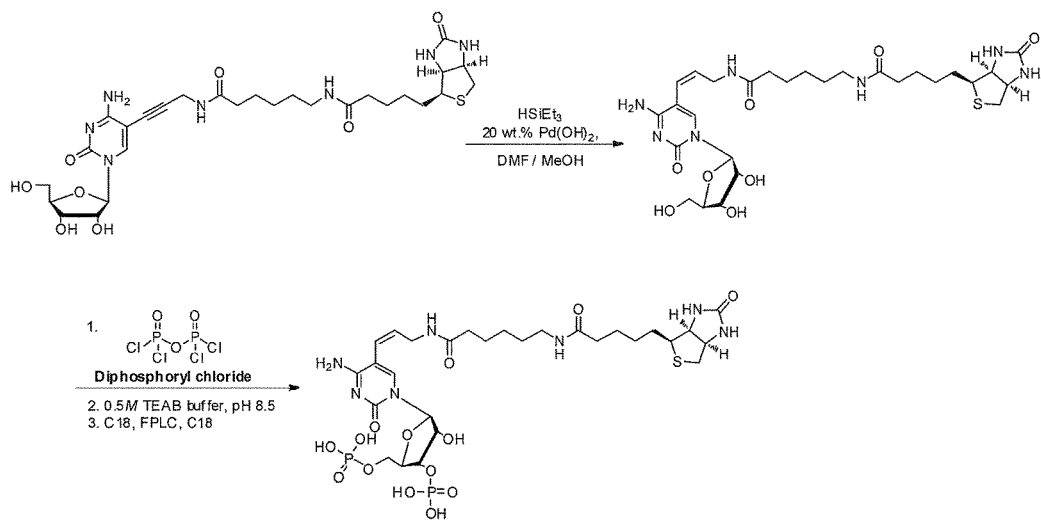
FIG. 3 shows synthesis of biotin-linker-alkene 3', 5' cytidine bisphosphate.
Figure 4:
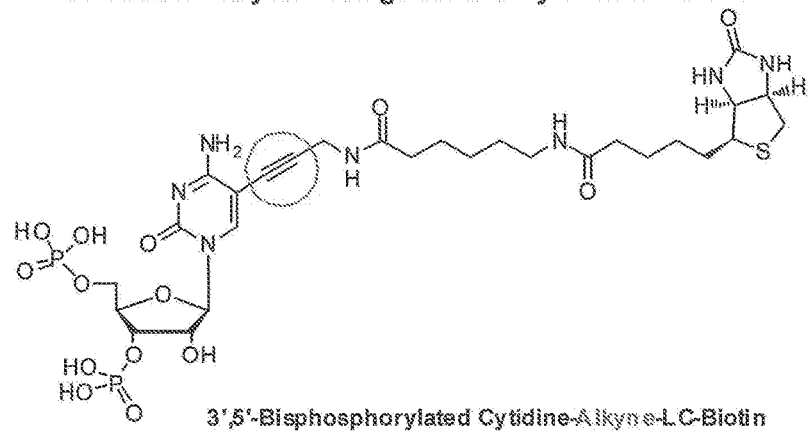
FIG. 4 shows functionality of a modified nucleotide containing an alkyne linkage and representative electrophoretic gels A, B, and C.
Figure 4:
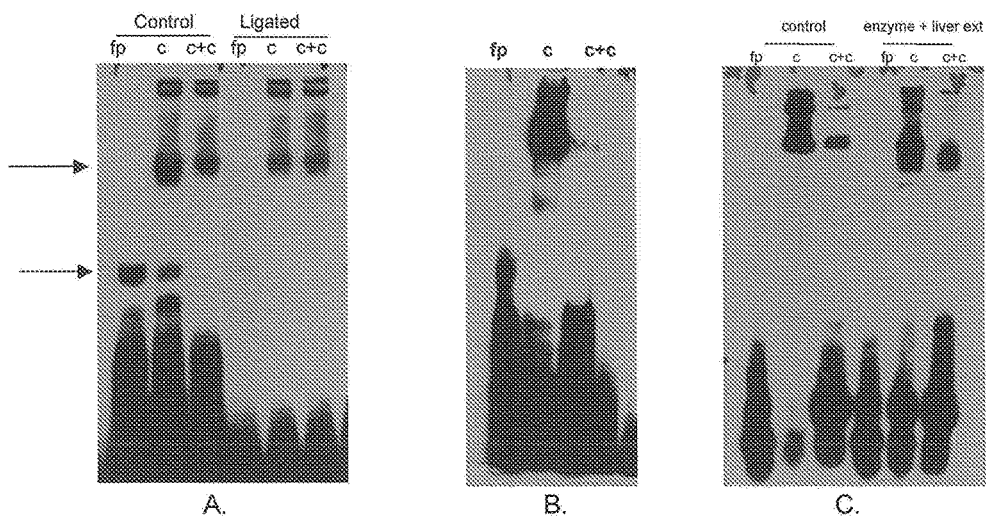
Figure 5:
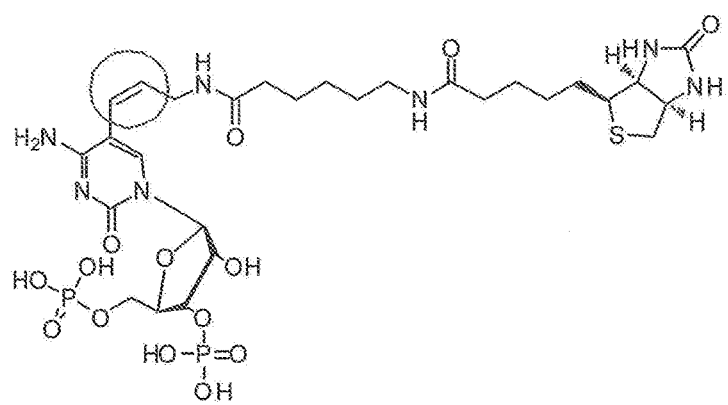
FIG. 5 shows functionality of a modified nucleotide containing an alkene linkage.
Figure 5:
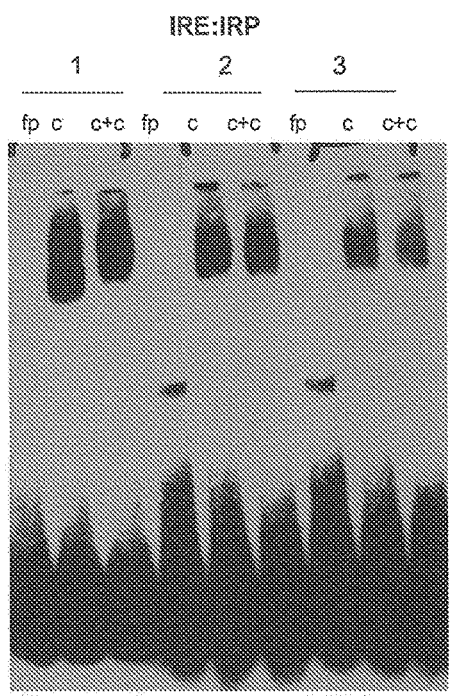
Figure 6:
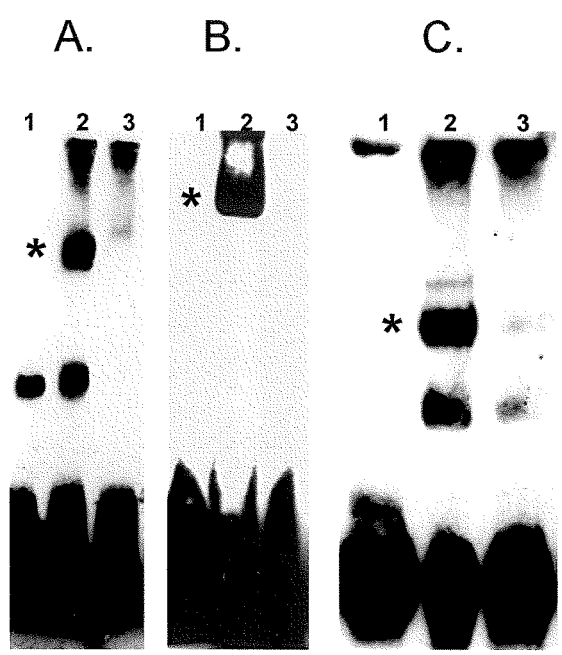
FIG. 6 shows functionality of a modified nucleotide containing an alkane linkage.

In the experiments subsequently described, T4 RNA ligase was used to label RNA with biotinylated cytidine 3',5' bisphosphate. Several molecules were synthesized to optimize the nucleotide for optimal ligation efficiency and functionality, for example, preservation of the interaction of the labeled RNA with other RNA or cellular proteins. Three different alkyl linkages were tested, including alkyne, alkene, and alkane, in combination with both LC (long chain), SC (short chain), and PEG spacers, as shown in FIGS. 1-3. The molecules were tested for ligation efficiency and functionality utilizing established electrophoretic mobility shift (EMSA) controls. In a mobility shift assay, labeled RNA probe is incubated with a cell lysate containing the protein(s) of interest in a binding reaction. The reaction is then electrophoresed on a non-denaturing gel. Unbound probe will migrate to the bottom of the gel, while protein bound probe will migrate more slowly, resulting in a bandshift. The alkyne-LC- and alkyne-SC-containing nucleotides ligated with good efficiency; however, the alkyne linkage was reactive in cell lysates. In a purified system using an RNA polymerase template and purified RNA polymerase, the alkyne compounds produced a functional gel shift (FIG. 4A, electrophoretic gel), while the alkyne compound did not produce a functional gel shift with the iron responsive element (IRE)-iron responsive protein (IRP) control utilizing cytosolic liver extract (FIG. 4, electrophoretic gel B). When the liver extract was mixed with purified RNA polymerase, the bandshift was affected, suggesting that the alkyne compound is reactive with liver extract (FIG. 4, electrophoretic gel C). Similar results were obtained with the alkene compounds, where the IRE-IRP control ligated, but did not produce a functional bandshift (FIG. 5). The nucleotide containing the alkane linkage and PEG spacer was the most optimal compound for both ligation efficiency and functionality (FIG. 6).

Utilizing the biotin-PEG4-alkane 3,5 cytidine bisphosphate molecule, optimal ligation conditions were determined. The conditions described resulted in ligation efficiencies greater than 70%, and in some cases greater than 90%, depending upon the RNA secondary structure and ligation conditions. A standard reaction had a donor to acceptor ligation ratio of greater than 20:1. The reaction buffer contained 20U to 40U T4 RNA ligase, 40U RNase inhibitor, 50 mM Tris-HCl, 10 mM MgCl$_2$, 10 mM DTT, 1 mM ATP (pH 7.8 at 25° C.), and 15% polyethylene glycol (PEG, MW 20,000). To achieve ligation efficiencies greater than 70%, reactions were incubated at 37° C. for 30 minutes, or at 16° C. from 30 minutes to 24 hours, depending upon the RNA length and secondary structure. In one embodiment, reactions contained 25 pmol to 50 pmol RNA, 1 nmol biotinylated nucleotide, and 20U to 40 units of T4 RNA ligase in a 30 μl reaction volume. An excess of biotinylated nucleotide did not affect ligation efficiencies, and a range 1 pmol RNA to 200 pmol of RNA was tested in the ligation reaction. The concentration of PEG ranged from 5% to 20%.

As shown in the table below, the ligation conditions were assessed utilizing several RNA species, ranging in length, complexity, and function to demonstrate efficiency of ligation reaction using RNA of varying complexity and length. RNA was derived from the 3' untranslated regions (UTR) of mRNA 28-42 nucleotides, miRNA (22-80 nucleotides), and catalytic RNA (451 nucleotides). RNA was derived synthetically, or from in vitro transcription reactions.

| | Description | RNA source | Length (bases) | Optimal reaction conditions |
|---|---|---|---|---|
| IRE (iron responsive element) | 5' or 3' UTR element | synthetic | 28 | 2 hrs 16 C |
| RNA polymerase template RNA | RNA | synthetic | 42 | 30 minutes, 37° C. >1 hr 16° C. |
| mir-16-1 | mature micro RNA | synthetic | 22 | ON 16° C. |
| TNF ARE | 3' UTR element | synthetic | 37 | 2 hrs 16° C. |
| Let-7 | pre-miRNA | in vitro transcribed | ~70 | overnight 16° C. |
| hTR | catalytic RNA | in vitro transcribed | 451 | overnight 16° C. |
| COX-76 ARE | 3' UTR element | in vitro transcribed | ~70 | overnight 16° C. |
| mir-16-1 | pre-miRNA | in vitro transcribed | ~70 | overnight 16° C. |

Ligation efficiencies were greater than 70% with reactions using 25-50 pmol RNA, 1 nmol biotinylated nucleotide, 20-40U T4 RNA ligase, 40U RNase Inhibitor, 50 mM Tris-HCl, 10 mM MgCl$_2$, 10 mM DTT, 1 mM ATP (pH 7.8 at 25° C.), and 15% PEG (MW 20,000). Ligation efficiencies were improved for RNAs with extensive RNA secondary structure or length by heating briefly before the ligation reaction; heating temperatures ranged from 80° C.–90° C. for 1-5 minutes, followed by rapid-cooling on ice for at least 1 minute to several hours. In some cases, adding 25% DMSO before heating enhanced ligation efficiency. The order of addition of the reaction components did not matter, except for the PEG, which was added last. Several PEG varieties were tested including molecular weights of 1500, 6000, 8500, and 20,000. Although the PEG (MW 20,000)

best enhanced ligation efficiency, the other PEG molecules were acceptable, and other size exclusion molecules would also be acceptable. A PEG concentration of 15% was optimal. Other PEG concentrations could also be used, ranging from 5% to 20%.

Ligation efficiencies were assessed using dot blot and quantitative spot densitometry. A synthetically biotinylated RNA was used as a control where 100% biotinylation was assumed. Labeled RNA from the ligation reaction and the synthetically labeled RNA were first normalized to concentration, and then serially diluted to determine efficiency. A small volume was applied (spotted) onto a positively charged nylon membrane. The membrane was cross-linked using ultraviolet (UV) radiation. Biotinylated RNA was detected using a streptavidin horseradish peroxidase (HRP) substrate and chemiluminescent detection. The non-saturating spots, which are spots where the densitometry intensity value was not saturated, were quantitated using densitometry. To determine ligation efficiency, labeled RNA was compared to the control standard to determine efficiency. To determine labeling reproducibility, samples were applied (spotted) in triplicate for two of the RNA samples for intra-assay variability, and each ligation with the optimized conditions was repeated at least three independent times for interassay variability. To determine labeling integrity, labeled RNA was separated by electrophoresis on a gel containing 5% acrylamide/8 M urea (denaturing gel), the RNA was transferred to a nylon membrane and was detected using chemiluminescence. The results indicated that the labeled probes were of high quality, of the correct size, and exhibited either minimal degradation or no degradation.

In vitro transcribed RNA was derived through transcription from a digested plasmid containing the sequence of interest flanked by a T7 polymerase binding site and restriction enzyme site such that only the RNA of interest is transcribed. In vitro transcribed RNA was also derived through transcription of complementary primers containing a T7 RNA polymerase binding sequence element. Digested plasmid was purified by extraction with phenol:chloroform and ethanol precipitation. Complementary primers were annealed in a reaction containing 25 μM of each primer in 10 mM HEPES buffer (pH 7.3). Reactions were incubated at 95° C. for ten minutes followed by slow cooling at room temperature for at least ten minutes, followed by incubation on ice. Transcription reactions typically contained 500 ng-1 μg DNA, 0.5 mM each of ATP, CTP, UTP, and GTP, 1× transcription buffer, 30U T7 RNA polymerase, and 40 units RNAse inhibitor. Reactions were incubated for 30 minutes to 1 hour at 37° C. DNA was digested for ten minutes with RNAse-free DNAse I at 37° C., followed by inactivation with EDTA. RNA was then selectively precipitated with ethanol, and transcript purity was determined by either agarose or non-denaturing polyacrylamide gel electrophoresis. Precipitated RNA was then quantitated by UV-spectroscopy (absorbance at 260 nm/280 nm), and 25 pmol-50 pmol of RNA was used in each ligation reaction.

The functionality of the labeled RNA was determined by assaying a known interaction of the RNA to ensure that the 3'-end label minimally disturbed secondary structure. Functionality of labeled iron responsive element (IRE), RNA polymerase template, and let-7 micro RNA was determined by RNA electrophoretic mobility shift assay (EMSA). The protein sources included cytosolic liver extract containing iron responsive element-iron responsive protein (IRE-IRP), lin-28 overexpression lysate (let-7-lin28), and purified RNA core polymerase (Epicentre). Dilutions of each RNA (nM) were incubated with the protein of interest in a 1× binding reaction containing 10 mM HEPES (pH 7.3), 20 mM KCl, 1 mM $MgCl_2$, 1 mM DTT, 2.5-10 μg tRNA, and 5% glycerol for 15-30 minutes at room temperature (about 20° C. to about 22° C.). Optimal binding conditions were achieved for RNA polymerase template by substituting tRNA with bovine serum albumin (BSA), and increasing the DTT concentration to 3 mM and the KCl concentration to 40 mM for the let-7-lin28 interaction. Binding reactions composition were separated by electrophoresis on native 6% acrylamide DNA retardation gels for one hr, 100 V, at either room temperature or 4° C. The RNA was then transferred to a positively charged nylon membrane, cross-linked (UV irradiation), and then detected using chemiluminescence. Three binding reactions were assessed for each labeled RNA: 1) migration and intensity of the free probe that migrated toward the bottom of the gel; 2) intensity of the labeled RNA with protein, resulting in a bandshift of the RNA-protein complex; and 3) the competition reaction of the labeled RNA and the unlabeled RNA with protein (FIG. 6). Each bandshift reaction was repeated three times with three independently labeled RNAs. Each of the 3 end-labeled probes was able to functionally bind its respective proteins and produce a robust bandshift, as shown for RNA template-RNA polymerase interaction (FIG. 6A), IRE-IRP interaction (FIG. 6B), and let-7-lin28 interaction (FIG. 6C). Each probe was also functional at the nanomolar level, indicating that the 50 pmol labeling reaction was sufficient for EMSA studies.

In one embodiment, biotin or other suitable moiety, known by one skilled in the art, on the labeled nucleotide serves as an affinity handle for isolating RNA:protein complexes. The functionality of a described biotin-labeled RNA to serve as an affinity handle for isolating RNA complexes (containing RNA, DNA, RNA and DNA, or protein) using an affinity resin, bead, or sensor chip (e.g., pull-down) was determined using streptavidin agarose resin and surface plasmon resonance.

Figure 7:
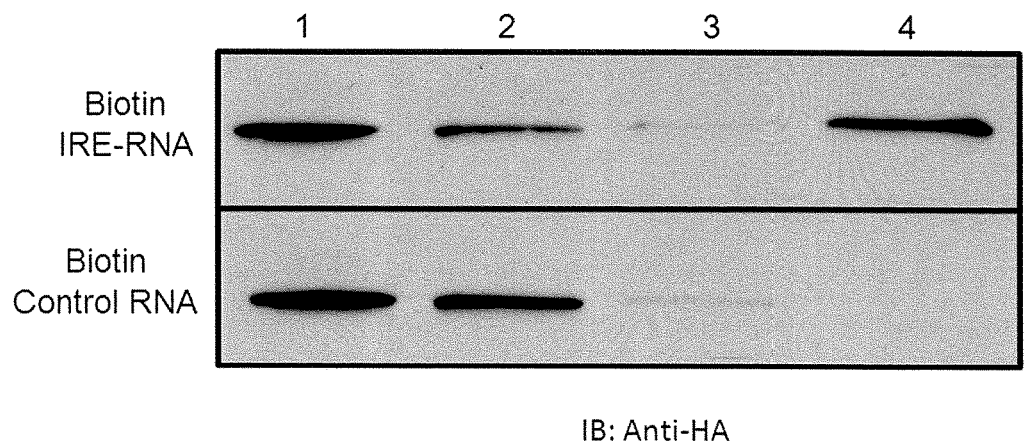
FIG. 7 shows functionality of a modified nucleotide containing an alkane linkage.

IRE-RNA (SEQ ID NO: 1) was labeled using biotinylated cytidine bisphosphate, and T4 RNA ligase. The IRP protein, which binds IRE RNA sequences, was cloned into a vector containing an HA tag and in vitro translated using an human cell-free human in vitro transcription/translation system. Before incubation with the biotinylated RNA, the IRP lysate was incubated with streptavidin agarose resin to reduce non-specific binding, and to remove endogenous biotin. The IRP lysate was then incubated with the labeled IRE, or with a non-specific control RNA (SEQ ID NO: 2) which was 3'-labeled with biotin, in binding buffer (10 mM HEPES pH 7.3, 20 mM KCl, 1 mM $MgCl_2$, 1 mM DTT, 10% glycerol, 40U RNase inhibitor (RNasin®)) for 30 minutes at room temperature, and was then cross-linked with UV light (254 nm) for 10 minutes on ice. Binding reactions were then washed with PBS and the IRE-IRP complex was eluted from the resin. After separation by electrophoresis and transfer to a membrane, IRP was detected using mouse anti-HA antibody. The results are shown in FIG. 7. Lane 1 is 5 μl HA-IRP IVT lysate, lane 2 is 25 μl flow-through fraction, lane 3 is 50 Cl wash fraction, and lane 4 is 25 μl eluted fraction.

Figure 8:
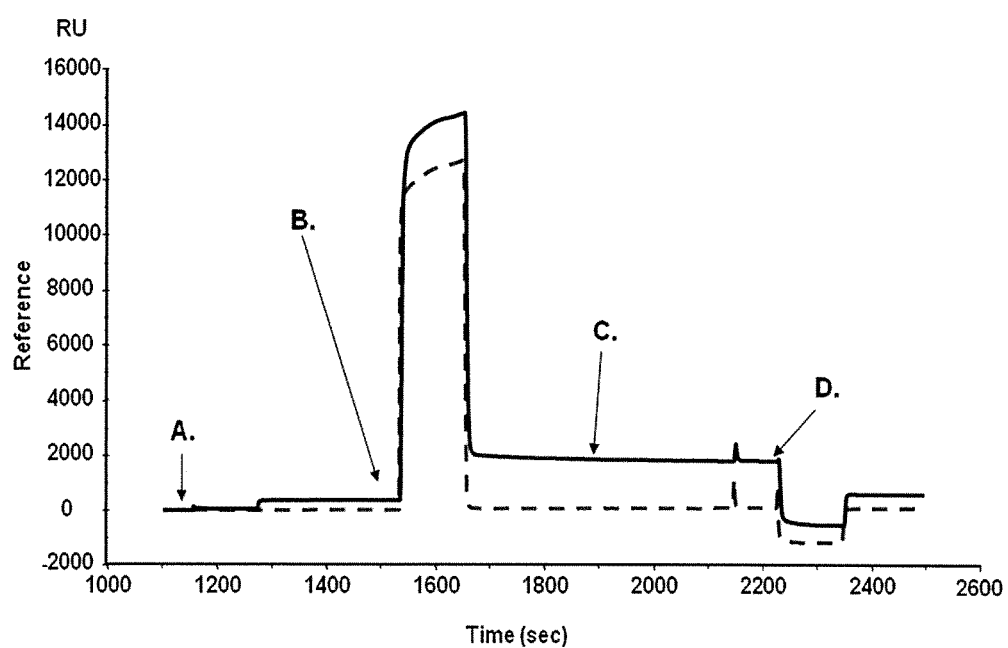
FIG. 8 shows functionality of a modified nucleotide containing an alkane linkage.

The ability of the biotin-labeled RNA to enrich for RNA:protein complexes using an immobilized streptavidin sensor chip was examined using Biacore™ Surface Plasmon Resonance (SPR). The results are shown in FIG. 8 where the solid line is control mRNA and the dashed line is a reference (flow cell 1); and where A=biotinylated RNA template control loading; B=RNA Pol II injection; C=RNA Pol II bound to control RNA; and D=injection of unlabeled control RNA. Biotin-labeled control RNA was captured on a Streptavidin-coated sensor chip followed by injection of bacterial RNA Polymerase. A binding response of RNA polymerase II was detected on the active RNA surface and specificity was confirmed by the loss of binding after injection of non-labeled control RNA. Twenty pmol labeled RNA was diluted into nuclease-free HEPES buffer (pH 7.3), injected at 5 l/min for four minutes, and captured onto a commercially purchased streptavidin-coated sensor chip for the Biacore 3000®. Bacterial RNA polymerase (0.1 U/µl) was then injected for two minutes. As shown in FIG. 8, a binding response of RNA polymerase II was detected on the active RNA surface and specificity was confirmed by loss of binding after injecting non-labeled control RNA. Specificity was determined through competition of binding RNA polymerase with a 50-100 fold excess of non-labeled RNA polymerase template RNA that was injected for four minutes.

One embodiment is a method to assay RNA using an RNA probe labeled with the compound described above and using the method described above. The labeled RNA can be synthesized as described above. The labeled RNA probe is contacted with the sample to be assayed under conditions to permit the labeled RNA to hybridize with RNA in the sample and to detect the hybridization in an assay, e.g., mobility shift, Northern blot, in situ hybridization, pull-down assay, etc. using, e.g., a streptavidin-conjugated reporter molecule such as an enzyme, a fluorescent compound, an isotope, a gold particle, etc.

Current enrichment and detection of RNA-protein interactions are limited by inefficient enrichment and release of the RNA-protein complex without disruption the interaction. Nucleotides modified with at least one moiety or affinity label, e.g., biotin, enriched for and enhanced detection of protein interactions. Kits containing such modified nucleotides, such as labeling kits that attach a label (e.g., fluorogenic substrate) to a nucleotide of interest and resulting in a labeled nucleotide probe, kits to isolate nucleotide binding proteins, and kits to add a crosslinker or another functionality, are also disclosed. Methods of synthesizing such modified nucleotides are also disclosed.

Enrichment efficiency was improved using labeled RNA as bait for the RNA-protein complex. In one embodiment, the RNA was 3'-end labeled with a modified cytidine-3',5'-bisphosphate containing a spacer arm with an affinity handle using T4 RNA ligase. One affinity handle was desthiobiotin. One affinity handle was biotin. Different spacer lengths and compositions maximized accessibility of the RNA to the protein once attached to a surface (e.g., bead) without compromising secondary structure. Enrichment efficiency of the RNA-protein complex was assessed using RNA:protein interactions known to one skilled in this art, including miRNA:Argonaute 2, poly A RNA:PolyA binding protein, and SNRNPA/U1 RNA. In one embodiment, endogenous RNA binding proteins were obtained from cell lysates or expressed in human in vitro translated cell lysates. Non-specific binding was determined by incubation of lysate with beads only, or with an unrelated labeled RNA. Elution with biotin allowed for more flexibility for further downstream applications, e.g., mass spectrometry. The method enriched for additional proteins in the binding complex, evidenced by isolation of higher molecular weight complexes of miRNA:Argonaute detected by Western blot.

Isolation of RNA protein interactions is limited by the tools used for isolation and the inefficiency associated with the enrichment and elution of the complex. Multiple approaches and tools are necessary to capture both the protein and RNA in the complexes. Both antibody and labeled RNA as bait are currently used for enrichment of the RNA binding protein complexes. These enrichment procedures have been further modified for in vivo use, such as using incorporation of 4-thio-uridine for in vivo crosslinking before capture of the complex with antibody.

Attachment of the handle or detector to the modified nucleotide using a (poly)ethylene glycol (PEG) spacer was determined to be optimal for minimal interference with the RNA protein interaction and detection (U.S. Published Patent Application No. 2011/0262917). The disclosed method and kits further streamlines chemical synthesis of the modified nucleotide, such that the azide-$PEG_{(n)}$-alkane cytidine intermediate serves as an affinity handle, or accommodates the addition of a variety of handles and detectors after reduction using NHS conjugation. In one embodiment, the PEG spacer is further modified for additional applications.

Figure 9:
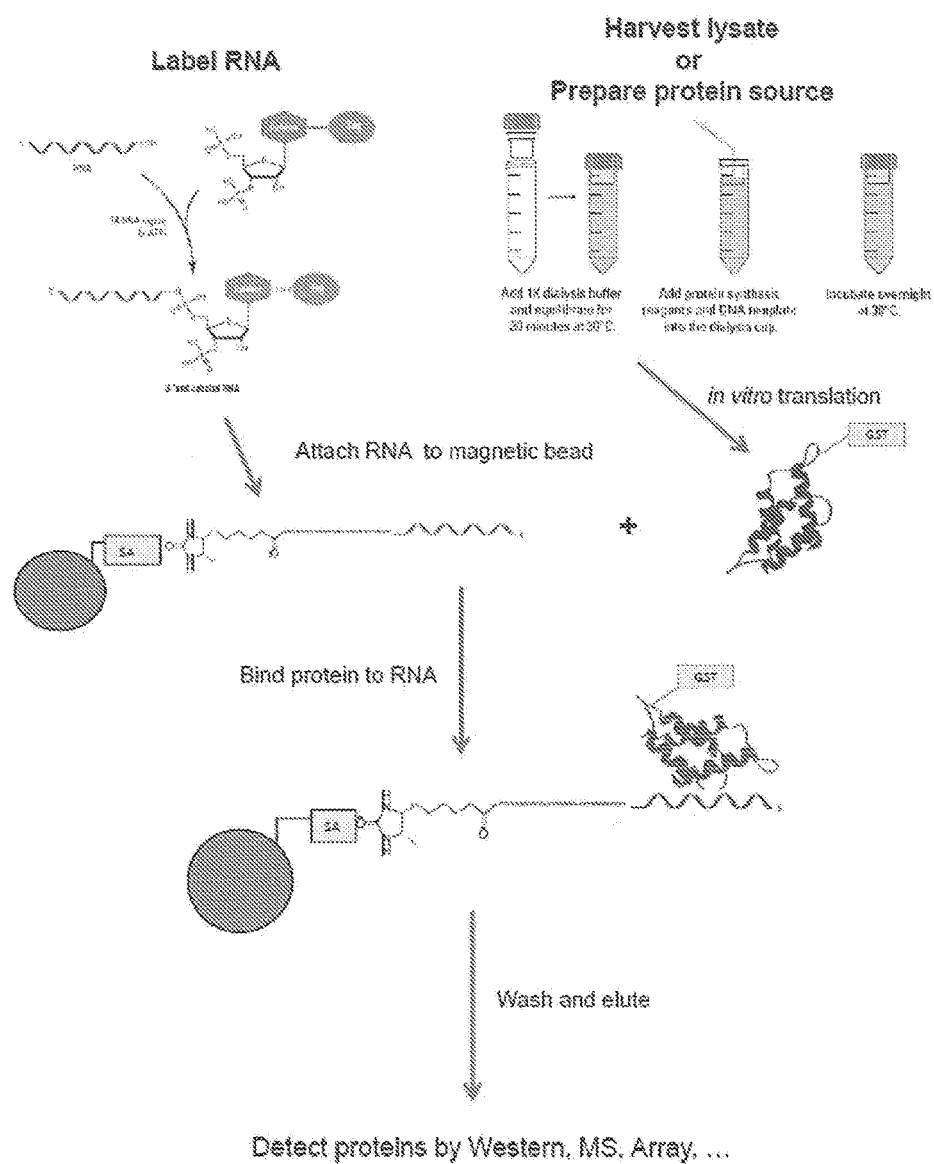
FIG. 9 schematically shows enrichment of RNA binding proteins using labeled RNA as bait.

FIG. 9 shows enrichment of RNA binding proteins using labeled RNA as bait. Tools for isolation of RNA-protein interactions include, in one embodiment, 3'-end labeling RNA with a modified cytidine using T4 RNA ligase. Addition of a single label minimized interference with the RNA-protein complex. Additional labeling kits permits flexibility of label choice, and labeling of RNA that cannot be made synthetically.

FIGS. 10, 11, and 12 show synthesis of, respectively, azide-$PEG_{(n)}$-alkane cytidine intermediate, synthesis of R-$PEG_{(n)}$-alkane-3',5'-bisphosphate cytidine, and two RNA pull down labeling reagents.

Optimization for efficient labeling and capture of the RNA protein complex was effecting by labeling synthetic RNA and preparing overexpression lysates using a human in vitro translation system, as shown in FIG. 13. Synthetic RNA (50 pmol/reaction) was end-labeled using a twenty=fold excess of biotin-$PEG_{12}$-alkane-3',5'-bisphosphate cytidine with T4 ligase. Labeled RNA was incubated with 0.5 mg of streptavidin magnetic beads for thirty minutes at room temperature. Beads were then washed 2× in 20 mM Tris (pH 7.5). PABPC1-GST and SNRPA1-GST proteins were expressed using a high yield cell-free human in vitro translation system. Lysates were diluted 1:10 in binding buffer before use. For the binding reaction, proteins were incubated with RNA-containing beads (both positive and negative controls), or base beads in 1× binding buffer (PABPC1-10 mM Tris (pH 7.5), 2.5 mM $MgCl_2$, 1-mM KCl, 15% glycerol, 0.5% Tween-20, 10 µg tRNA; SNRPA1-10 mM Tris (pH 7.5), 250 mM NaCl, 1 mM EDTA, 0.5% Tween-20, and 10 µg tRNA) for one hour at 4° C. Beads were washed 3× in 20 mM Tris (pH 7.5), 10 mM NaCl, 0.5 Tween-20. Complexes were eluted using 2× reducing sample buffer. Normalized samples were separated by electrophoresis, transferred, and detected using PABPC1, GST (SNRPA1) antibodies (1:10000 dilution in TBST-0.5% BSA). Exposure time—1 minute. FT-flow through; 1,2,3-washes, E elution. Expression vector and RNA sequences are indicated in FIG. 13.

RNA was labeled with biotin and desthiobiotin. Non-limiting examples include Poly(A) RNA and U1 RNA with Poly(A) binding protein and SNRPA1, respectively, and Poly(A) binding protein using endogenous HEK 293 lysate. Capture using end-labeled RNA effectively captured RNA binding proteins.

In one embodiment, the disclosed modified nucleotides label an RNA molecule to result in a labeled RNA probe. The labeled RNA probe is then used, e.g., in pull-down assays to isolate RNA-complexes containing RNA, DNA, RNA and DNA, and/or protein e.g., RNA-binding proteins.

In contrast to the disclosed method, previous methods to isolate RNA/RNA-binding protein complexes have used either the protein component of the complex or the DNA component of the complex, instead of the RNA component of the complex, as the capturing moiety or bait. As one example, U.S. Pat. Nos. 6,635,422 and 7,504,210 disclose use of proteins (antibodies to the RNA-binding protein of the RNA/protein complex) to isolate endogenously formed complexes. Subsequently, the complexed RNA was identified and used to create a gene expression profile of mRNA. As another example, WO 01/73115 uses double stranded DNA (dsDNA) as bait to isolate transcription factors and investigate modulators of transcription factor binding.

In contrast to methods using protein or DNA, the disclosed methods use a modified nucleotide that is a single-stranded labeled RNA as bait in various methods, e.g., to isolate RNA-binding proteins.

In one embodiment, the modified nucleotides have the following general structure (I):

$$\begin{array}{c}P1\\ \diagdown\\ \phantom{P}\text{Nucleoside (Nus)-Connecting Group (Alk)-Linking Group (Lnk)-}\\ \diagup\\ P2\end{array}$$

Observable Label Moiety (Obs)

The composition can include a salt, conjugate base, tautomer, or ionized form. P1 is a phosphate group. P2 is a phosphate group. Nus is a nucleoside moiety containing a sugar bound to a purine or pyrimidine base. Alk is a connecting group having the structure -//—(CH$_2$)$_m$—Y—//- where Y is a bond or bond forming group selected from

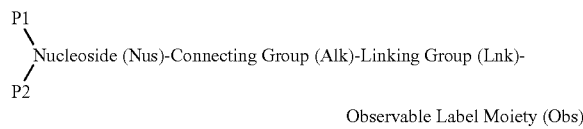

and m is an integer ranging from 3 to 6 inclusive; as shown, the leftmost bond in Alk is to Nus, the rightmost bond in Alk is to Lnk. Lnk is a linking group having the structure

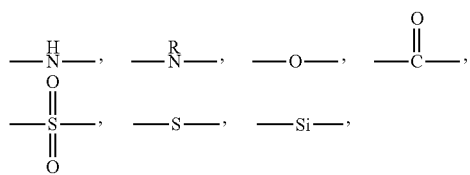

or

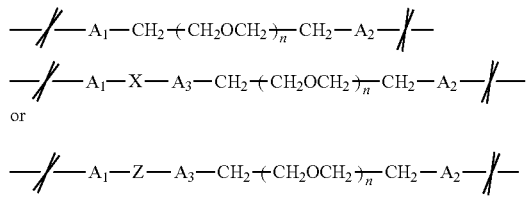

where n is an integer ranging from 2 to 48 inclusive; A$_1$ is a bond forming group selected from

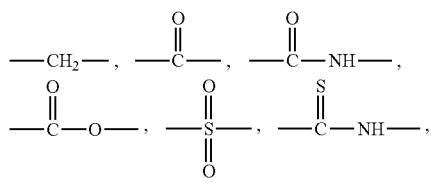

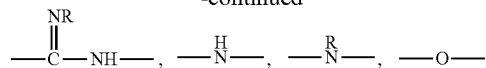

A$_2$ is a bond forming group selected from

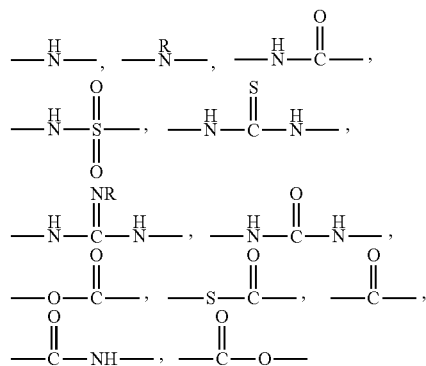

A$_3$, when present, is a bond forming group selected from

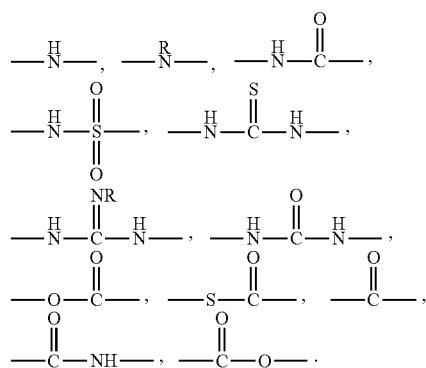

X is a cleavable group that can undergo silicon-carbon cleavage, nucleophilic cleavage, redox cleavage, photochemical cleavage, enzymatic cleavage, or exchange-based cleavage;

Z is a branching group that contains modifying molecule (Mod); Mod is a modifier or modifying molecule (e.g., a crosslinking agent); Obs is an observable label moiety (e.g., an observable label in itself such as a chromogen or fluor, or a molecule that can be rendered observable, a detecting agent; etc.); and the leftmost bond is to Alk and the rightmost bond is to Mod.

Such modified nucleotides, also termed nucleotide analogs, retain biological activity. For example, they are substrates for a variety of DNA and/or RNA polymerases. The modified nucleotide is added to an oligonucleotide or nucleic acid by routine methods, e.g., nick translation, random priming, polymerase chain reaction (PCR), 3'-end labeling, transcribing RNA using SP6, T3, or T7 RNA polymerases, etc.

Modified nucleotides are used to generate labeled probes that may be used in a variety of methods and applications, e.g., biological screening, diagnosis, etc. As one example of use in biological screening, screening an array permits different constituents in a complex sample to be determined. For example, an oligonucleotide probe containing a biotinylated nucleotide specifically binds to analytes in the sample that contain a complementary component, e.g., a nucleic acid or a protein. This yields an observable binding pattern that is detectable upon interrogating the array. When the complementary component is a protein, the protein may bind and/or associate with the labeled probe containing a disclosed modified nucleotide. As another example, an oligonucleotide probe or RNA molecule containing a disclosed biotinylated nucleotide can be used to investigate interactions between the oligonucleotide probe or RNA molecule with RNA-binding proteins, e.g., using the labeled oligonucleotide probe or RNA molecule as bait to capture RNA-binding proteins in a pull-down assay. In one embodiment, elution of the captured protein(s) and/or complex is accomplished by a soft-release, in which the analyte is eluted under mild conditions, e.g., under non-denaturing conditions, at physiological pH, and/or in the absence of detergent. In one embodiment, elution is accomplished by competitive elution where a component or derivative of a binding moiety is added to compete with the capturing agent, for example, by adding biotin to competitively elute a biotin-streptavidin captured complex.

A nucleotide is modified by adding at least one of the following observable label which function as detector and/or capture molecules and derivatives and variant of the moieties, and adding them either directly or indirectly: biotin, desthiobiotin, azide, alkyne, aldehyde, diene, amine, hydrazide, disulfide, fluorophore, spin label, mass tag, etc. known to one skilled in the art. These observable labels, either alone or in combination, are added in various permutations, specific entities, chain lengths, etc. In embodiments, the modified nucleotide contains a polyethylene glycol group (PEG group, also termed a PEG spacer) having the structure —(CH$_2$—O—CH$_2$)$_n$—, where n is an integer from 2 to 48 inclusive. For example, when the modified nucleotide contains four ethylene glycol groups, it is denoted as PEG$_4$ (i.e., n=4).

In one embodiment, the modified nucleotide is biotinylated and has the structure

with PEG having at least 7 carbon atoms and up to 100 carbon atoms, i.e., PEG$_4$ to PEG$_{50}$. In one embodiment, the modified nucleotide is a desthiobiotinylated nucleotide having the formula

In one embodiment, the modified nucleotide is a mass tagged nucleotide having the formula

For any of the disclosed inventive compounds, the compound includes the salt form, conjugate base, tautomer, and/or ionized form. In one embodiment, the modified nucleotide is a ribonucleotide. In one embodiment, the ribonucleotide is cytidine. In one embodiment, the ribonucleotide is adenosine. In one embodiment, the ribonucleotide is uridine. In one embodiment, the ribonucleotide is guanosine. In one embodiment, the ribonucleotide is inosine.

The disclosed modified nucleotide exhibited enhanced ligation efficiency to a nucleic acid over known compounds due to the presence of an alkane linkage. As used herein, a nucleic acid refers to a RNA oligonucleotide, an RNA polynucleotide, a DNA oligonucleotide, or a DNA polynucleotide. The alkane linkage also improved functionality of the modified nucleotide by decreasing reactivity of the modified nucleotide with cell lysates. The PEG spacer increased hydrophilicity of the modified nucleotide to increase accessibility of the biotin for detection and/or capture.

In embodiments that include a crosslinking molecule, the crosslinking molecule is incorporated by incorporation of a branching group Z.

With either ribose or deoxyribose as the sugar, P1 is attached at the 5' position; P2 is attached at the 3' position; and the purine or pyrimidine base is attached at the 1' position.

The purine or pyrimidine base is selected from cytosine (C), uracil (U), adenine (A), thymine (T), guanine (G), or inosine (I) and may be modified or unmodified. Embodiments include, but are not limited to, 1-methyladenine, N$^6$-methyladenine, N$^6$-isopentyladenine, N,N-dimethyladenine, 7-deazaadenine, 2-thiocytosine, 3-methylcytosine, N$^4$-acetylcytosine, 2-thiocytosine, 1-methylguanine, 2-methylguanine, 7-methylguanine, N$_2$,N$_2$-dimethylguanine, 7-deazaguanine, 2-thiouracil, 6-thiopurine, or 2,6-diaminopurine.

In one embodiment, the observable label such as a chromogenic moiety, a fluorophore such as fluorescein, rhodamine, a commercial dye (e.g., DyLight® (Dyomics), Alexa®, Cy3, Cy5), a mass tag, such as a commercial mass tag (e.g., Thermo Fisher Tandem Mass Tag (TMT)), a spin label, or a moiety capable of binding an observable label. In one embodiment, the observable label is a molecule capable of binding or being captured by a corresponding binding partner, such as a streptavidin-binding label such as biotin, desthiobiotin or iminobiotin, or an antibody. In one embodiment, the observable label is a secondary detection label such as azide, alkyne, aldehyde, amine, hydrazide, or diene, that is capable of forming a covalent bond with an alkyne, phosphine, azide, hydrazide, alkoxyamine, or alkene present on, e.g., an observable label. In one embodiment, the modifying molecule, if present, is a crosslinking agent, such as a photoactivatable crosslinking agent, and is capable of covalently attaching the modified nucleotide, and a nucleic acid in which the modified nucleotide has been incorporated, to another molecule.

In one embodiment, the observable label is desthiobiotin, and the compound is desthiobiotin-PEG$_{12}$-alkane-3',5'-cytidine-bisphosphate. In one embodiment, the observable label is an azide, and the compound is azido-PEG$_{12}$-alkane-3',5'-cytidine-bisphosphate. In one embodiment, the observable label is the mass tag TMT, and the compound is TMT-PEG$_{12}$-alkane-3',5'-cytidine-bisphosphate. In one embodiment, the modified nucleotide contains more than one observable label, and is, e.g., 3',5-cytidine-bisphosphate-Connecting Group-PEG$_n$-Obs.

Labeling occurs with high efficiency. In embodiments where the modified nucleotide is detected, the method achieves comparable sensitivity to radioisotope labeling, yet avoids the use of radioactivity with its concomitant disadvantages.

In one embodiment, n is an integer ranging from 2 to 24 inclusive, the sugar is ribose, the purine or pyrimidine base is A, C, G, U, or I, m is 3, n is 12, and the observable label is a streptavidin-binding label selected from biotin, desthiobiotin, or iminobiotin, or a mass tag, and the modifying molecule, if present, is a crosslinking agent.

In one embodiment, the modified nucleotide compounds have the following general structure (II):

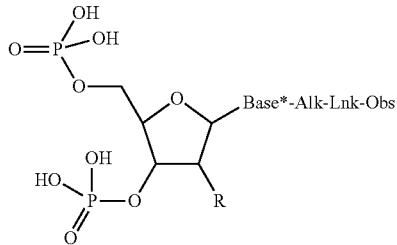

or its salt, conjugate base, tautomer, or ionized form where
Base* is a purine or pyrimidine base;
R is H, OH, CH$_3$, or a hydroxyl protecting group;
Alk is a connecting group between Base* and Lnk, having the structure -//—(CH$_2$)$_m$—Y—//- in which Y is a bond forming group selected from

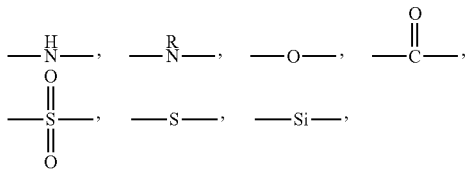

and
m is an integer ranging from 3 to 6 inclusive;
Lnk is a linking group having the following structures:

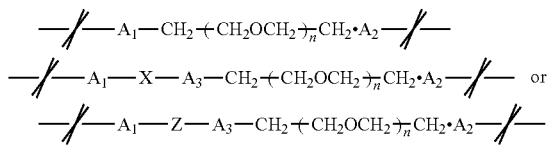

in which n is an integer ranging from 2 to 48 inclusive;
A$_1$ is a bond forming group selected from

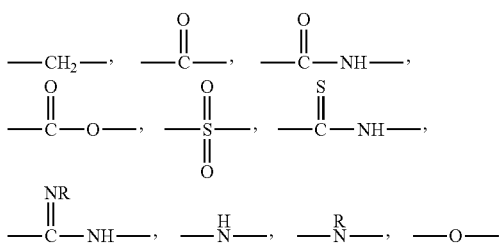

A$_2$ is a bond forming group selected from

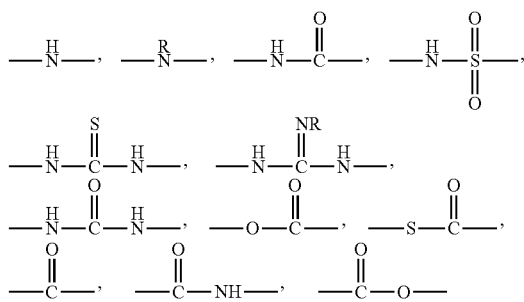

A$_3$ is a bond forming group selected from

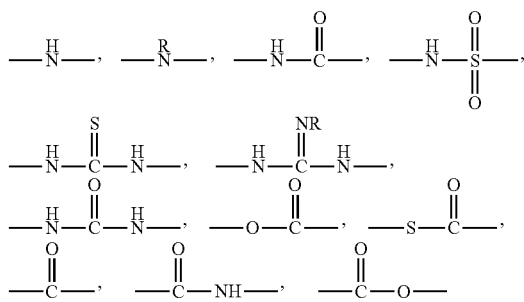

X is a cleavable group that can undergo silicon-carbon cleavage, nucleophilic cleavage, redox cleavage, acid cleavage, base cleavage, photochemical cleavage, enzymatic cleavage, or exchange-based cleavage; Z is a branching group that contains a modifying molecule (Mod); Mod is a modifying molecule (e.g., a crosslinking agent); and Obs is an observable label moiety (e.g., an observable label in itself such as a chromogen or fluor, or a molecule that can be rendered observable; a detecting agent; etc.)

The sugar is ribose or deoxyribose. The purine or pyrimidine base is C, U, A, G, T, or I and may be modified or unmodified. Embodiments include, but are not limited to, 1-methyladenine, N6-methyladenine, N6-isopentyladenine, N,N-dimethyladenine, 7-deazaadenine, 2-thiocytosine, 3-methylcytosine, N4-acetylcytosine, 2-thiocytosine, 1-methylguanine, 2-methylguanine, 7-methylguanine, N2,N2-dimethylguanine, 7-deazaguanine, 2-thiouracil, 6-thiopurine, or 2,6-diaminopurine.

In one embodiment, the observable label is an label that is directly or indirectly observable. Examples include, but are not limited to, a chromogen or fluorophore, e.g., fluorescein, rhodamine, commercially available dyes (e.g., DyLight® (Dyomics), Alexa®, Cy3, Cy5), etc., a mass tag, a spin label, or a moiety capable of binding an observable label. In one embodiment, the observable label is a molecule capable of binding or being captured by a corresponding binding partner, such as a streptavidin-binding label such as biotin, desthiobiotin or iminobiotin, or an antibody. In one embodiment, the observable label is a secondary detection label such as azide, alkyne, aldehyde, amine, hydrazide, or diene, which is capable of forming a covalent bond with an alkyne, phosphine, azide, hydrazide, alkoxyamine, or alkene present on, e.g., an observable label. In one embodiment, the modifying molecule is a crosslinking agent, such as a photoactivatable crosslinking agent, and is capable of covalently attaching the modified nucleotide, and a nucleic acid in which the modified nucleotide has been incorporated, to another molecule.

In one embodiment, n is an integer ranging from 2 to 24 inclusive. In one embodiment, the sugar is ribose, the purine or pyrimidine base is A, C, G, U, or I, m is 3, n is 12, and the observable label is a streptavidin-binding label selected from biotin, desthiobiotin, or iminobiotin, or a mass tag, and the modifying molecule, if present, is a crosslinking agent.

In one embodiment, the sugar is ribose, the purine or pyrimidine base is C, m is 3, Lnk is

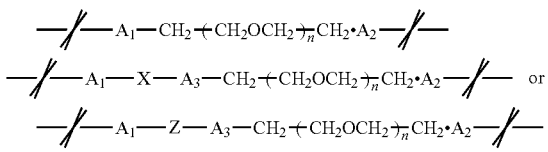

n is 12, $A_1$ is

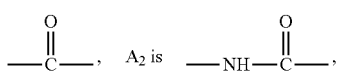

when present Z is

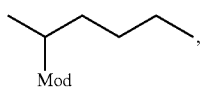

when present, $A_3$ is

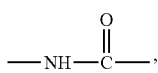

when present Mod is a crosslinking agent, and Obs is desthiobiotin, fluorophore, mass tag, and/or azide.

In one embodiment, the mass tag is a dimethyl piperidine- or dimethyl piperizine—(DMP)-based chemical affinity tag that may be isotopically labeled. The DMP-based chemical affinity tags are detection and capture bioconjugation reagents, which contain a small, non-biological epitope. The DMP-based chemical affinity tags are strong antigens for antibodies that are developed against the epitope. In one embodiment, a method for selectively capturing and eluting a sample containing a biomolecule labeled with the modified nucleotide, and/or a complex containing a biomolecule labeled with the modified nucleotide, is described in U.S. Application Ser. No. 61/648,959 "Selective Elution Anti-TMT Technology" which is hereby expressly incorporated by reference herein in its entirety, where the antibodies are immobilized, and samples containing the DMP-based chemical affinity tag are captured with the immobilized antibody. The labeled samples are then washed and competitively eluted with an elution reagent that contains a displacement molecule, e.g., a small molecule version of the epitope that is the tag itself or a fragment, substructure, or structural analog of the epitope. In one embodiment, the small molecule version of the epitope is piperidine, 2-S-methyl piperidine, 2-methyl piperidine, 2,2,4,4-tetramethyl piperidine, triethylamine, and/or diisopropylethylamine. In one embodiment, the displacement molecule is not a substructure of the epitope and epitope analogs, and instead is triethylammonia (TEA), N,N-disopropylethylammonia (DIPEA), and/or triethylammonium bicarbonate (TEAB). In one embodiment, the elution reagent contains more than one displacement molecule, where the displacement molecules may be a combination of a substructure of the epitope and epitope analogs, a combination of compounds that are not a substructure of the epitope and epitope analogs, and combinations of substructure of the epitope and epitope analogs and compounds that are not a substructure of the DMP epitope and epitope analogs. In one embodiment, the elution reagent contains at least one buffer, e.g., ((hydroxymethyl)aminomethane) (Tris), 4-(2-hydroxyethyl)-1-piperazineethanesulfonic acid (HEPES), 2-[[1,3-dihydroxy-2-(hydroxymethyl)propan-2-yl]amino]ethanesulfonic acid (TES), phosphate, 2-(N-morpholino)ethanesulfonic acid (MES), 3-morpholinopropane-1-sulfonic acid (MOPS), 1,4-piperazinediethanesulfonic acid (PIPES), bicarbonate, carbonate, N-(2-hydroxy-1,1-bis(hydroxymethyl)ethyl)glycine (tricine), N,N-(bis(2-hydroxyethyl)glycine (bicine), etc. The elution reagent is removed by methods know in the art, e.g., vacuum drying, desalting with dialysis or reversed phase or size exclusion chromatography. Multiple versions of the chemical tags are constructed with heavy stable isotopes or unique linkers between the epitope and reactive groups, allowing labeling of multiple samples, mixing of these samples, and multiplexed capture prior to mass spectrometry analysis. The competitive elution reagent may be removed by dialysis, size-exclusion desalting resin, precipitation, or vacuum drying.

In one embodiment, the modified nucleotide is a cytidine 3'-5'-bisphosphate having a $PEG_{12}$ linker with the structure shown below.

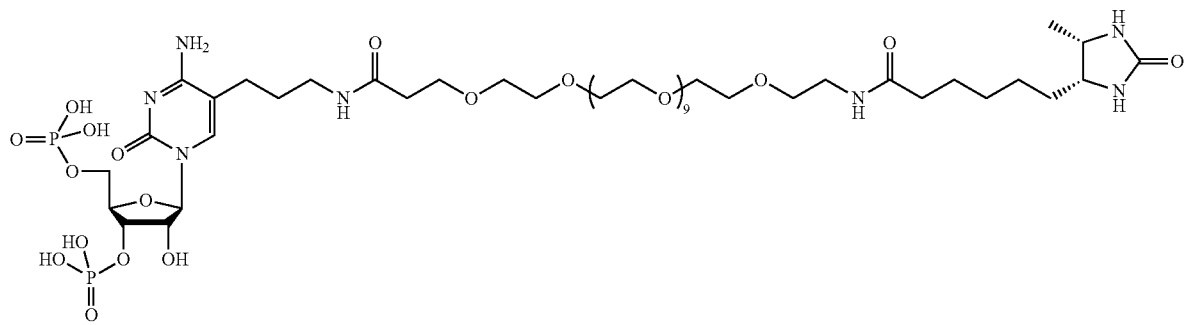

Desthiobiotin-PEG$_{12}$-Alkane-3',5'-Bisphosphate-Cytidine
(DP$_{12}$A-3',5'-pCp)

This structure had similar ligation efficiencies to biotin PEG$_4$-alkane-bisphosphate cytidine. The alkane, versus alkyne, linkage makes the linker containing the detector less reactive, and thus less susceptible to degradation in cell and/or tissue lysates.

Methods using the modified nucleotide, and/or a nucleic acid labeled with the modified nucleotide, are described. In one embodiment, the method labels a nucleic acid with the disclosed modified nucleotide. For example, RNA is labeled by heating a desired RNA sample to at least 75° C. and up to 95° C.; the solution containing the RNA sample may contain dimethylsulfoxide (DMSO) at a concentration ranging from 0% to 25%. The RNA sample was heated for 1 minute to 5 minutes, then rapidly cooled on ice to between 2° C. and 10° C. for at least one minute. The RNA then was contacted with one of the modified nucleotide compounds described above. The modified nucleotide was ligated to the RNA using an enzyme such as, but not limited to, T4 RNA ligase, to result in a labeled RNA. In this embodiment, RNA was heated to at least 75° C., and up to 95° C., then cooled for at least one minute to less than 10° C. The cooled RNA was then contacted with the modified nucleotide under reaction conditions using T4 RNA ligase and, including in the ligation reaction, PEG having molecular weight between about 1500 and 24,000 inclusive and at a concentration ranging from 5%$^{w/v}$ PEG to 20%$^{w/v}$ PEG inclusive. The reaction was incubated between 30 minutes and 16 hours at a temperature ranging between 16° C. and 37° C. to ligate the modified nucleotide to the RNA, resulting in a labeled RNA.

One embodiment is a method for labeling an RNA probe with a biotinylated nucleotide under conditions that label the RNA probe. The modified nucleotide was incubated with an enzyme capable of ligating the modified nucleotide to the RNA probe, e.g., a ligase such as T4 ligase, to result in a labeled RNA probe, e.g., a desthiobiotin-labeled and/or mass tag-labeled RNA probe. In one embodiment, single stranded T4 ligase was used. In one embodiment, double stranded T4 ligase is used. In one embodiment, thermostable T4 ligase is used. Examples of suitable ligases include T4 RNA Ligase 1 (applications include labeling of 3'-termini of RNA with 5'-[$^{32}$P] pCp, inter- and intramolecular joining of RNA and DNA molecules; synthesis of single-stranded oligodeoxyribonucleotides; and incorporation of unnatural amino acids into proteins); T4 RNA Ligase 2 (applications include ligating a nick in dsRNA, splintered RNA ligation, and ligating the 3' OH of RNA to the 5' phosphate of DNA in a double stranded structure); T4 RNA Ligase 2, truncated (applications include joining a single stranded adenylated primer to RNAs for cloning, and small RNA cloning); T4 RNA Ligase 2, truncated K227Q (applications include joining a single stranded adenylated primer to RNAs for cloning, small RNA cloning, and ligating with the lowest possible ligation byproduct); each of which is commercially available from New England BioLab; and thermostable RNA ligase, which is able to perform ligations at elevated temperatures, such as above about 40° C., commercially available from Epicentre. In one embodiment, the modified nucleotide is purified prior to ligation. Subsequent assaying for the labeled RNA probe permits detection of the presence, quantity, etc. of the ribonucleotide in the sample. The labeled RNA probe is used with, e.g. and without limitation, pull-down assays, such as for isolating RNA-binding proteins, mobility shift assays, Northern blots, in situ hybridization, etc. In embodiments, the biotin or desthiobiotin of a biotin-labeled RNA probe or desthiobiotin-labeled RNA probe is used as a capture moiety, e.g., by binding to streptavidin, or allows detection using a streptavidin-conjugated reporter molecule such as, e.g. and without limitation, enzymes (e.g., peroxidases), fluorescent dyes, etc.

For an assay using a labeled RNA to enrich for a component, whether the substance containing the component was bound to a chip, resin, etc., e.g., a pull-down assay, labeled RNA was incubated in a binding reaction containing the protein, RNA, or DNA of interest, an optimized binding buffer, and affinity resin. The resin was then washed, the RNA complex was eluted, and the protein, DNA, or RNA of interest was detected using techniques including but not limited to PCR, RT-PCR, Western blot, or microarray.

In one embodiment, the method analyzes RNA-binding proteins. A biological sample that contains at least one RNA-binding protein was contacted with an RNA molecule labeled with a described modified nucleotide under conditions suitable for forming a complex between the labeled RNA molecule and an RNA-binding protein. The biological sample may be, e.g., a purified protein, a tissue sample, whole tissue, whole organ, cell culture, cell extract, cell lysate, or in vitro translated protein lysate. In one embodiment, the labeling nucleotide, and thus, the resultant labeled RNA molecule, contains a first binding partner, such as a biotin moiety, e.g., desthiobiotin, or a mass tag. A second binding partner, such as streptavidin or an antibody to the mass tag, was used to bind and capture the labeled RNA molecule/RNA-binding protein complex by interaction with the first binding partner, e.g., biotin moiety or mass tag, of the modified nucleotide used to label the RNA molecule. In one embodiment, the second binding partner was attached to a solid support, such as a bead, plate, column, etc. as known in the art. The RNA molecule/RNA-binding protein complex was attached to the solid support by interaction between the first and second binding partners. The RNA molecule/RNA-binding protein complex was then collected by removing it from the solid support, i.e., the complex is washed off the solid support using suitable conditions and solvents, such as competitively eluting the complex with a small molecule version of the mass tag epitope which is comprised of the tag itself or a fragment, substructure, or structural analog of the epitope. In embodiments, the eluted RNA-binding protein was detected and/or quantitated by Western blot. In embodiments, the interaction between the labeled RNA probe and the RNA-binding protein is stabilized by crosslinking the RNA-binding protein to the labeled RNA probe by the modifying molecule of the modified nucleotide or by adding crosslinkers (e.g., by exposure to ultraviolet (UV) light) after the RNA molecule/RNA-binding protein complex has bound to the affinity matrix. In one embodiment, the modifying molecule is a photoactivatable crosslinking agent.

For mobility shift assays, an excess of the labeled RNA was incubated with a solution containing the protein, RNA, or DNA of interest in an optimized binding buffer. The incubation conditions were empirically determined; incubation time typically ranged from 5 minutes to 1 hour, incubation temperatures typically ranged from 4° C. to room temperature (about 19° C. to about 22° C.).

The binding reaction was then subjected to electrophoresis to separate RNA binding complexes from free probe. The shifted RNA complex was then detected in-gel, or transferred to a positively charged membrane and detected using secondary detection reagents, e.g., with a chromogen or by chemiluminescence.

For Northern blotting, the labeled RNA was used to detect RNA that had been separated by electrophoresis and transferred onto a membrane. The labeled RNA was denatured for 5 minutes to 10 minutes at 95° C. and quickly cooled on ice to less than 10° C. The denatured probe was then added to an optimized hybridization solution and incubated with the membrane at an empirically determined temperature for at least 1 hour, but up to overnight. The membrane was then washed and RNA was detected using secondary detection reagents, e.g., with a chromogen or by chemiluminescence).

For in situ hybridization, the labeled RNA ws used as a probe for the detection of the RNA or RNA complex of interest in cells. The labeled RNA may be used after cells have been fixed onto a support (i.e., a microscope slide, coverslip, tissue dish, microwell, etc.), or in suspension for flow cytometric analysis. Similarly, the labeled RNA may be transfected into live cells, and detected directly or using secondary reagents. The RNA or RNA complex was visualized using techniques including but not limited to light or fluorescent microscopy, flow cytometric analysis, or microarray.

One embodiment is a method to assay RNA using an RNA probe labeled with the compound described above and using the method described above. The labeled RNA can be synthesized as described above. The labeled RNA probe was contacted with the sample to be assayed under conditions to permit the labeled RNA to hybridize with RNA in the sample. The hybridized RNA was then detected in an assay, e.g., mobility shift, Northern blot, in situ hybridization, pull-down assay, etc. using, e.g., an observable label such as a biotin and a streptavidin-conjugated reporter molecule such as an enzyme, a fluorescent compound, an isotope, a gold particle, etc.

One embodiment is a kit containing any of the above described compounds and instructions for labeling a nucleic acid using the compound. The kit can also contain an enzyme, a control RNA either labeled or unlabeled with the modified nucleotide, and a buffer.

One embodiment is a kit to label RNA with the compound described above. In one embodiment, the kit contains the compound(s), ligase, ligase buffer, and labeling instructions. In one embodiment, the kit contains additional kit components to enhance ligation efficiency including polyethylene glycol as a size exclusion reagent and DMSO to relax secondary structure. In one embodiment, the kit also includes a control RNA that ligates with greater than 75% efficiency, and a synthetic biotinylated RNA control to assess ligation efficiency. Instructions include methods for a typical ligation reaction using the reagents listed and/or instructions for using a nucleic acid comprising the labeled nucleotide in a method, such as mobility shift, Northern blot, pull-down assay, or in situ hybridization. In one embodiment, the kit contains a described compound where the sugar is ribose, the purine or pyrimidine base is C, m is 3, Lnk is

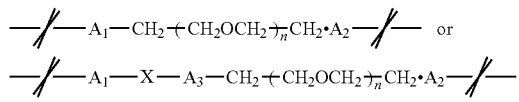

n is 12, $A_1$ is

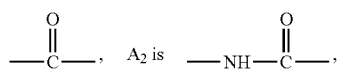

when present Z is

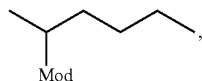

when present $A_3$ is

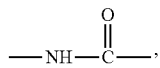

when present Mod is a crosslinking agent, and Obs is biotin, desthiobiotin, and/or a mass tag.

One embodiment is a kit for isolating RNA-binding proteins. The kit contains the disclosed modified nucleotide, where Obs is biotin, desthiobiotin, and/or a mass tag and instructions for using RNA labeled with the compound as bait to isolate an RNA-binding protein in a pull-down assay. In one embodiment, the kit further contains reagents for crosslinking.

Synthesis of exemplary specific compounds among each of the following modified nucleotides is subsequently described. One skilled in the art will appreciate that such synthesis schemes are representative and not limiting; one skilled in the art knows or can readily determine how to synthesize other specific examples using known methods and without undue experimentation. Other such examples include, but are not limited to, biotin-$PEG_4$ modifications, biotin-$PEG_4$-alkane-3',5'-cytidine-bisphosphate (BPA-3',5'-pCp, compound 6), overview of biotin-$PEG_4$-SS-alkane-3',5'-cytidine-bisphosphate ($BP_4$SSA-3',5'-pCp, compound 12), biotin-$PEG_4$-SS-alkane-cytidine ($BP_4$SSAC, compound 11), and detailed reactions for biotin-$PEG_4$-SS-alkane-3',5'-cytidine-bisphosphate ($BP_4$SSA-3',5'-pCp, compound 12); biotin-$PEG_{12}$ modifications; azido-$PEG_4$ modifications; fluorophore-$PEG_4$ modifications, DyLight 550-$PEG_4$-alkane-3',5'-cytidine-bisphosphate (Dy550$P_4$A-3',5'-pCp, compound 14).

Biotin-$PEG_4$ Modification

To prepare biotin-polyethylene glycol (PEG)-alkane-3',5'-cytidine-bisphosphate, propargyl amine was reacted with methyl trifluoroacetate to result in propargyltrifluoroacetamide. The propargyltrifluoroacetamide reacts with 5-iodocytidine to result in 5-[3-(trifluoroacetamido)propynyl]cytidine. The 5-[3-(trifluoroacetamido)propynyl]cytidine is converted to 5-[3-(trifluoroacetamido)propyl]cytidine. The 5-[3-(trifluoroacetamido)propyl]cytidine then is converted to 5-(3-aminopropyl)cytidine. The 5-(3-aminopropyl)cytidine then is reacted with NHS-PEG-biotin to result in biotin-PEG-alkane-cytidine. The biotin-PEG-alkane-cytidine then is reacted with diphosphoryl chloride to result in biotin-polyethylene glycol (PEG)-alkane-3',5'-cytidine-bisphosphate.

Propargyltrifluoroacetamide (1) was prepared according to the following reaction:

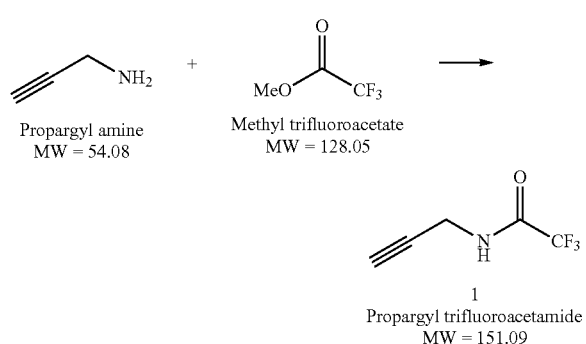

Propargyl amine (4.00 g, 72.62 mmol, 1.00 equiv.) was added dropwise to methyl trifluoroacetate (11.16 g, 87.15 mmol, 1.20 equiv.) at 0° C. The reaction mixture was stirred at 0° C. for 2 h and then concentrated under reduced pressure to remove methanol. The product was purified by vacuum distillation yielding propargyltrifluoroacetamide as a colorless liquid (9.59 g, 87%). The structure was confirmed by $^1$H- and $^{19}$F-NMR.

5-[3-(trifluoroacetamido)propynyl]cytidine (2) was prepared according to the following reaction:

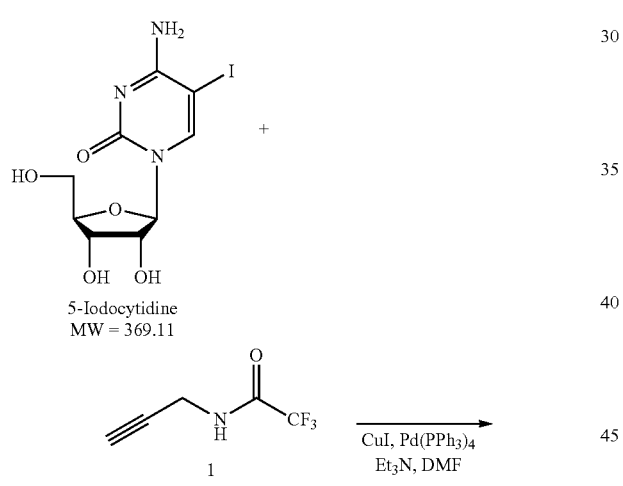

A 100-mL three-necked flask was charged with 5-iodocytidine (2.66 g, 7.00 mmol, 1.00 equiv.), cuprous iodide (0.267 g, 1.40 mmol, 0.20 equiv.) and dry DMF (35 mL). After complete dissolution of the reaction mixture, propargyltrifluoroacetamide (3.17 g, 21.00 mmol, 3.00 equiv.), triethylamine (1.42 g, 14.00 mmol, 2.00 equiv.) and finally tetrakis(triphenylphosphine)palladium(0) (0.809 g, 0.70 mmol, 0.10 equiv.) were added to the reaction mixture under $N_2$. The reaction was stirred at ambient temperature (around 19° C. to around 22° C.) under $N_2$ for 18-24 h. The reaction was then diluted with 70 mL of 1:1 methanol-dichloromethane and the bicarbonate form of AGI X8 resin (12.00 g) was added. After stirring for about one h, the reaction mixture was filtered and the resin was washed with 1:1 methanol-dichloromethane. The combined filtrates were rapidly concentrated with a rotary evaporator. The residue was immediately purified by flash chromatography. Removal of solvent from the appropriate fractions afforded 1.84 g (67%) of 5-[3-(trifluoroacetamido)propynyl]cytidine as a light brown solid, which was confirmed by $^1$H-NMR.

5-[3-(trifluoroacetamido)propyl]cytidine (3) was prepared according to the following reaction:

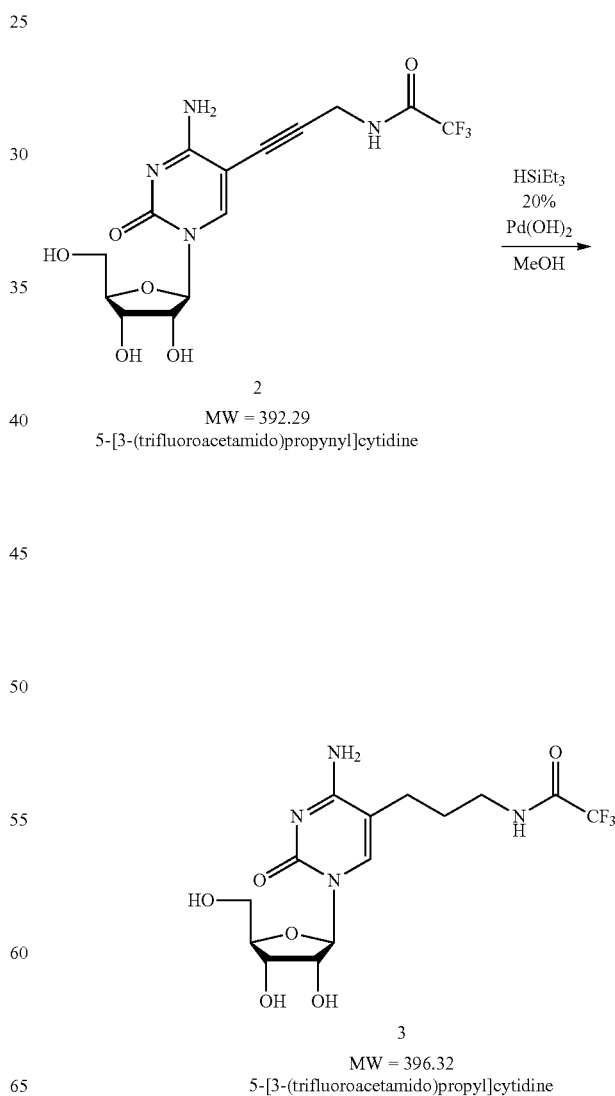

5-[3-(trifluoroacetamido)propynyl]cytidine (1.25 g, 3.19 mmol, 1.00 equiv.) was dissolved in methanol (30 mL). Palladium hydroxide (0.25 g, 20 wt./wt. % based on propynyl cytidine) and triethylsilane (3.71 g, 31.90 mmol, 10.00 equiv.) were added to the reaction mixture. After 20-24 hours at ambient temperature, the reaction mixture was filtered through glass fiber and the filtrate was concentrated under reduced pressure giving a dark brown residue. The residue was purified by flash chromatography. Removal of solvent from the appropriate fractions afforded 0.85 g (71%) of 5-[3-(trifluoroacetamido)propyl]cytidine as a cream colored solid, which was confirmed by $^1$H-NM. 5-(3-aminopropyl)cytidine (4) was prepared according to the following reaction:

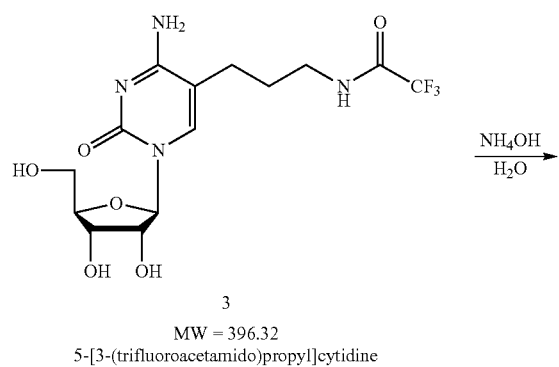

3
MW = 396.32
5-[3-(trifluoroacetamido)propyl]cytidine

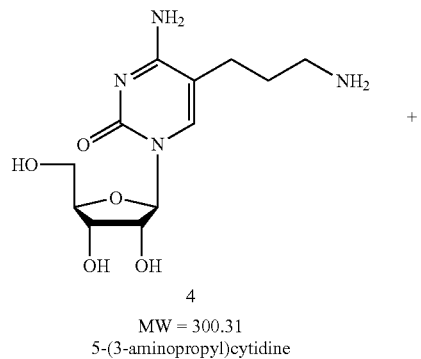

4
MW = 300.31
5-(3-aminopropyl)cytidine

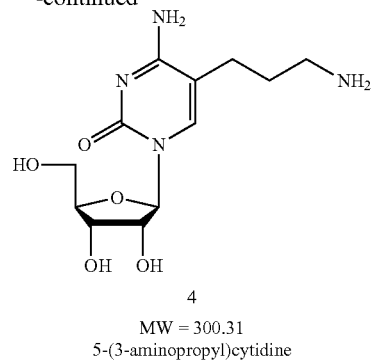

4
MW = 300.31
5-(3-aminopropyl)cytidine

5-[3-(trfluoroacetamido)propyl]cytidine (0.69 g, 1.74 mmol) was dissolved in DI H$_2$O (8.5 mL). After complete dissolution, concentrated ammonium hydroxide (NH$_4$OH) (8.5 mL) was added to the reaction mixture. The reaction solution was stirred at ambient temperature for 2-3 h and then concentrated under reduced pressure giving the crude product as yellow-orange residue. The crude product was dissolved in deionized H$_2$O (10 mL) and AG50W-X8 resin (2.5 g) was added to the solution. The suspension was stirred for 15 min and filtered over a bed of AG50W-X8 resin (2.5 g). The resin was washed with DI H$_2$O and the product was then eluted off of the resin by washing the resin with deionized H$_2$O/conc. NH$_4$OH, 4:1, collecting fractions (monitored by TLC). Removal of solvent from the appropriate fractions afforded 0.51 g (98%) of 5-(3-aminopropyl)cytidine as light tan solid, which was confirmed by $^1$H-NMR.

Biotin-PEG$_4$-alkane-cytidine (BPAC, 5) was prepared according to the following reaction:

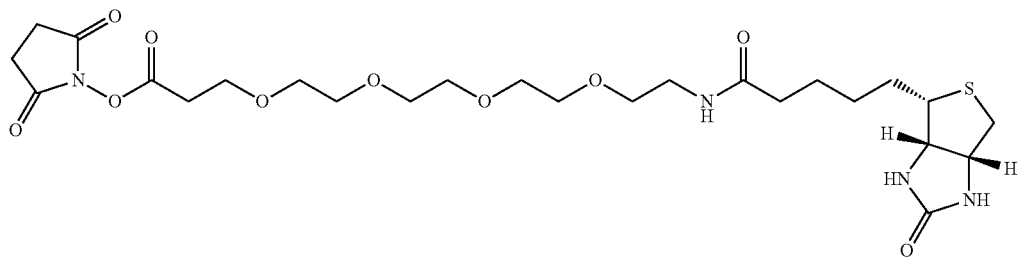

MW = 588.67
NHS-PEG$_4$-Biotin

↓ DMF

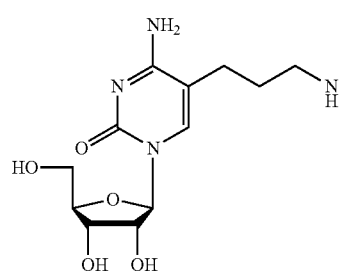
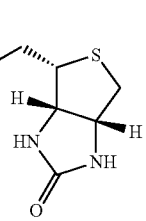

-continued

5
MW = 773.89
(BPAC)

NHS-PEG$_4$-biotin (0.196 g, 0.333 mmol, 1.00 equiv.) was dissolved in DMF (10 mL). 5-(3-aminopropyl)cytidine) (0.100 g, 0.333 mmol, 1.00 equiv.) was added to the reaction solution. The reaction solution was stirred at ambient temperature under N$_2$ atmosphere. After 20-24 h, the reaction mixture was concentrated under reduced pressure giving the crude product. The crude product was purified by flash chromatography. Removal of solvent from the appropriate fractions afforded 0.18 g (69%) of BPAC as a white solid, which was confirmed by $^1$H-NMR.

Biotin-PEG$_4$-alkane-3',5'-cytidine-bisphosphate (BPA-3', 5'-pCp, 6) was prepared according to the following reaction:

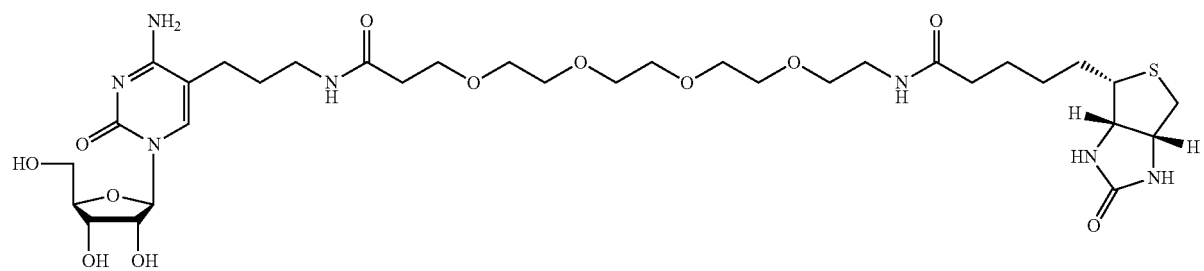

5
MW = 773.89
(BPAC)

1. Diphosphoryl chloride
2. 0.5M TEAB buffer, pH 8.5
3. C18, FPLC, C18

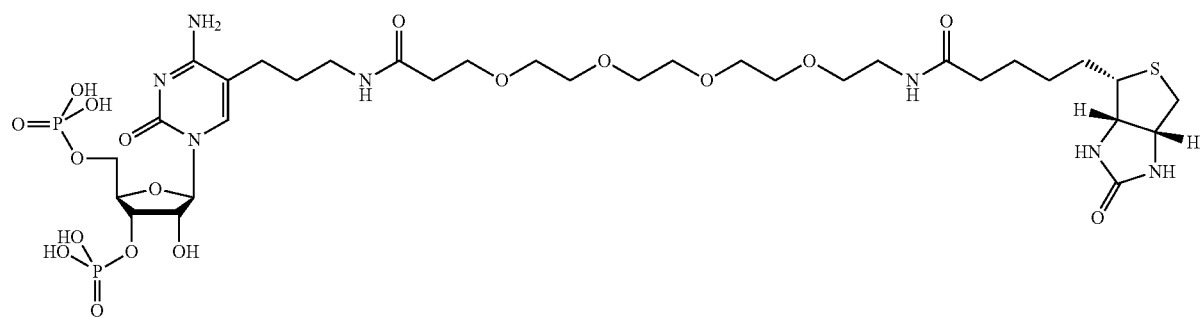

6
MW = 933.85
(BPA-3',5'-pCp)

BPAC (0.061 g, 0.079 mmol, 1.00 equiv.) was partially dissolved in diphosphoryl chloride (196 μL, 1.66 mmol, 21.00 equiv.), previously cooled to −10° C. to −15° C. in a 1-mL Reacti-Vial™. The mixture was then stirred at −10° C. to −15° C. After 5 h, the reaction was quenched by addition of ice cold water (1-2 mL) and, immediately thereafter, with a chilled solution of 0.5 M TEAB buffer, pH 8.5 (17 mL). Upon stabilization at neutral pH, the colorless solution was stirred at ambient temperature for 30 min and concentrated using a rotary evaporator until complete removal of TEAB.

The solution was desalted using a C18 cartridge (Waters) and purified by FPLC (MonoQ 10/100GL column, GE) using a pH gradient. After a final desalting using again a C18 cartridge (Waters), BPA-3',5'-pCp was isolated after lyophilization as a white solid (10 mg, 9%), which was confirmed by $^1$H-NMR & HPLC.

Overview of Preparation of BIOTIN-PEG$_4$-SS-ALKANE-3',5'-CYTIDINE-BISPHOSPHATE (BP$_4$SSA-3',5'-pCp, Compound 12)

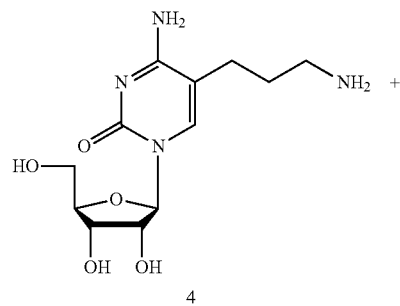

4

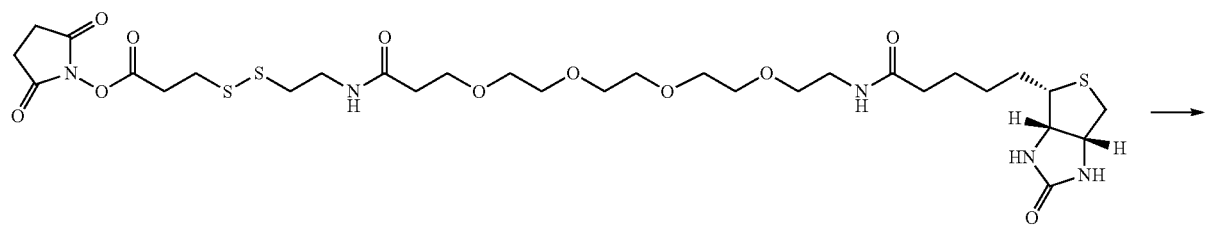

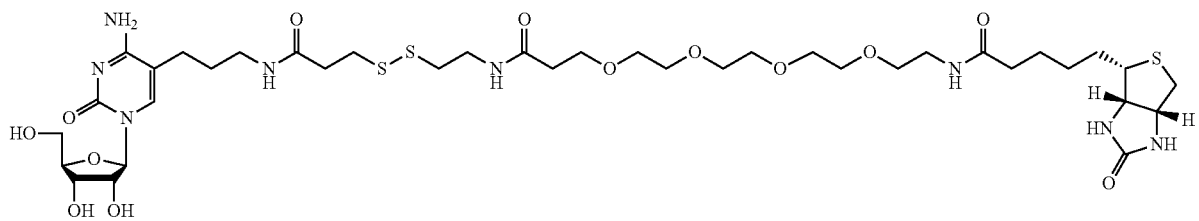

11

11 $\xrightarrow{\text{1. Phosphorylation} \atop \text{2. C18, FPLC, C18}}$

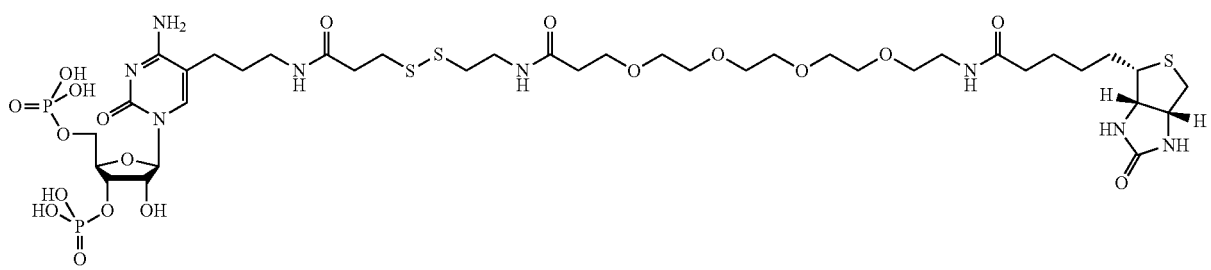

12

The reaction scheme to prepare biotin-polyethylene glycol (PEG)-SS-alkane-3',5'-cytidine-bisphosphate is as follows. The 5-(3-aminopropyl)cytidine (compound 4) is reacted with NHS—SS-PEG-biotin to result in biotin-PEG-SS-alkane-cytidine (compound 11). The biotin-PEG-SS-alkane-cytidine (compound 11) then is reacted with diphosphoryl chloride to result in biotin-polyethylene glycol (PEG)-SS-alkane-3',5'-cytidine-bisphosphate (compound 12).

Preparation of
BIOTIN-PEG₄-SS-ALKANE-CYTIDINE
(BP₄SSAC, Compound 11)

NHS—SS-PEG₄-biotin (0.250 g, 0.333 mmol, 1.00 equiv.) was dissolved in DMF (10 mL). 5-(3-aminopropyl)cytidine) (0.100 g, 0.333 mmol, 1.00 equiv.) was added to the reaction solution. The reaction solution was stirred at ambient temperature under $N_2$ atmosphere. After 20-24 hours, the reaction mixture was concentrated under reduced pressure giving the crude product. The crude product was purified by flash chromatography. Removal of solvent from the appropriate fractions afforded 0.19 g (61%) of BP₄SSAC (compound 11) as a white solid, which was confirmed by $^1$H-NMR.

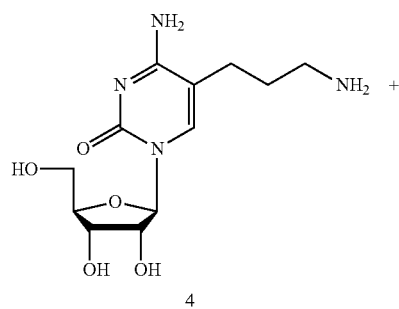

4

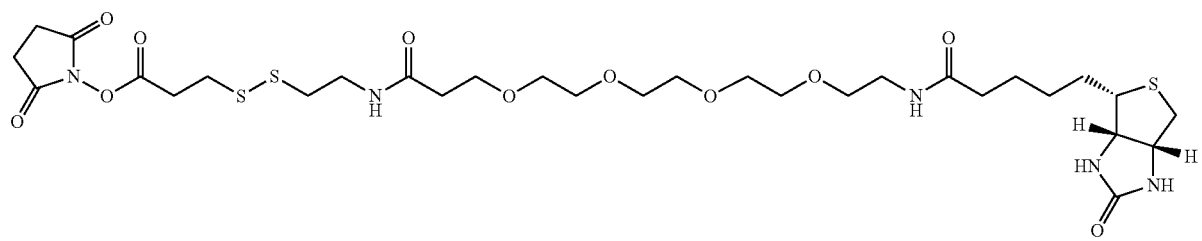

MW = 751.93
NHS-SS-PEG₄=Biotin

|DMF

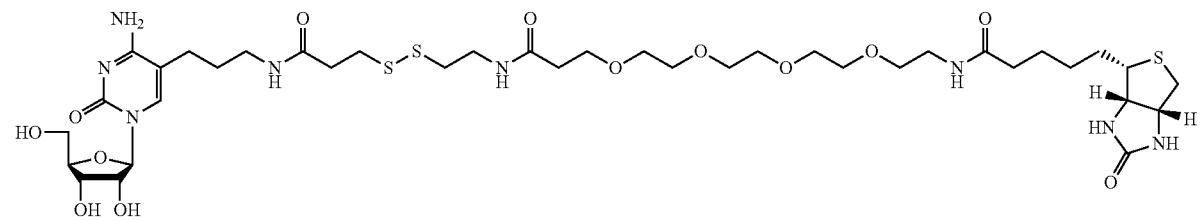

11
MW = 937.16
Biotin-PEG₄-SS-Alkane-Cytidine
(BP₄SSAC)

Preparation of BIOTIN-PEG$_4$-SS-ALKANE-3',5'-CYTIDINE-BISPHOSPHATE (BP$_4$SSA-3',5'-pCp, Compound 12)

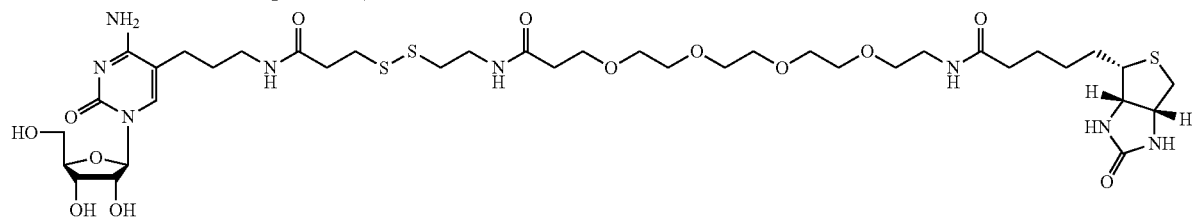

11
MW = 937.16
Biotin-PEG$_4$-SS-Alkane-Cytidine
(BP$_4$SSAC)

1. Diphosphoryl chloride
2. 0.5M TEAB buffer, pH 8.5
3. C18, FPLC, C18

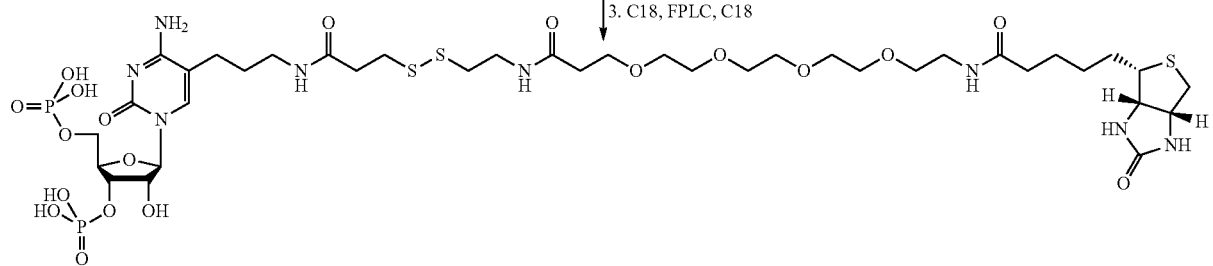

12
MW = 1097.12
Biotin-PEG$_4$-SS-Alkane-3',5'-Bisphosphate-Cytidine
(BP$_4$SS-3',5'-pCp)

BP$_4$SSAC (0.074 g, 0.079 mmol, 1.00 equiv.) was partially dissolved in diphosphoryl chloride (196 µL, 1.66 mmol, 21.00 equiv.), previously cooled to −10° C. to −15° C. in a 1-mL Reacti-Vial™. The mixture was then stirred at −10° C. to −15° C. After five hours, the reaction was quenched by addition of ice cold water (1-2 mL) and, immediately thereafter, with a chilled solution of 0.5M TEAB buffer, pH 8.5 (17 mL). Upon stabilization at neutral pH, the colorless solution was stirred at ambient temperature for 30 min and concentrated using a rotary evaporator until complete removal of TEAB. The solution was desalted using a C18 cartridge (Waters) and purified by FPLC (MonoQ 10/100GL column, GE) using a pH gradient. After a final desalting using again a C18 cartridge (Waters), BP$_4$SSA-3',5'-pCp (compound 12) was isolated after lyophilization as a white solid (5 mg, 6%), which was confirmed by $^1$H-NMR and HPLC.

Biotin-PEG$_2$ Modification

Preparation of BIOTIN-PEG$_{12}$-ALKANE-CYTIDINE (BP$_{12}$AC, Compound 7)

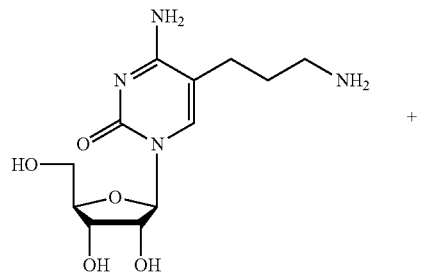

4
MW = 300.31
5-(3-aminopropyl)cytidine

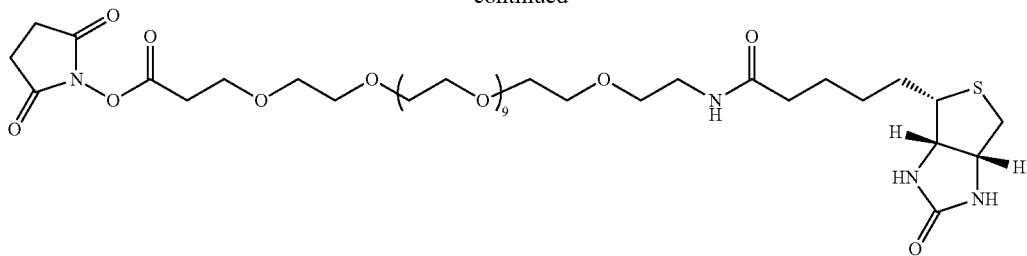

MW = 941.09
NHS-PEG$_{12}$-Biotin

↓ DMF

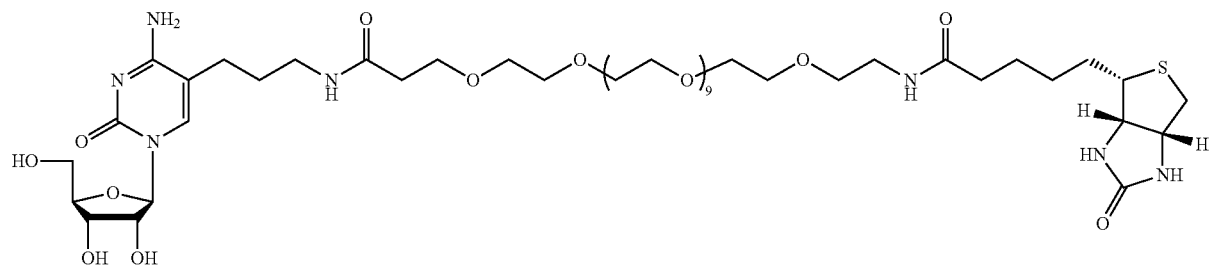

7
MW = 1126.31
Biotin-PEG$_{12}$-Alkane-Cytidine
(BP$_{12}$AC)

NHS-PEG$_{12}$-biotin (0.313 g, 0.333 mmol, 1.00 equiv.) was dissolved in DMF (10 mL). 5-(3-aminopropyl)cytidine (0.100 g, 0.333 mmol, 1.00 equiv., compound 4) was added to the reaction solution. The reaction solution was stirred at ambient temperature under N$_2$ atmosphere. After 20-24 h, the reaction mixture was concentrated under reduced pressure giving the crude product. The crude product was purified by flash chromatography. Removal of solvent from the appropriate fractions afforded 0.27 g (72%) of BP$_{12}$AC (compound 7) as a light yellow foam, which was confirmed by $^1$H-NMR.

Preparation of BIOTIN-PEG$_{12}$-ALKANE-3',5'-BIS-PHOSPHATE-CYTIDINE (BP$_{12}$A-3',5'-pCp, Compound 8)

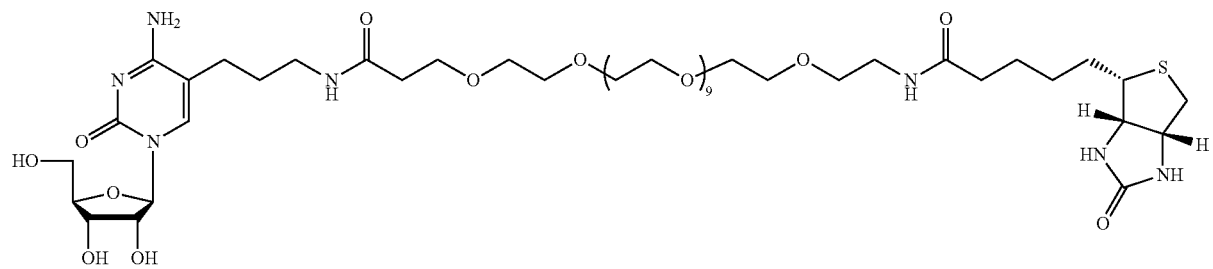

7
MW = 1126.31
Biotin-PEG$_{12}$-Alkane-Cytidine
(BP$_{12}$AC)

1. Diphosphoryl chloride
2. 0.5M TEAB buffer, pH 8.5
3. C18, FPLC, C18

-continued

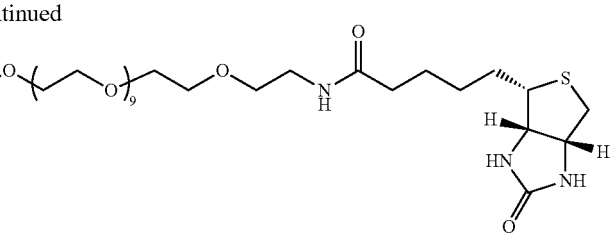

8
MW = 1286.27
Biotin-PEG$_{12}$-Alkane-3',5'-Biophosphate-Cytidine
(BP$_{12}$A-3',5'-pCp)

Biotin-PEG$_{12}$-alkane-cytidine (0.135 g, 0.120 mmol, 1.00 equiv., compound 7) was partially dissolved in diphosphoryl chloride (315 μL, 2.40 mmol, 20.00 equiv.), previously cooled to −10 to −15° C. in a 1-mL Reacti-Vial™. The mixture was stirred at −10 to −15° C. After five hours, the reaction was quenched by adding ice cold water (1-2 mL) and immediately after with a chilled solution of 0.5M TEAB buffer, pH 8.5 (40 mL). Upon stabilization at neutral pH, the colorless solution was stirred at ambient temperature for 30 min and concentrated using a rotary evaporator until TEAB was completely removed. The solution was desalted using a C18 cartridge (Waters) and purified by FPLC (MonoQ 10/100GL column, GE) using a pH gradient. After final desalting using a C18 cartridge (Waters), biotin-PEG$_{12}$-alkane-3',5'-cytidine-bisphosphate (compound 8) was isolated after lyophilization as a sticky white solid (8 mg, 5%), which was confirmed by 1H-NMR and HPLC.

Azido-PEG$_4$ Modification

Azido-PEG$_4$-alkane-3',5'-cytidine-bisphosphate, Compound 9

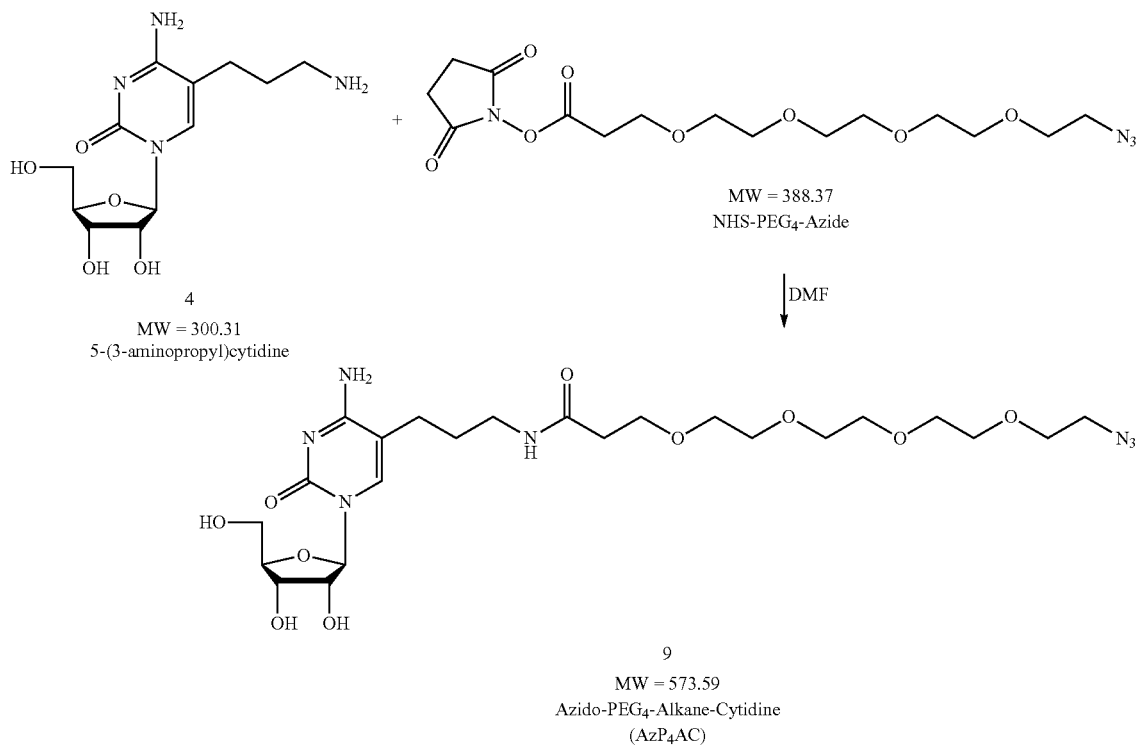

One embodiment is a method of preparing azido-PEG$_4$-alkane-3',5'-cytidine-bisphosphate. The 5-(3-aminopropyl) cytidine was synthesized as described above, then was reacted with NHS-PEG$_4$-azide to result in azido-PEG$_4$-alkane-cytidine. The azido-PEG$_4$-alkane-cytidine was then reacted with diphosphoryl chloride to result in azido-PEG$_4$-alkane-3',5'-cytidine-bisphosphate.

NHS-PEG₄-azide (0.408 g, 1.05 mmol, 1.00 equiv.) was dissolved in DMF (32 mL). The 5-(3-aminopropyl)cytidine) (0.315 g, 1.05 mmol, 1.00 equiv.) was added to the reaction solution. The reaction solution was stirred at ambient temperature under N₂ atmosphere. After 20-24 hours, the reaction mixture was concentrated under reduced pressure giving the crude product. The crude product was purified by flash chromatography. Removal of solvent from the appropriate fractions afforded 0.378 g (63%) of azido-PEG₄-alkane-cytidine (compound 9) as a near colorless glass, which was confirmed by 1H-NMR.

Azido-PEG₄-alkane-3',5'-Bisphosphate-Cytidine (AzP₄A-3',5'p-C-p), Compound 10

Azido-PEG₄-alkane-cytidine (0.150 g, 0.262 mmol, 1.00 equiv., compound 9) was partially dissolved in diphosphoryl chloride (688 μL, 5.24 mmol, 20.00 equiv.), previously cooled to −10 to −15° C. in a 1 mL Reacti-Vial™. The mixture was then stirred at −10 to −15° C. After five hours, the reaction was quenched by adding ice cold water (2-3 mL) and then immediately with a chilled solution of 0.5M TEAB buffer, pH 8.5 (87 mL). Upon stabilization at neutral pH, the colorless solution was stirred at ambient temperature for 30 min and concentrated using a rotary evaporator until TEAB was complete removed. The solution was desalted using a C18 cartridge (Waters) and purified by FPLC (MonoQ 10/100GL column, GE) using a pH gradient. After final desalting using again a C18 cartridge (Waters), azido-PEG₄-alkane-3',5'-cytidine-bisphosphate (compound 10) was isolated after lyophilization as a sticky white solid (10 mg, 6%), confirmed by 1H-NMR and HPLC.

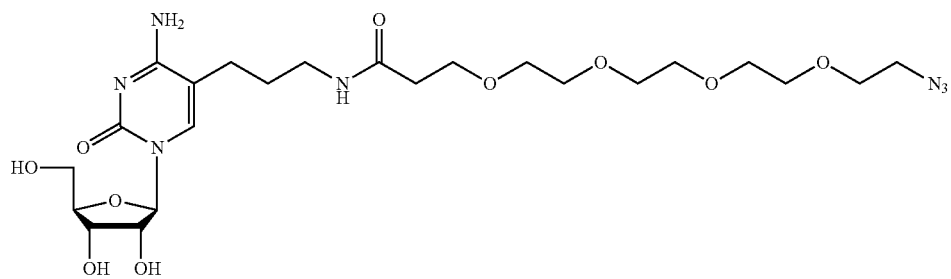

9
MW = 573.59
Azido-PEG₄-Alkane-Cytidine
(AzP₄AC)

1. Diphosphoryl chloride
2. 0.5M TEAB buffer, pH 8.5
3. C18, FPLC, C18

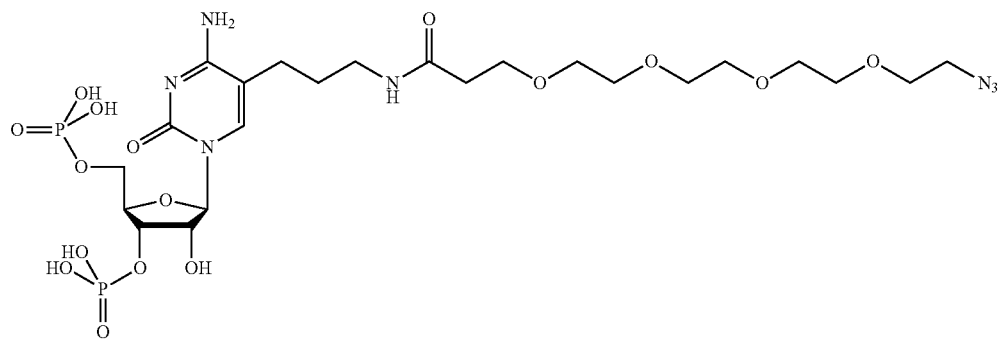

10
MW = 733.55
Azido-PEG₄-Alkane-3',5'-Biophosphate-Cytidine
(AzP₄A-3',5'-pCp)

Fluorophore-PEG₄ Modifications

Preparation of DyLight 550-PEG₄-ALKANE-3',5'-CYTIDINE-BISPHOSPHATE (Dy550P₄A-3',5'-pCp, 14)

DyLight 550-polyethylene glycol (PEG)-alkane-3',5'-cytidine-bisphosphate (compound 14) is prepared as follows. The azido-PEG₄-alkane-3',5'-cytidine-bisphosphate (compound 10) was synthesized as described above, then allowed to react with tris(2-carboxyethyl)phosphine hydrochloride (TCEP) to result in amino-PEG₄-alkane-3,'5'-cytidine bisphosphate (compound 13). The amino-PEG₄-alkane-3,'5'-cytidine bisphosphate (compound 13) was then reacted with DyLight 550 NHS ester to result in 550-polyethylene glycol (PEG)-alkane-3',5'-cytidine-bisphosphate (compound 14).

Preparation of AMINO-PEG₄-ALKANE-3',5'-BIS-PHOSPHATE-CYTIDINE (AmP₄A-3',5'-pCp, 13)

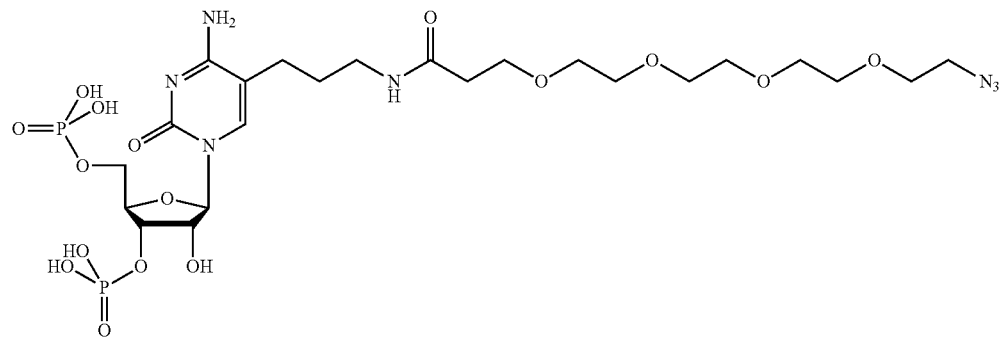

10
MW = 733.55
Azido-PEG₄-Alkane-3',5'-Biophosphate-Cytidine
(AzP₄A-3',5'-pCp)

1. TCEP
2. FPLC

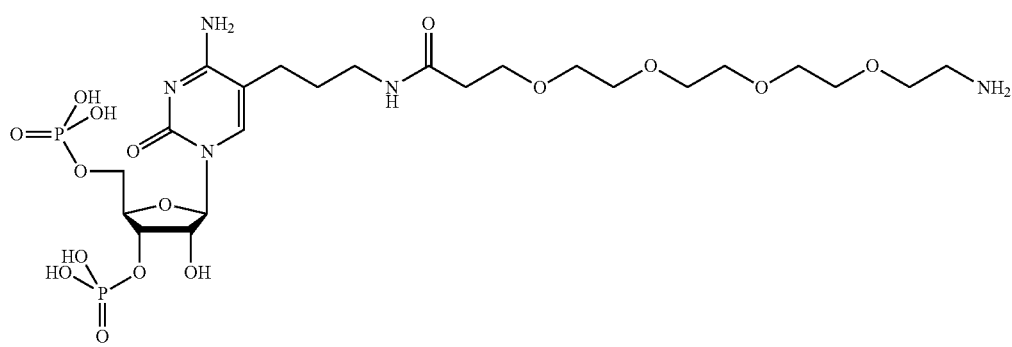

13
MW = 707.56
Amino-PEG₄-Alkane-3',5'-Biophosphate-Cytidine
(AmP₄A-3',5'-pCp)

Azido-PEG₄-alkane-3',5'-bisphosphate-cytidine (3.56 pmol, 1.00 equiv., compound 10) was dissolved in 200 mM Tris/HCl, pH 7.5 (800 μL). Tris(2-carboxyethyl)phosphine hydrochloride (TCEP) (17.54 mg, approx. 5.00 equiv.) was dissolved in 200 mM Tris/HCl, pH 7.5 (688 μL). The TCEP solution (200 μL) was added to the solution of azide and the reaction was mixed at ambient temperature. After 1-3 h, the reaction mixture was purified by FPLC and the fractions containing product were treated directly with DyLight 550 NHS ester to result in amino-PEG₄-alkane-3',5'-bisphosphate cytidine (compound 13).

Preparation of DyLight 550-PEG₄-ALKANE-3',5'-BISPHOSPHATE-CYTIDINE (Dy550P₄A-3',5'-pCp, 14)

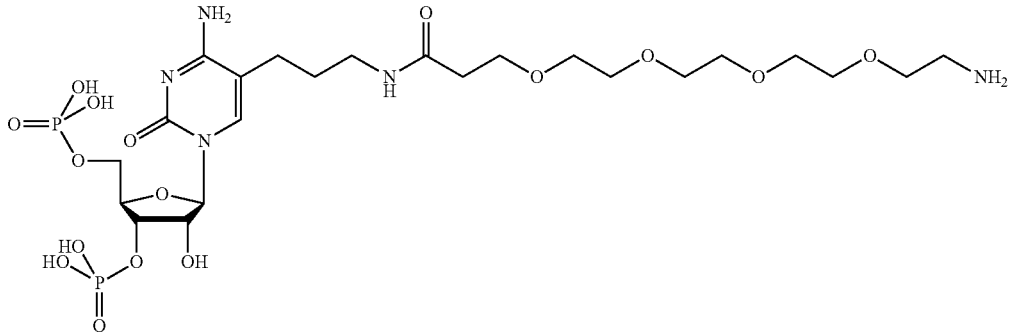

13
MW = 707.56
Amino-PEG₄-Alkane-3',5'-Biophosphate-Cytidine
(AmP₄A-3',5'-pCp)

1. DyLight 550 NHS Ester
2. FPLC

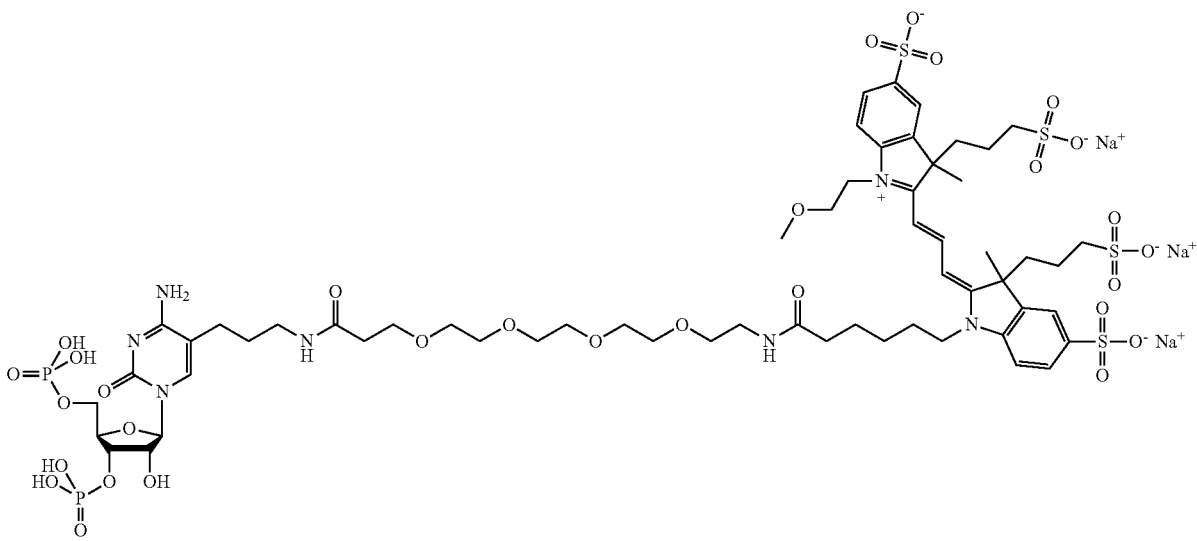

14
MW = 1632.52
DyLight550-PEG₄-Alkane-3',5'-Biophosphate-Cytidine
(Dy550P₄A-3',5'-pCp)

The pH of an FPLC fraction (2 mL) containing amino-PEG₄-alkane-3',5'-bisphosphate-cytidine (compound 13) was adjusted to pH 7.0 by adding 1M HEPES, pH 7.3. Separately, a 1 mM solution of DyLight 550 NHS ester was prepared by dissolving DyLight 550 NHS ester (MW=1040.05, 1 mg) in ultra pure water (960 μL). Amino-PEG₄-alkane-3',5'-bisphosphate-cytidine (0.25 mL) and DyLight 550 NHS ester (0.25 mL) were combined in a separate reaction vessel and were mixed with rotation for 1 h at ambient temperature. The reaction mixture was purified by FPLC (MonoQ 10/100GL column, GE) using a pH and salt gradient. Fractions containing product were dialyzed and subsequently lyophilized, yielding DyLight550-PEG₄-alkane-3',5'-cytidine-bisphosphate (compound 14) as a dark pink residue.

Desthiobiotin-PEG$_n$ Modifications

Overview Preparation of DESTHIOBIOTIN-PEG₄-ALKANE-3',5'-CYTIDINE-BISPHOSPHATE (DP₄A-3',5'-pCp, Compound 17)

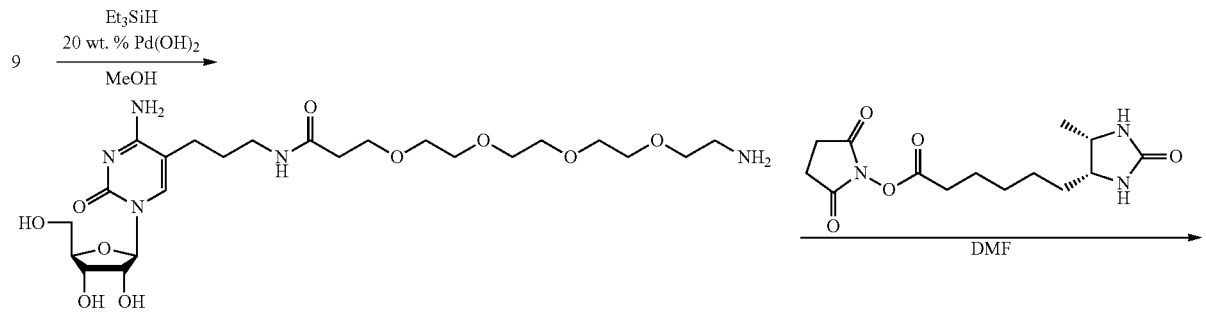

15

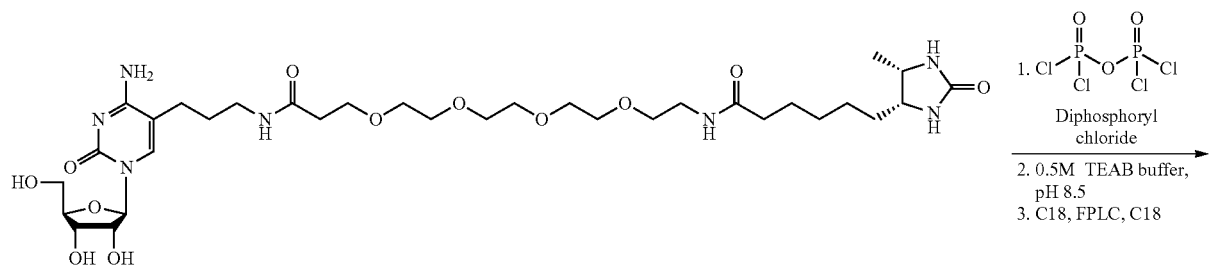

16

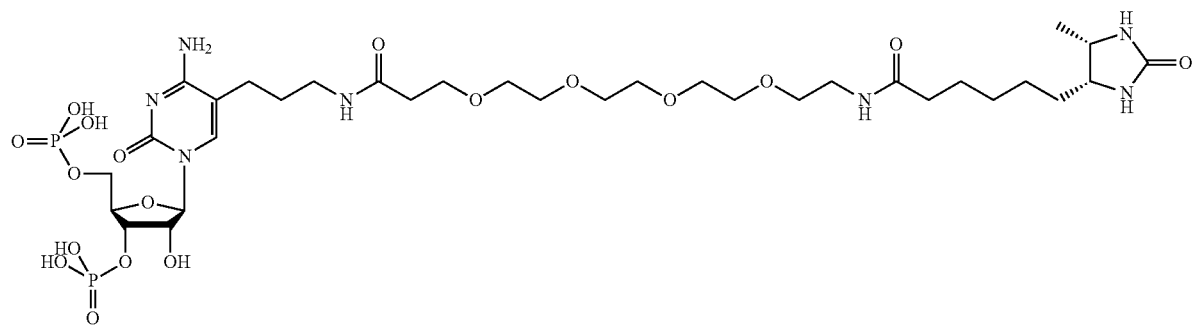

17

The reaction scheme to prepare desthiobiotin-polyethylene glycol (PEG)$_4$-alkane-3',5'-cytidine-bisphosphate was as follows. The azido-PEG$_4$-alkane-cytidine (compound 9) was reduced using triethylsilane and 20 wt % palladium hydroxide giving amino-PEG$_4$-alkane-cytidine (compound 15). The amino-PEG$_4$-alkane-cytidine (compound 15) was then reacted with NHS-desthiobiotin giving desthiobiotin-PEG$_4$-alkane-cytidine (compound 16). Desthiobiotin-PEG$_4$-alkane-cytidine was then reacted with diphosphoryl chloride giving desthiobiotin-PEG$_4$-alkane-cytidine-bisphosphate (compound 17).

Preparation of
AMINO-PEG$_4$-ALKANE-CYTIDINE (AmP$_4$AC, 15)

Azido-PEG$_4$-alkane-cytidine (9) (0.20 g, 0.349 mmol, 1.00 equiv.) was dissolved in methanol (6 mL). Palladium hydroxide (0.040 g, 20 wt./wt. % based on 9) and triethylsilane (0.406 g, 3.49 mmol, 10.00 equiv.) was added to the reaction mixture. After 20-24 hours at ambient temperature, the reaction mixture was filtered through a pad of glass fiber and the filtrate was concentrated under reduced pressure giving amino-PEG$_4$-alkane-cytidine (15) as an off-white residue (0.19 g, 99%) which was confirmed by $^1$H-NMR and used directly without further purification.

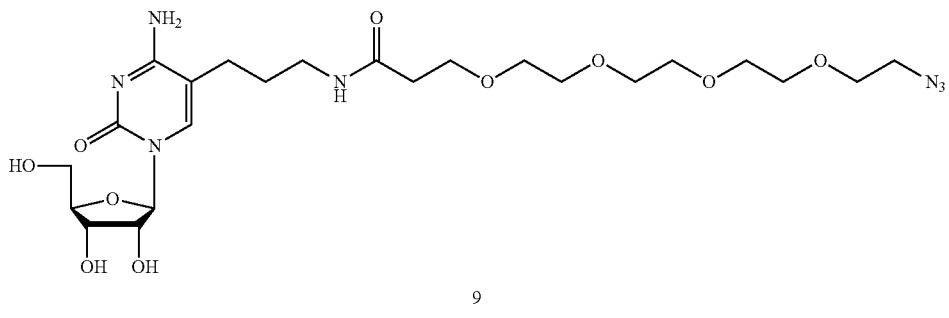

9
MW = 573.60
Azido-PEG$_4$-Alkane-Cytidine
(AzP$_4$AC)

Et$_3$SiH
20 wt. % Pd(OH)$_2$
MeOH

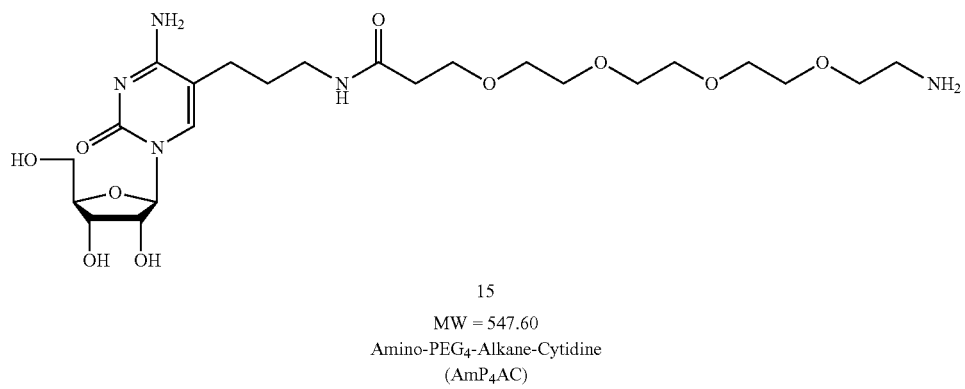

15
MW = 547.60
Amino-PEG$_4$-Alkane-Cytidine
(AmP$_4$AC)

Preparation of DESTHIOBIOTIN-PEG₄-ALKANE-CYTIDINE (DP₄AC, 16)

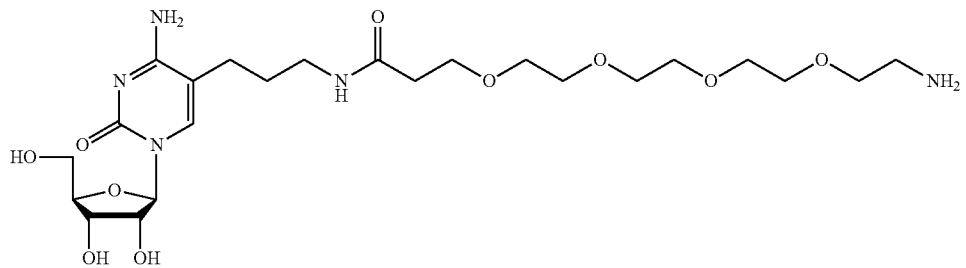

15
MW = 547.60
Amino-PEG₄-Alkane-Cytidine
(AmP₄AC)

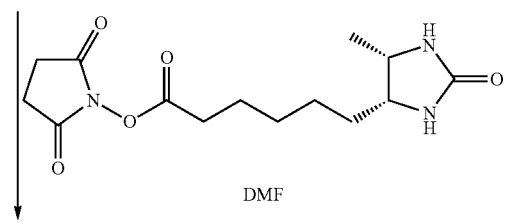

DMF

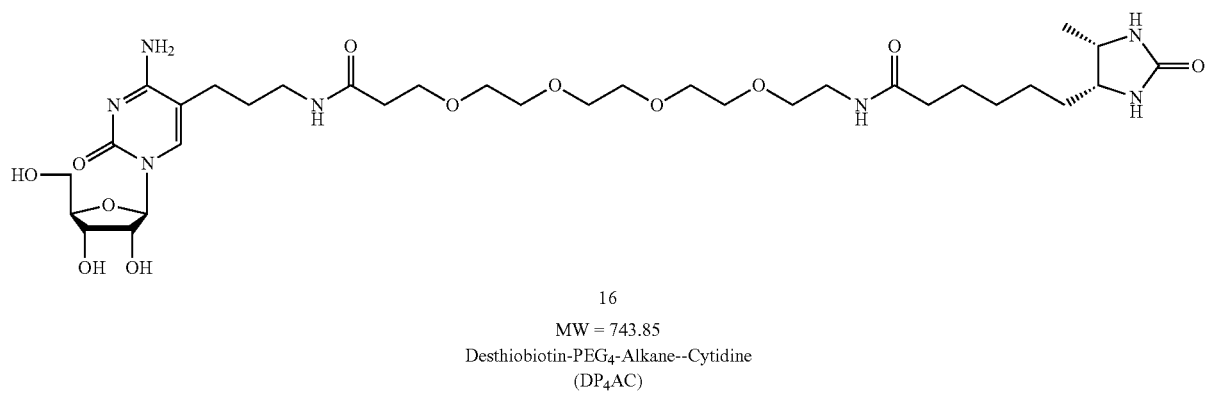

16
MW = 743.85
Desthiobiotin-PEG₄-Alkane--Cytidine
(DP₄AC)

NHS-desthiobiotin (0.102 g, 0.329 mmol, 1.00 equiv.) was added to a solution of amino-PEG₄-alkane-cytidine (15) (0.18 g, 0.329 mmol, 1.00 equiv.) in DMF (3 mL). The reaction solution was stirred at ambient temperature under N₂ atmosphere. After 20-24 h, the reaction mixture was concentrated under reduced pressure giving the crude product as a pale yellow residue. The crude product was purified by flash chromatography. Removal of solvent from the appropriate fractions gave desthiobiotin-PEG₄-alkane-cytidine (16) as a clear, near colorless glass (0.185 g, 76%) which was confirmed by $^1$H-NMR.

Preparation of DESTHIOBIOTIN-PEG$_4$-ALKANE-3',5'-CYTIDINE-BISPHOSPHATE (DP$_4$A-3',5'-pCp, 17)

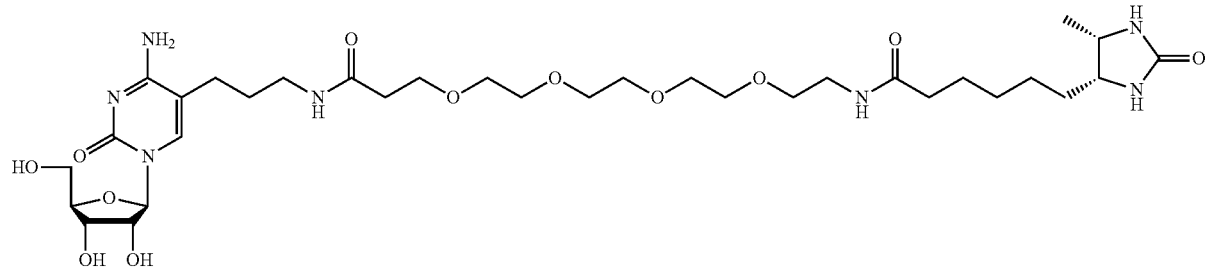

16
MW = 743.85
Desthiobiotin-PEG$_4$-Alkane-Cytidine
(DP$_4$AC)

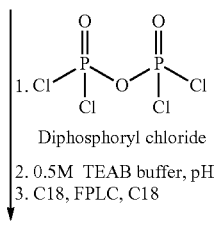

Diphosphoryl chloride 2. 0.5M TEAB buffer, pH 8.5
3. C18, FPLC, C18

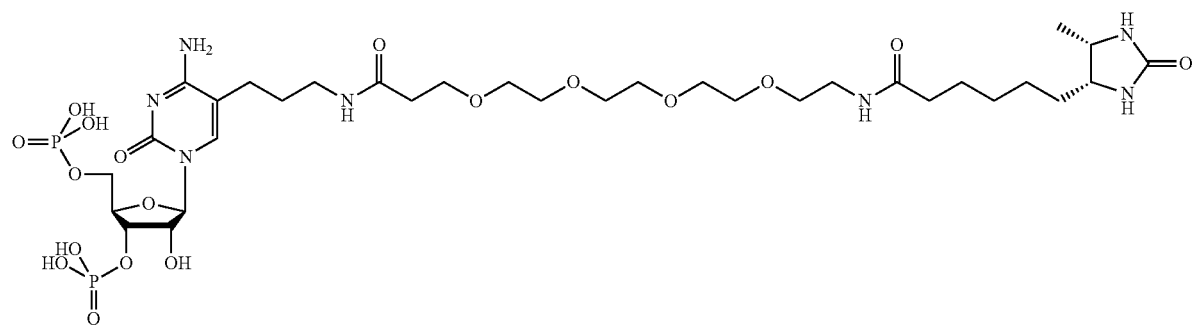

17
MW = 903.81
Desthiobiotin-PEG$_4$-Alkane-3',5'-Cytidine-Bisphosphate
(DP$_4$A-3',5'-pCp)

Desthiobiotin-PEG$_4$-alkane-cytidine (16) (0.117 g, 0.157 mmol, 1.00 equiv.) was partially dissolved in diphosphoryl chloride (391 μL, 3.30 mmol, 21.00 equiv.) in a 3 mL Reacti-Vial™. The mixture was then stirred at 0 to −10° C. After five hours, the reaction was quenched by the addition of ice cold ultra-pure water (1 mL) immediately followed by a solution of 0.5M TEAB buffer, pH 8.5 (23 mL). The colorless solution was stirred at ambient temperature for 30 min and then stored overnight at 0-5° C. The pH was adjusted to 3.0-3.5 and the solution was concentrated using a rotary evaporator until TEAB was complete removed. The solution was desalted using a C18 cartridge (Waters) and purified by FPLC (MonoQ 10/100GL column, GE). The purified product was subsequently desalted using a C18 cartridge (Waters) giving desthiobiotin-PEG$_4$-alkane-3',5'-cytidine-bisphosphate (17) as a clear glass (9 mg, 6%) after lyophilization. The structure was confirmed by $^1$H-NMR and HPLC.

Overview Preparation of DESTHIOBIOTIN-PEG$_{12}$-ALKANE-3',5'-CYTIDINE-BISPHOSPHATE (DP$_{12}$A-3',5'-pCp, Compound 21)
The reaction scheme to prepare desthiobiotin-polyethylene glycol (PEG)$_{12}$-alkane-3',5'-cytidine-bisphosphate was as follows. The 5-(3-aminopropyl)cytidine (compound 4) was
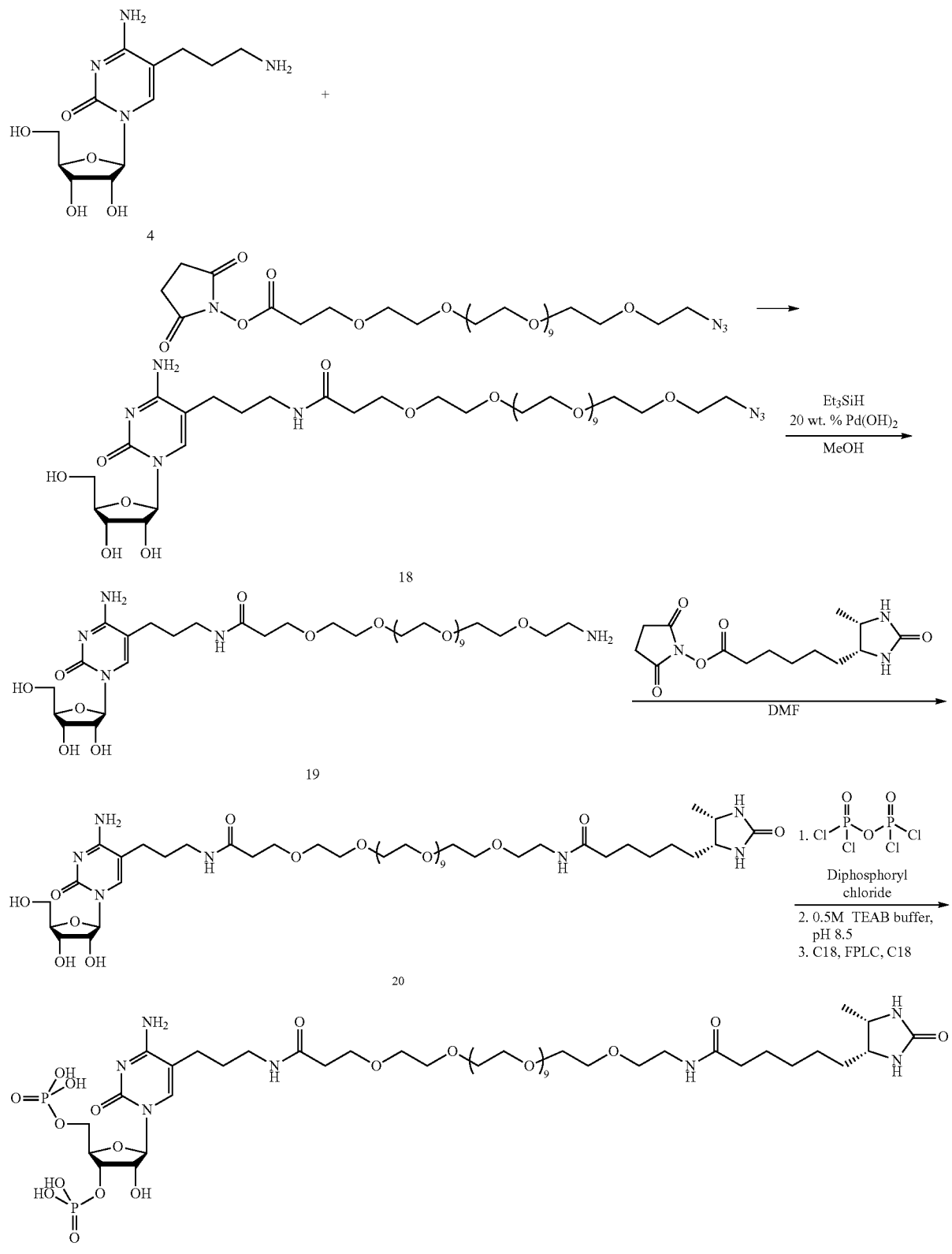

synthesized as described above, then was reacted with NHS-PEG$_{12}$-azide giving azido-PEG$_{12}$-alkane-cytidine (compound 18). The azido-PEG$_{12}$-alkane-cytidine (compound 18) was reduced using triethylsilane and 20 wt. % palladium hydroxide giving amino-PEG$_{12}$-alkane-cytidine (compound 19). The amino-PEG$_{12}$-alkane-cytidine (compound 19) was then reacted with NHS-desthiobiotin giving desthiobiotin-PEG$_{12}$-alkane-cytidine (compound 20). Desthiobiotin-PEG$_4$-alkane-cytidine was then reacted with diphosphoryl chloride giving desthiobiotin-PEG$_{12}$-alkane-cytidine-bisphosphate (compound 21).

NHS-PEG$_{12}$-azide (0.445 g, 0.607 mmol, 1.00 equiv.) was dissolved in DMF (10 mL). 5-(3-aminopropyl)cytidine (4) (0.182 g, 0.607 mmol, 1.00 equiv.) was added to the reaction solution as a solid. The reaction solution was stirred at ambient temperature under N$_2$ atmosphere. After 18-24 hours, the reaction mixture was concentrated under reduced pressure giving the crude product as a pale amber oil. The crude product was purified by flash chromatography. Removal of solvent from the appropriate fractions gave of azido-PEG$_{12}$-alkane-cytidine (18) as a clear, near colorless residue (0.35 g, 62%) the structure of which was confirmed by $^1$H-NMR.

Preparation of
AZIDO-PEG$_{12}$-ALKANE-CYTIDINE (AzP$_4$AC, 18)

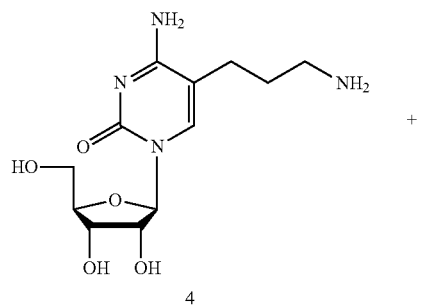

4
MW = 300.31
5-(3-aminopropyl)cytidine

+

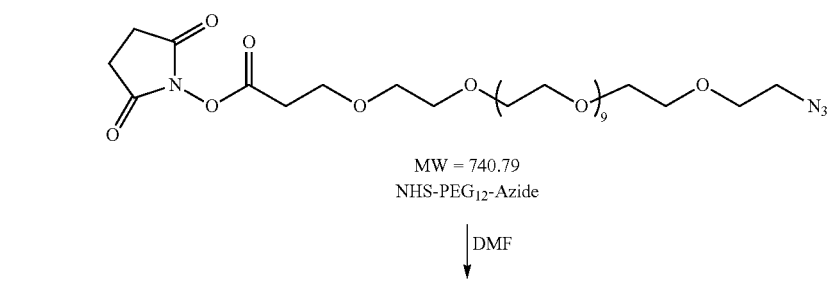

MW = 740.79
NHS-PEG$_{12}$-Azide

↓ DMF

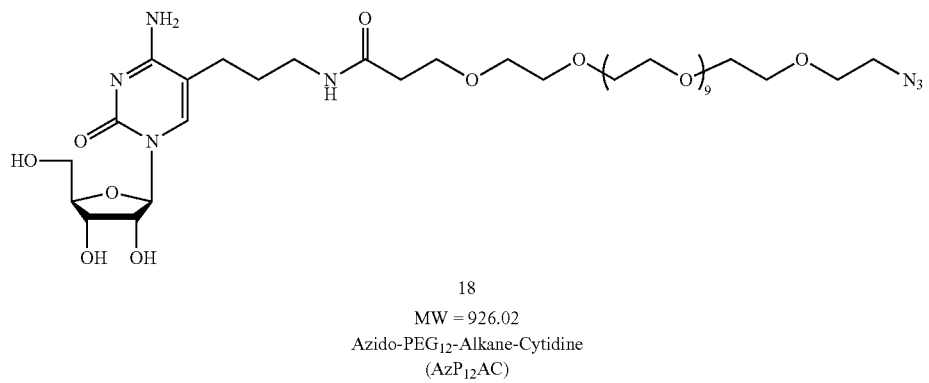

18
MW = 926.02
Azido-PEG$_{12}$-Alkane-Cytidine
(AzP$_{12}$AC)

Preparation of AMINO-PEG$_{12}$-ALKANE-CYTIDINE (AmP$_4$AC, 19)

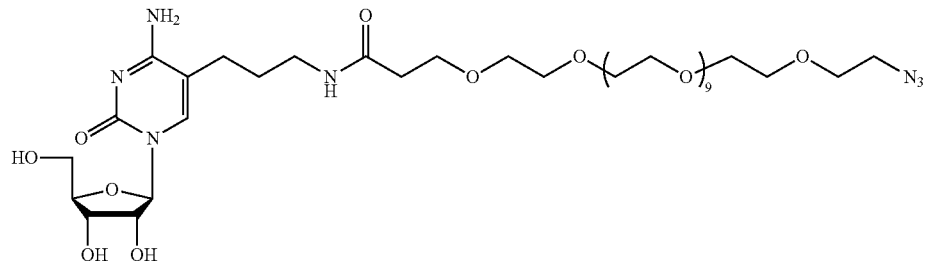

18
MW = 926.02
Azido-PEG$_{12}$-Alkane-Cytidine
(AzP$_{12}$AC)

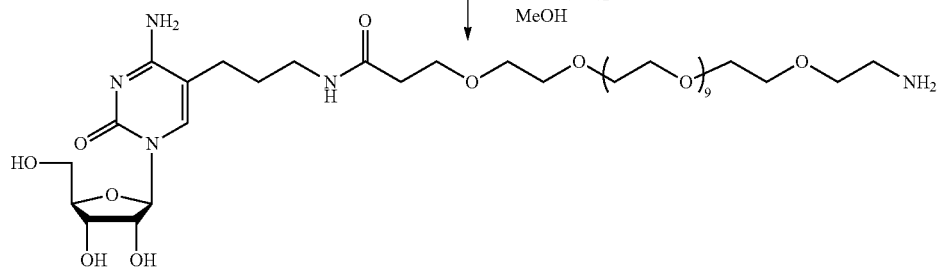

19
MW = 900.02
Amino-PEG$_{12}$-Alkane-Cytidine
(AmP$_{12}$AC)

Azido-PEG$_{12}$-alkane-cytidine (18) (0.10 g, 0.108 mmol, 1.00 equiv.) was dissolved in methanol (3 mL). Palladium hydroxide (0.020 g, 20 wt./wt. % based on 18) and triethylsilane (0.126 g, 1.08 mmol, 10.00 equiv.) was added to the reaction mixture. After 20-24 hours at ambient temperature, the reaction mixture was filtered through a pad of glass fiber and the filtrate was concentrated under reduced pressure giving amino-PEG$_{12}$-alkane-cytidine (19) as an clear, colorless residue (0.10 g, 100%) which was confirmed by $^1$H-NMR and used directly without further purification.

Preparation of DESTHIOBIOTIN-PEG$_{12}$-ALKANE-CYTIDINE (DP$_{12}$AC, 20)

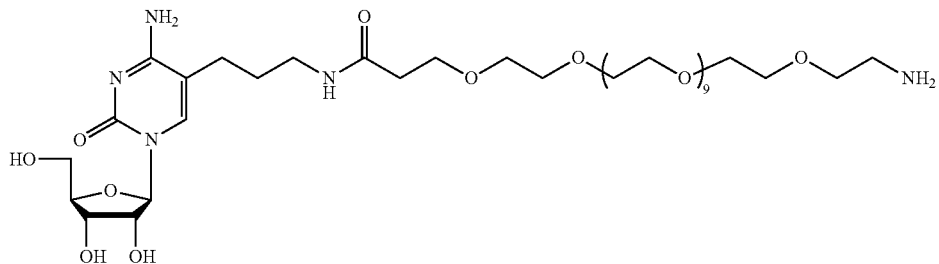

19
MW = 900.02
Amino-PEG$_{12}$-Alkane-Cytidine
(AmP$_{12}$AC)

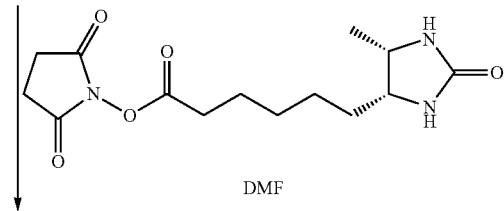

DMF

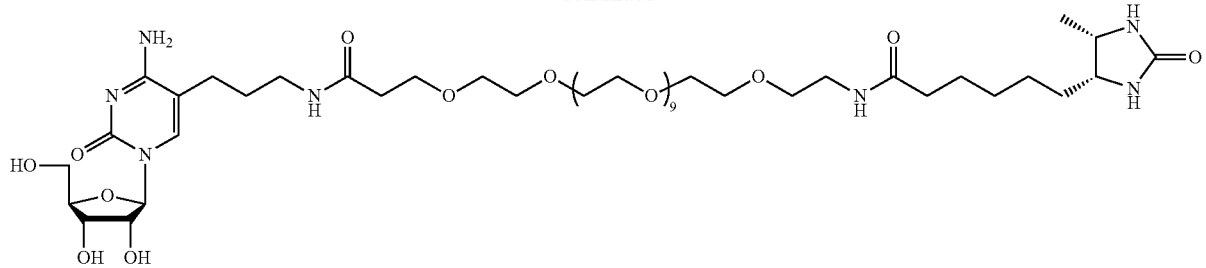

20
MW = 1096.27
Desthiobiotin-PEG$_{12}$-Alkane-Cytidine
(DP$_{12}$AC)

NHS-desthiobiotin (0.035 g, 0.111 mmol, 1.00 equiv.) was added to a solution of amino-PEG$_{12}$-alkane-cytidine (19) (0.10 g, 0.111 mmol, 1.00 equiv.) in DMF (2 mL). The reaction solution was stirred at ambient temperature under N$_2$ atmosphere. After 20-24 h, the reaction mixture was concentrated under reduced pressure giving the crude product as a pale yellow residue. The crude product was purified by flash chromatography. Removal of solvent from the appropriate fractions gave desthiobiotin-PEG$_{12}$-alkane-cytidine (20) as a clear, near light yellow glass (0.054 g, 44%) which was confirmed by $^1$H-NMR and used directly without further purification.

Preparation of DESTHIOBIOTIN-PEG$_{12}$-ALKANE-3',5'-CYTIDINE-BISPHOSPHATE (DP$_{12}$A-3',5'-pCp, 21)

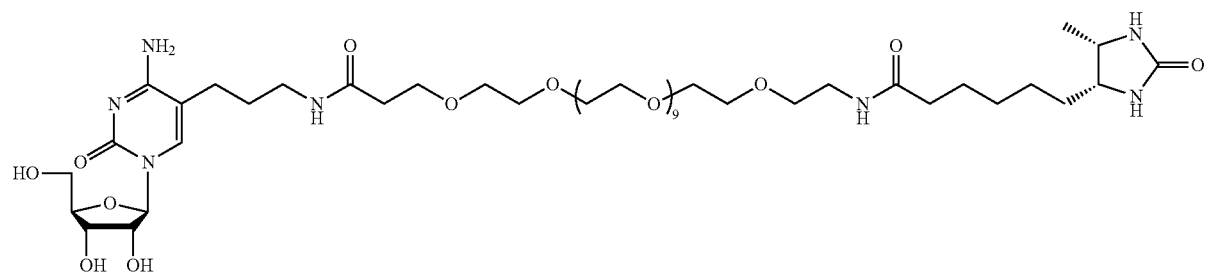

20
MW = 1096.27
Desthiobiotin-PEG$_{12}$-Alkane-Cytidine
(DP$_{12}$AC)

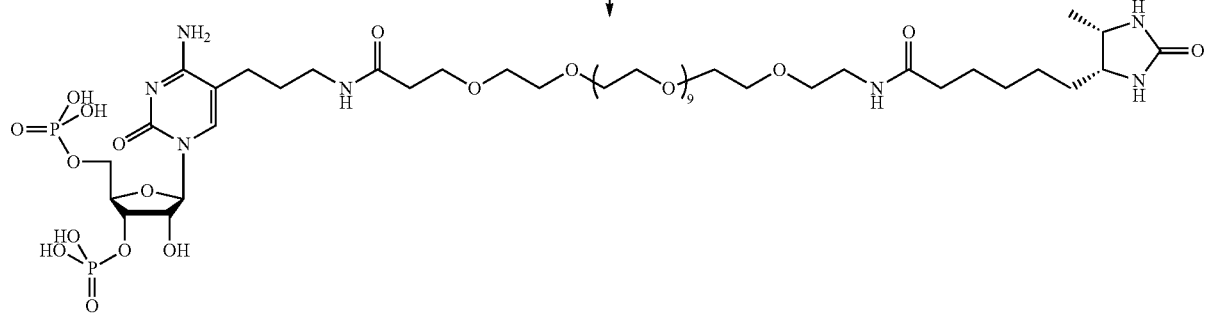

21
MW = 1256.23
Desthiobiotin-PEG$_{12}$-Alkane-3',5'-Cytidine-Bisphosphate
(DP$_{12}$A-3',5'-pCp)

Desthiobiotin-PEG$_{12}$-alkane-cytidine (20) (0.054 g, 0.049 mmol, 1.00 equiv.) was partially dissolved in diphosphoryl chloride (122 µL, 1.03 mmol, 21.00 equiv.) in a 3 mL Reacti-Vial™. The mixture was then stirred at 0° C. to 10° C. After about five hours, the reaction was quenched by adding ice cold ultra-pure water (1 mL) immediately followed by a solution of 0.5M TEAB buffer, pH 8.5 (11 mL). The colorless solution was stirred at ambient temperature for 30 min and then stored overnight at 0-5° C. The pH was adjusted to 3.0-3.5 and the solution was concentrated using a rotary evaporator until TEAB was completely removed. The solution was desalted using a C18 cartridge (Waters) and purified by FPLC (MonoQ 10/100GL column, GE). The purified product was subsequently desalted using a C18 cartridge (Waters) giving desthiobiotin-PEG$_{12}$-alkane-3',5'-cytidine-bisphosphate (21) as a clear glass (4 mg, 6%) after lyophilization. The structure was confirmed by $^1$H-NMR and HPLC.

Other exemplary compounds follow. Examples of fluorescent compounds include, but are not limited to, the following:

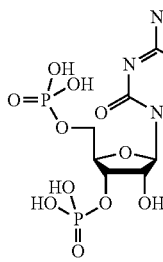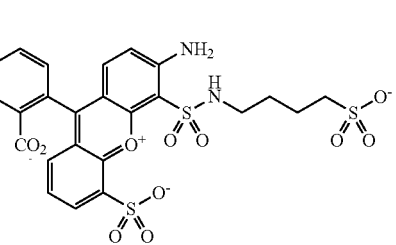

DyLight488-PEG$_4$-Alkane-3',5'-Bisphosphate-Cytidine
(Dy488P$_4$A-3', 5'-pCp)

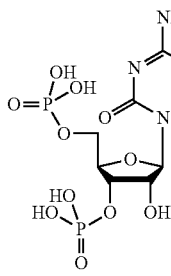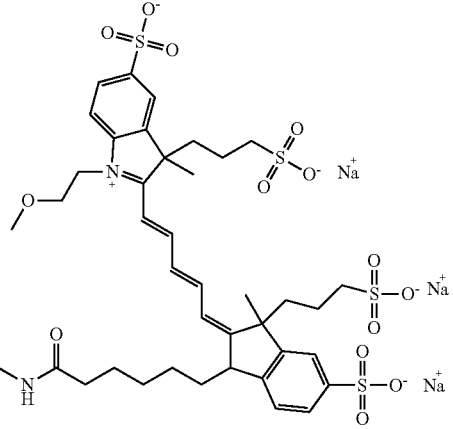

DyLight650-PEG$_4$-Alkane-3',5'-Bisphosphate-Cytidine
(Dy650P$_4$A-3', 5'-pCp)

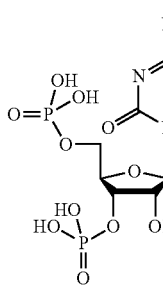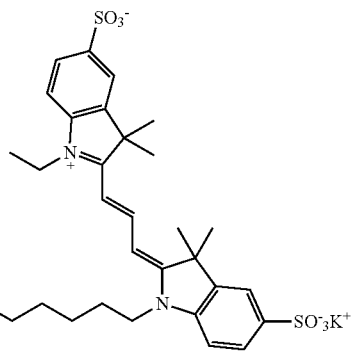

Cy3-PEG$_4$-Alkane-3',5'-Bisphosphate-Cytidine
(Cy3P$_4$A-3', 5'-pCp)

-continued
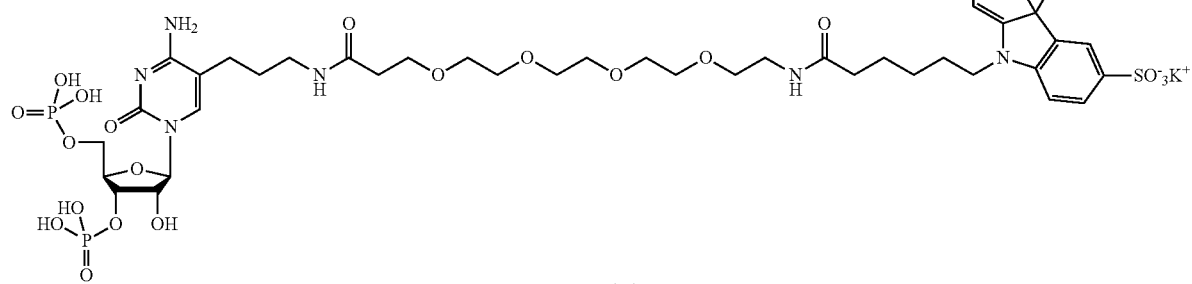
Cy5-PEG₄-Alkane-3′,5′-Bisphosphate-Cytidine
(Cy5P₄A-3′, 5′-pCp)
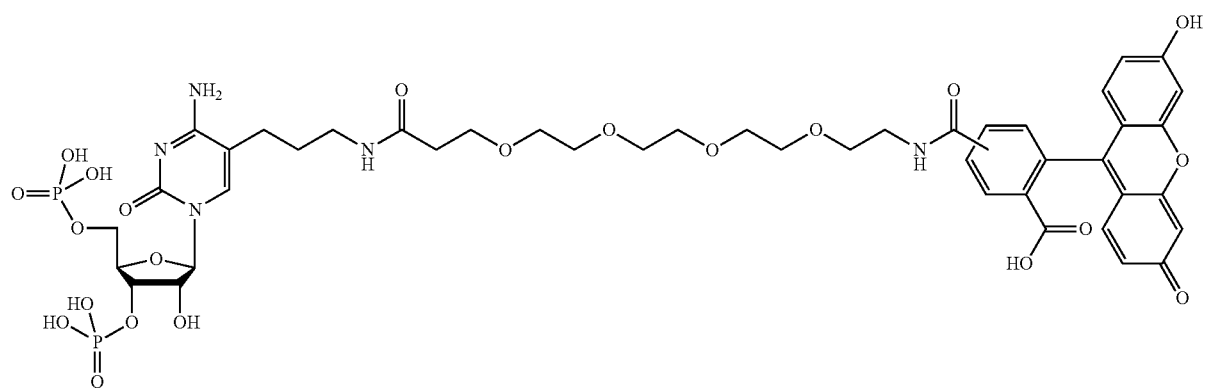
5/6-Carboxyfluorescein-PEG₄-Alkane-3′,5′-Bisphosphate-Cytidine
(5/6-FP₄A-3′,5′-pCp)
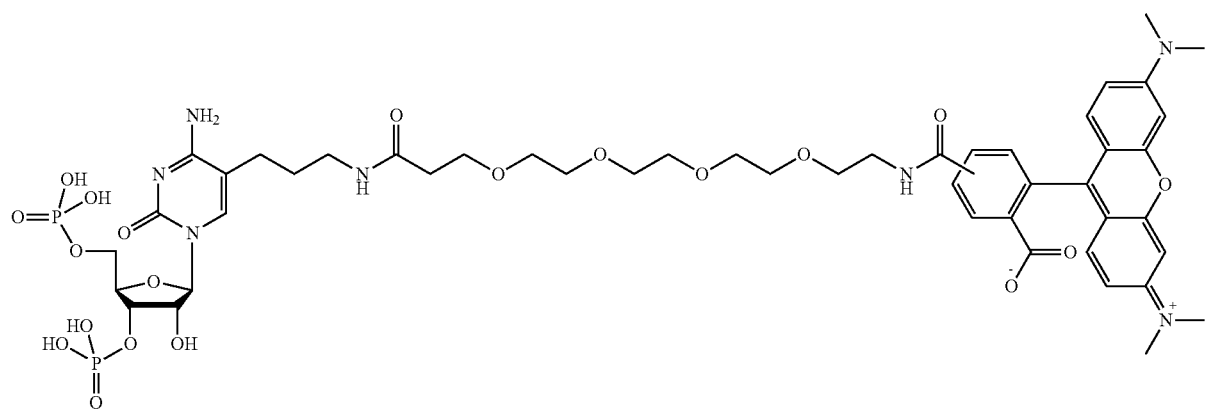
5/6-Carboxytetramethylrhodamine-PEG₄-Alkane-3′,5′-Bisphosphate-Cytidine
(5/6-FP₄A-3′,5′-pCp)

-continued

Examples of compounds with mass labels include, but are not limited to, the following:

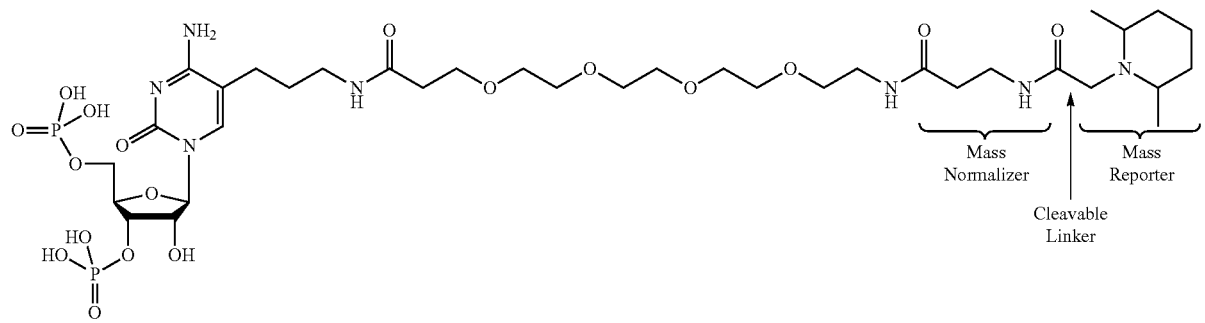

TMT-PEG$_4$-Alkane-3′,5′-Bisphosphate-Cytidine
(TMTP$_4$A-3′,5′-pCp)

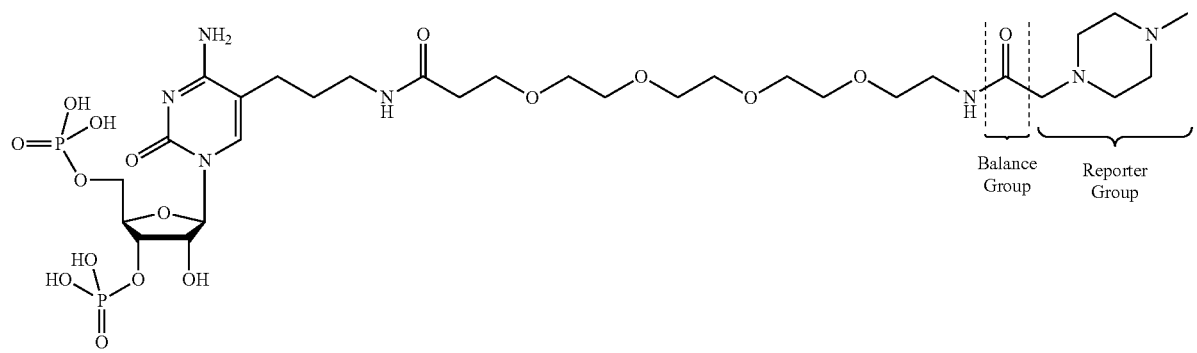

iTRAQ-PEG$_4$-Alkane-3′,5′-Bisphosphate-Cytidine
(iTRAQP$_4$A-3′,5′-pCp)

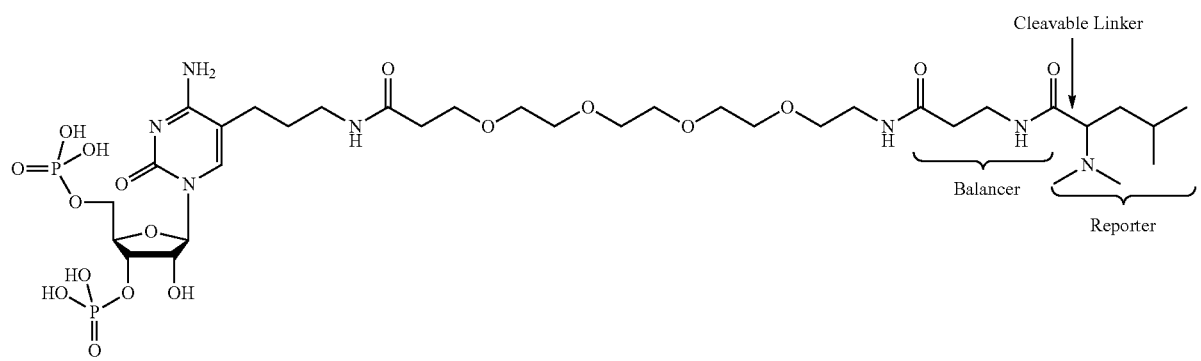

DiART-PEG$_4$-Alkane-3′,5′-Bisphosphate-Cytidine
(DiARTP$_4$A-3′,5′-pCp)

Examples of compounds with a spin label include, but are not limited to, the following:

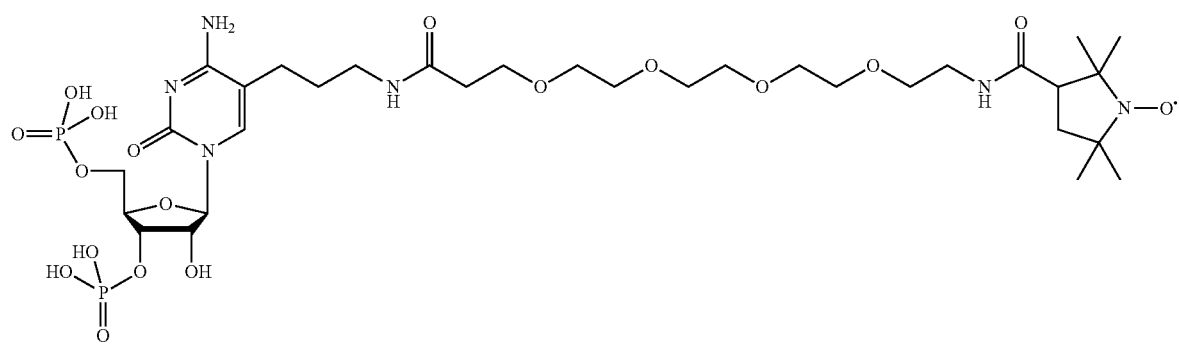

Proxyl-PEG$_4$-Alkane-3′,5′-Bisphosphate-Cytidine
(PP$_4$A-3′,5′-pCp)

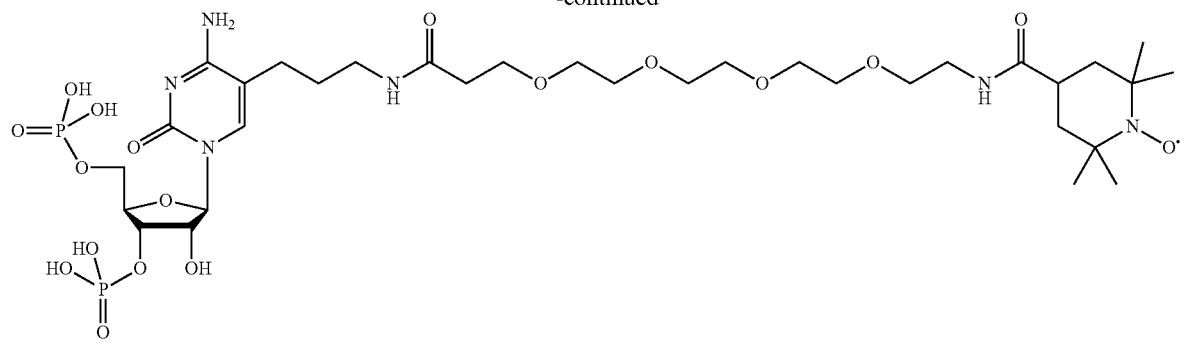

TEMPO-PEG₄-Alkane-3',5'-Bisphosphate-Cytidine
(TP₄A-3',5'-pCp)

Examples of a desthiobiotin-containing compound include, but are not limited to, the following:

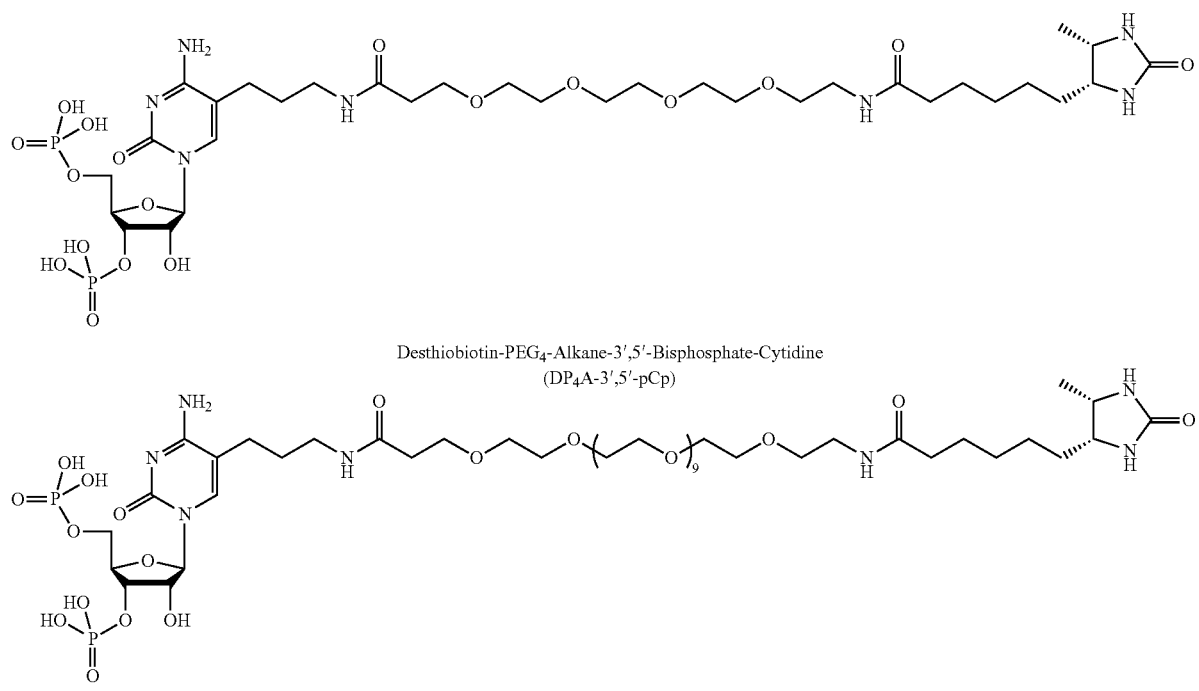

Desthiobiotin-PEG₄-Alkane-3',5'-Bisphosphate-Cytidine
(DP₄A-3',5'-pCp)

Desthiobiotin-PEG₁₂-Alkane-3',5'-Bisphosphate-Cytidine
(DP₁₂A-3',5'-pCp)

Examples of compounds with alternative cleavage include, but are not limited to, the following:

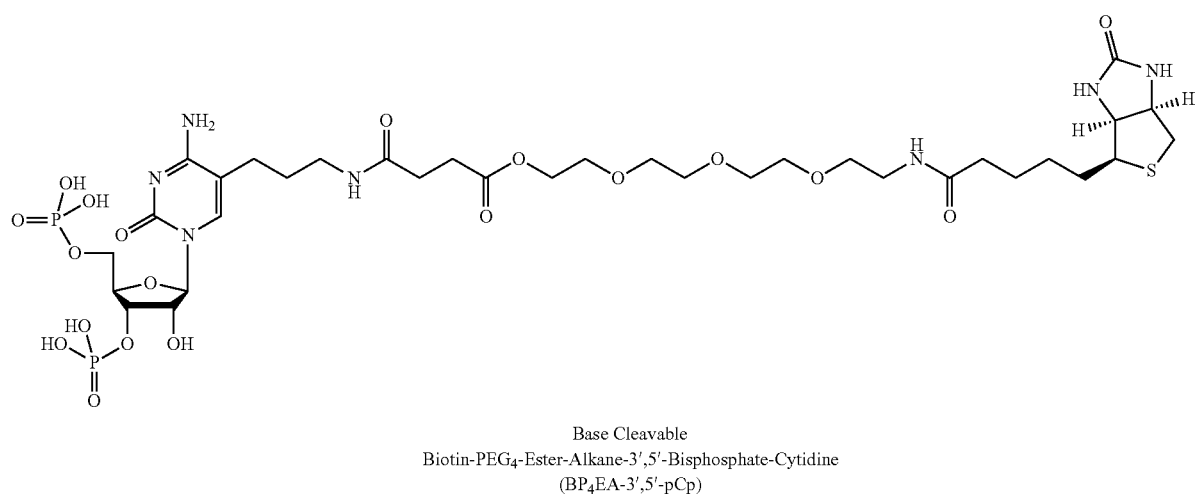

Base Cleavable
Biotin-PEG₄-Ester-Alkane-3',5'-Bisphosphate-Cytidine
(BP₄EA-3',5'-pCp)

-continued
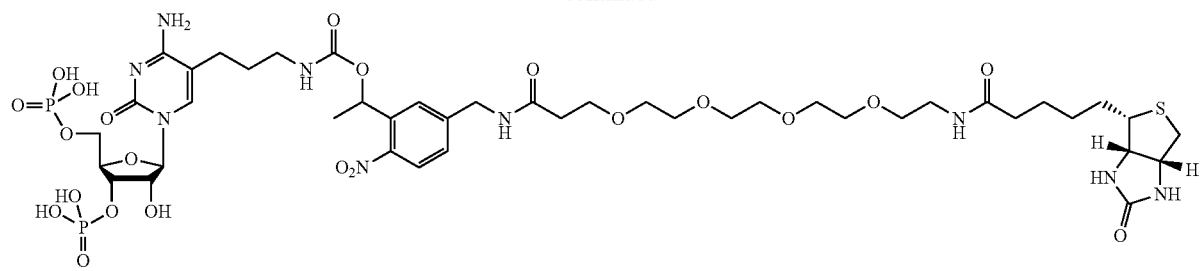
Photocleavable
Biotin-PEG₄-Photo-Alkane-3′,5′-Bisphosphate-Cytidine
(BP₄PA-3′,5′-pCp)
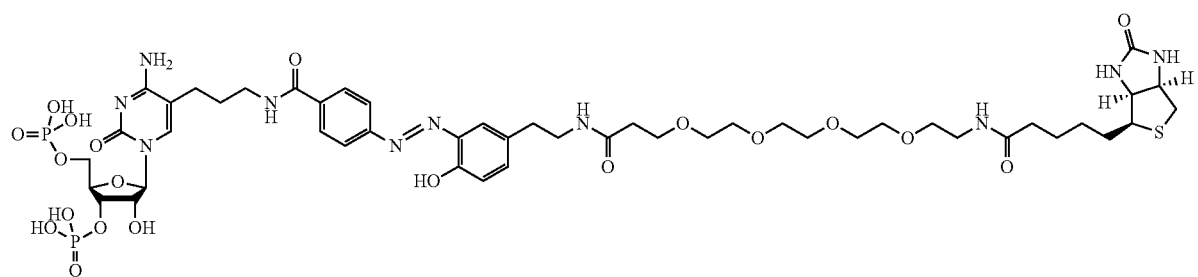
Reduction Cleavable
Biotin-PEG₄-NN-Alkane-3′,5′-Bisphosphate-Cytidine
(BP₄NNA-3′,5′-pCp)
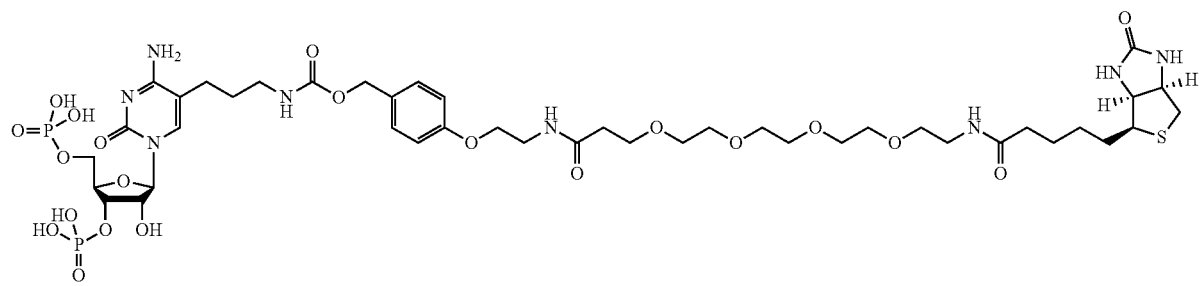
Acid Cleavable
Biotin-PEG₄-Acid-Alkane-3′,5′-Bisphosphate-Cytidine
(BP₄AA-3′,5′-pCp)
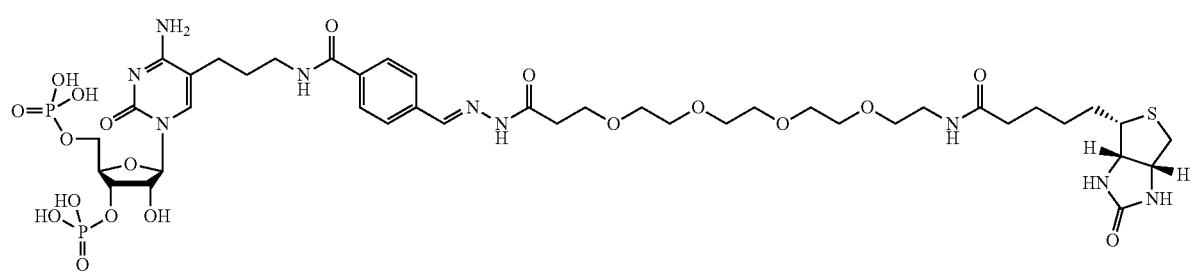
Hydrazone Exchange Cleavable
Biotin-PEG₄-Hydrazone-Alkane-3′,5′-Bisphosphate-Cytidine
(BP₄HA-3′,5′-pCp)

Examples of compounds with photo-reactive group include, but are not limited to, the following:

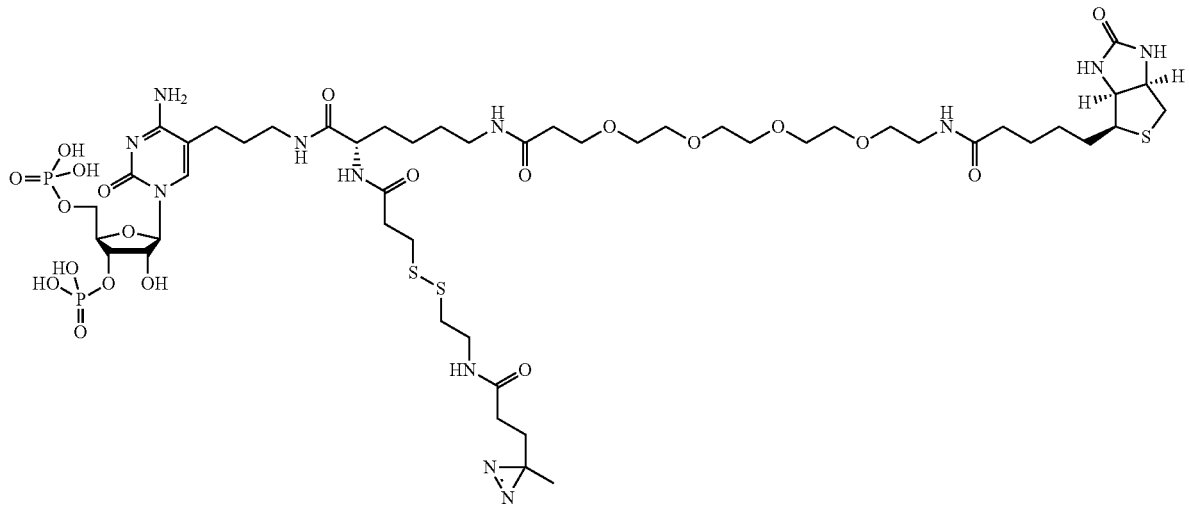

Trifunctional with Cleavable, Photo-Reactive Crosslinker
Biotin-PEG₄-Lysine-SS-Diazirine-Alkane-3',5'-Biophosphate-Cytidine
(BP₄LSSDA-3',5'-pCp)

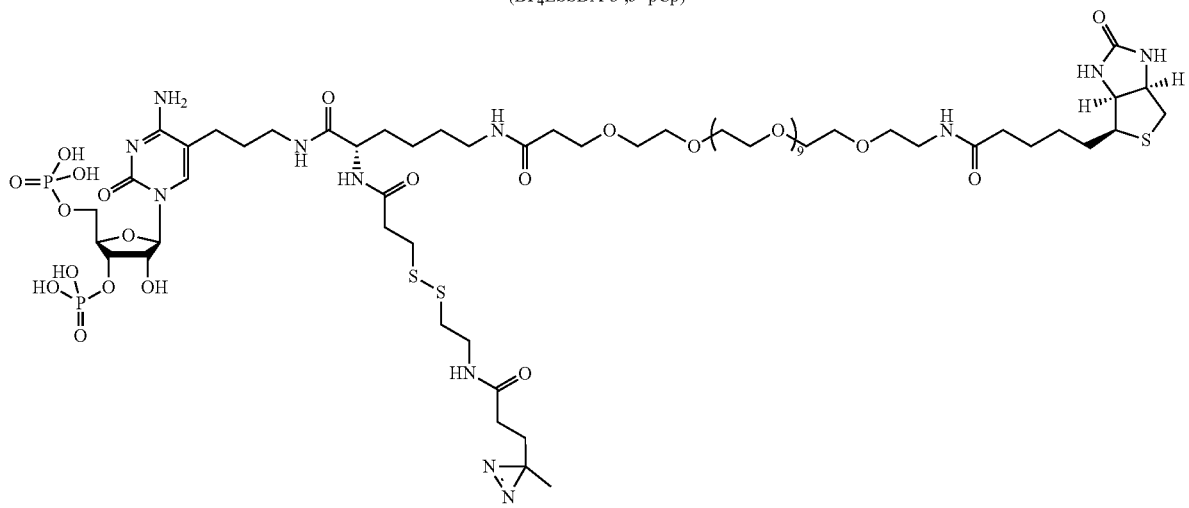

Trifunctional with Cleavable, Photo-Reactive Crosslinker
Biotin-PEG₁₂-Lysine-SS-Diazirine-Alkane-3',5'-Biophosphate-Cytidine
(BP₁₂LSSDA-3',5'-pCp)

The following examples are intended to illustrate the utility of the present invention but do not limit the claim scope:

EXAMPLE 1

In the experiments subsequently described, T4 RNA ligase was used to label RNA with biotinylated cytidine 3',5' bisphosphate. Several molecules were synthesized to optimize the nucleotide for optimal ligation efficiency and functionality, for example, preservation of the interaction of the labeled RNA with other RNA or cellular proteins. Three different alkyl linkages were tested, including alkyne, alkene, and alkane, in combination with both LC (long chain), SC (short chain), and PEG spacers, as shown in FIGS. 1-3. The molecules were tested for ligation efficiency and functionality utilizing established electrophoretic mobility shift assay (EMSA) controls. In a mobility shift assay, labeled RNA probe is incubated with a cell lysate containing the protein(s) of interest in a binding reaction. The reaction is then electrophoresed on a non-denaturing gel. Unbound probe will migrate to the bottom of the gel, while protein bound probe will migrate more slowly, resulting in a bandshift. The alkyne-LC- and alkyne-SC-containing nucleotides ligated with good efficiency; however, the alkyne linkage was reactive in cell lysates. In a purified system using an RNA polymerase template and purified RNA polymerase, the alkyne compounds produced a functional gel shift (FIG. 4 A), while the alkyne compound did not produce a functional gel shift with the iron responsive element (IRE)-iron responsive protein (IRP) control utilizing cytosolic liver extract (FIG. 4B). When the liver extract was mixed with purified RNA polymerase, the bandshift was affected, suggesting that the alkyne compound is reactive with liver extract (FIG. 4C). Similar results were obtained with the alkene compounds, where the IRE-IRP control ligated, but did not produce a functional bandshift (FIG. 5). The nucleotide containing the alkane linkage and PEG spacer was the most optimal compound for both ligation efficiency and functionality (FIG. 6).

Utilizing the biotin-PEG4-alkane 3,5 cytidine bisphosphate molecule, optimal ligation conditions were determined. The conditions described resulted in ligation efficiencies greater than 70%, and in some cases greater than 90%, depending upon the RNA secondary structure and ligation conditions. A standard reaction had a donor to acceptor ligation ratio of greater than 20:1. The reaction buffer contained 20 U to 40 U T4 RNA ligase, 40 U RNase inhibitor, 50 mM Tris-HCl, 10 mM $MgCl_2$, 10 mM DTT, 1 mM ATP (pH 7.8 at 25° C.), and 15% polyethylene glycol (PEG, MW 20,000). To achieve ligation efficiencies greater than 70%, reactions were incubated at 37° C. for 30 minutes, or at 16° C. from 30 minutes to 24 hours, depending upon the RNA length and secondary structure. In one embodiment, reactions contained 25 pmol to 50 pmol RNA, 1 nmol biotinylated nucleotide, and 20 U to 40 units of T4 RNA ligase in a 30 µl reaction volume. An excess of biotinylated nucleotide did not affect ligation efficiencies, and a range 1 pmol RNA to 200 pmol of RNA was tested in the ligation reaction. The concentration of PEG ranged from 5% to 20%.

As shown in the table below, the ligation conditions were assessed utilizing several RNA species, ranging in length, complexity, and function to demonstrate efficiency of ligation reaction using RNA of varying complexity and length. RNA was derived from the 3' untranslated regions (UTR) of mRNA 28-42 nucleotides, miRNA (22-80 nucleotides), and catalytic RNA (451 nucleotides). RNA was derived synthetically, or from in vitro transcription reactions.

| Description | RNA source | Length (bases) | Optimal reaction conditions |
| --- | --- | --- | --- |
| IRE (iron responsive element) | 5' or 3' UTR element | 28 | 2 hrs 16 C |
| RNA polymerase template RNA | RNA | 42 | 30 minutes, 37° C. >1 hr 16° C. |
| mir-16-1 | mature micro RNA | 22 | ON 16° C. |
| TNF ARE | 3' UTR element | 37 | 2 hrs 16° C. |
| Let-7 | pre-miRNA | in vitro transcribed | ~70 | overnight 16° C. |
| hTR | catalytic RNA | in vitro transcribed | 451 | overnight 16° C. |
| COX-76 ARE | 3' UTR element | in vitro transcribed | ~70 | overnight 16° C. |
| mir-16-1 | pre-miRNA | in vitro transcribed | ~70 | overnight 16° C. |

Ligation efficiencies were greater than 70% with reactions using 25-50 pmol RNA, 1 nmol biotinylated nucleotide, 20-40 U T4 RNA ligase, 40 U RNase Inhibitor, 50 mM Tris-HCl, 10 mM $MgCl_2$, 10 mM DTT, 1 mM ATP (pH 7.8 at 25° C.), and 15% PEG (MW 20,000). Ligation efficiencies were improved for RNAs with extensive RNA secondary structure or length by heating briefly before the ligation reaction; heating temperatures ranged from 80° C.-90° C. for 1-5 minutes, followed by rapid-cooling on ice for at least 1 minute to several hours. In some cases, adding 25% DMSO before heating enhanced ligation efficiency. The order of addition of the reaction components did not matter, except for the PEG, which was added last. Several PEG varieties were tested including molecular weights of 1500, 6000, 8500, and 20,000. Although the PEG (MW 20,000) best enhanced ligation efficiency, the other PEG molecules were acceptable, and other size exclusion molecules would also be acceptable. A PEG concentration of 15% was optimal. Other PEG concentrations could also be used, ranging from 5% to 20%.

Ligation efficiencies were assessed using dot blot and quantitative spot densitometry. A synthetically biotinylated RNA was used as a control where 100% biotinylation was assumed. Labeled RNA from the ligation reaction and the synthetically labeled RNA were first normalized to concentration, and then serially diluted to determine efficiency. A small volume was applied (spotted) onto a positively charged nylon membrane. The membrane was cross-linked using ultraviolet (UV) radiation. Biotinylated RNA was detected using a streptavidin horseradish peroxidase (HRP) substrate and chemiluminescent detection. The non-saturating spots, which are spots where the densitometry intensity value was not saturated, were quantitated using densitometry. To determine ligation efficiency, labeled RNA was compared to the control standard to determine efficiency. To determine labeling reproducibility, samples were applied (spotted) in triplicate for two of the RNA samples for intra-assay variability, and each ligation with the optimized conditions was repeated at least three independent times for interassay variability. To determine labeling integrity, labeled RNA was separated by electrophoresis on a gel containing 5% acrylamide/8 M urea (denaturing gel), the RNA was transferred to a nylon membrane and was detected using chemiluminescence. The results indicated that the labeled probes were of high quality, of the correct size, and exhibited either minimal degradation or no degradation.

In vitro transcribed RNA was derived through transcription from a digested plasmid containing the sequence of interest flanked by a T7 polymerase binding site and restriction enzyme site such that only the RNA of interest is transcribed. In vitro transcribed RNA was also derived through transcription of complementary primers containing a T7 RNA polymerase binding sequence element. Digested plasmid was purified by extraction with phenol:chloroform and ethanol precipitation. Complementary primers were annealed in a reaction containing 25 µM of each primer in 10 mM HEPES buffer (pH 7.3). Reactions were incubated at 95° C. for ten minutes followed by slow cooling at room temperature for at least ten minutes, followed by incubation on ice. Transcription reactions typically contained 500 ng-1 µg DNA, 0.5 mM each of ATP, CTP, UTP, and GTP, 1× transcription buffer, 30 U T7 RNA polymerase, and 40 units RNAse inhibitor. Reactions were incubated for 30 minutes to 1 hour at 37° C. DNA was digested for ten minutes with RNAse-free DNAse I at 37° C., followed by inactivation with EDTA. RNA was then selectively precipitated with ethanol, and transcript purity was determined by either agarose or non-denaturing polyacrylamide gel electrophoresis. Precipitated RNA was then quantitated by UV-spectroscopy (absorbance at 260 nm/280 nm), and 25 pmol-50 pmol of RNA was used in each ligation reaction.

EXAMPLE 2

The functionality of the labeled RNA was determined by assaying a known interaction of the RNA to ensure that the 3'-end label minimally disturbed secondary structure. Functionality of labeled iron responsive element (IRE), RNA polymerase template, and let-7 micro RNA was determined by RNA electrophoretic mobility shift assay (EMSA). The protein sources included cytosolic liver extract containing iron responsive element-iron responsive protein (IRE-IRP), lin-28 overexpression lysate (let-7-lin28), and purified RNA core polymerase (Epicentre). Dilutions of each RNA (nM) were incubated with the protein of interest in a 1× binding reaction containing 10 mM HEPES (pH 7.3), 20 mM KCl, 1 mM MgCl$_2$, 1 mM DTT, 2.5-10 µg tRNA, and 5% glycerol for 15-30 minutes at room temperature (about 20° C. to about 22° C.). Optimal binding conditions were achieved for RNA polymerase template by substituting tRNA with bovine serum albumin (BSA), and increasing the DTT concentration to 3 mM and the KCl concentration to 40 mM for the let-7-lin28 interaction. Binding reactions composition were separated by electrophoresis on native 6% acrylamide DNA retardation gels for one hr, 100 V, at either room temperature or 4° C. The RNA was then transferred to a positively charged nylon membrane, cross-linked (UV irradiation), and then detected using chemiluminescence. Three binding reactions were assessed for each labeled RNA: 1) migration and intensity of the free probe that migrated toward the bottom of the gel; 2) intensity of the labeled RNA with protein, resulting in a bandshift of the RNA-protein complex; and 3) the competition reaction of the labeled RNA and the unlabeled RNA with protein (FIG. 6). Each bandshift reaction was repeated three times with three independently labeled RNAs. Each of the 3 end-labeled probes was able to functionally bind its respective proteins and produce a robust bandshift, as shown for RNA template-RNA polymerase interaction (FIG. 6A), IRE-IRP interaction (FIG. 6B), and let-7-lin28 interaction (FIG. 6C). Each probe was also functional at the nanomolar level, indicating that the 50 pmol labeling reaction was sufficient for EMSA studies.

EXAMPLE 3

In one embodiment, biotin, a mass tag, or other suitable moiety containing an alkane linkage and PEG$_4$ spacer, known by one skilled in the art, on the labeled nucleotide serves as an affinity handle for isolating RNA:protein complexes. The functionality of a described biotin-labeled RNA to serve as an affinity handle for isolating RNA complexes (containing RNA, DNA, RNA and DNA, or protein) using an affinity resin, bead, or sensor chip (e.g., pull-down) was determined using streptavidin agarose resin and surface plasmon resonance.

IRE-RNA (SEQ ID NO: 1) was labeled using biotin PEG$_4$-alkane-3'5'-bisphosphate cytidine, and T4 RNA ligase. The IRP protein, which binds IRE RNA sequences, was cloned into a vector containing an HA tag and in vitro translated using an human cell-free human in vitro transcription/translation system. Before incubation with the biotinylated RNA, the IRP lysate was incubated with streptavidin agarose resin to reduce non-specific binding, and to remove endogenous biotin. The IRP lysate was then incubated with the labeled IRE, or with a non-specific control RNA (SEQ ID NO: 2) which was 3'-labeled with biotin, in binding buffer (10 mM HEPES pH 7.3, 20 mM KCl, 1 mM MgCl$_2$, 1 mM DTT, 10% glycerol, 40 U RNase inhibitor (RNasin®)) for 30 minutes at room temperature, and was then cross-linked with UV light (254 nm) for 10 minutes on ice. Binding reactions were then washed with PBS and the IRE-IRP complex was eluted from the resin. After separation by electrophoresis and transfer to a membrane, IRP was detected using mouse anti-HA antibody. The results are shown in FIG. 7. Lane 1 is 5 µl HA-IRP IVT lysate, lane 2 is 25 µl flow-through fraction, lane 3 is 50 µl wash fraction, and lane 4 is 25 µl eluted fraction.

The ability of the biotin-labeled RNA to enrich for RNA:protein complexes using an immobilized streptavidin sensor chip was examined using Biacore™ Surface Plasmon Resonance (SPR). The results are shown in FIG. 8 where the solid line is control mRNA and the dashed line is a reference (flow cell 1); and where A=biotinylated RNA template control loading; B=RNA Pol II injection; C=RNA Pol II bound to control RNA; and D=injection of unlabeled control RNA. Biotin-labeled control RNA was captured on a Streptavidin-coated sensor chip followed by injection of bacterial RNA Polymerase. A binding response of RNA polymerase II was detected on the active RNA surface and specificity was confirmed by the loss of binding after injection of non-labeled control RNA. Twenty pmol labeled RNA was diluted into nuclease-free HEPES buffer (pH 7.3), injected at 5 l/min for four minutes, and captured onto a commercially purchased streptavidin-coated sensor chip for the Biacore 3000®. Bacterial RNA polymerase (0.1 U/µl) was then injected for two minutes. As shown in FIG. 8, a binding response of RNA polymerase II was detected on the active RNA surface and specificity was confirmed by loss of binding after injecting non-labeled control RNA. Specificity was determined through competition of binding RNA polymerase with a 50-100 fold excess of non-labeled RNA polymerase template RNA that was injected for four minutes.

Poly(A)$_{25}$ RNA was labeled using desthiobiotin-PEG$_4$-alkane-3'5'-bisphosphate cytidine and T4 RNA ligase. The Poly(A) Binding Protein (PABP), which binds the poly(A) tracts of mRNA is ubiquitous and readily detectable in cell culture lysates. The labeled RNA (50 pmol) was incubated with streptavidin magnetic beads (0.5 mg) for thirty minutes in 20 mM Tris-HCl (7.5), 100 mM NaCl, 1 mM EDTA. After washing, the beads were then incubated with 100 mg of HEK 293 cell lysate in Binding Buffer (10 mM Tris-HCl, pH 7.5, 2.5 mM MgCl$_2$, 10 mM KCl, 15% glycerol, 0.5% Tween-20, and 10 µg tRNA) for one hour at 4° C. An unrelated RNA was used as a negative control, and beads were incubated with lysate alone to assess background. Beads were washed in 20 mM Tris-HCl (7.5), 10 mM NaCl, 0.5% Tween-20, and protein was eluted by heating at 95° C. for 5-10 minutes using 1× reducing sample buffer, or eluting with 4 mM biotin in 20 mM Tris (7.5). After separation by electrophoresis, PABP was detected using PABP antibody.

The results are shown in FIGS. 14 and 15. Synthetic RNA (50 pmol/reaction) was end-labeled using a twenty-fold excess of desthiobiotin-PEG$_4$-alkane-3'5'-bisphosphate cytidine with T4 RNA ligase. Labeled RNA was incubated with 0.5 mg streptavidin magnetic beads for thirty minutes at room temperature. Beads were then washed 2× in 20 mM Tris (7.5). For the binding reaction, HEK 293 cell lysate (100 µg) were incubated with RNA-containing beads (both positive and negative controls), or base beads in 1× binding buffer (PABPC1-10 mM Tris (7.5), 2.5 mM MgCl$_2$, 10 mM KCl, 15% glycerol, 0.5% Tween-20, 10 µg tRNA; SNRPA1-10 mM Tris (7.5), 250 mM NaCl, 1 mM EDTA, 0.5% Tween-20, and 10 µg tRNA) for 1 hour at 4° C. Beads were washed 3× in 20 mM Tris (7.5), 10 mM NaCl, 0.5% Tween-20. Complexes were eluted using 2× reducing sample buffer. Normalized samples were separated by electrophoresis, transferred, and detected using PABPC1, GST (SNRPA1) antibodies (1:1000 dilution in TBST-0.5% BSA). Exposure time—1 minute. FT flow-through; 1,2,3—washes, E—elution. RNA used for pull-downs are labeled above respective blots. Lane 1—flow-through (40 μl), Lanes 2-4—washes (40 μl), Lane 5 elution (20 μl).

EXAMPLE 4

In one embodiment, biotin or other suitable moiety containing n alkane linkage and $PEG_{12}$ spacer, known by one skilled in the art, on the labeled nucleotide serves as an affinity handle for isolating RNA:protein complexes. The functionality of a described biotin-labeled RNA to serve as an affinity handle for isolating RNA complexes (containing RNA, DNA, RNA and DNA, or protein) using an affinity resin, was determined using streptavidin magnetic beads.

Poly(A)$_{25}$ RNA was labeled using biotin-$PEG_{12}$-alkane-3'5'-bisphosphate cytidine and T4 RNA ligase. The Poly(A) Binding Protein (PABP), which binds the poly(A) tracts of mRNA, was cloned into a vector containing a GST-tag and expressed in a human cell-free in vitro translation (IVT) system. The lysate was diluted 1:10 for use in the binding reaction. The labeled RNA (50 pmol) was incubated with streptavidin magnetic beads (0.5 mg) for thirty minutes in 20 mM Tris-HCl (7.5), 100 mM NaCl, 1 mM EDTA. After washing, the beads were then incubated with 2-3 μl of diluted IVT lysate cell lysate in Binding Buffer (10 mM Tris-HCl, pH 7.5, 2.5 mM $MgCl_2$, 10 mM KCl, 15% glycerol, 0.5% Tween-20, and 10 μg tRNA) for one hour at 4° C. An unrelated RNA was used as a negative control, and beads were incubated with lysate alone to assess background. Beads were washed in 20 mM Tris-HCl1 (7.5), 10 mM NaCl, 0.5% Tween-20, and protein was eluted by heating at 95° C. for 5-10 minutes using 1× reducing sample buffer, or eluting with 4 mM biotin in 20 mM Tris (7.5). After separation by electrophoresis, PABP was detected using PABP antibody.

Results are shown in FIG. 16. Synthetic RNA (50 pmol/reaction) was end-labeled using a twenty-fold excess of Biotin-$PEG_{12}$.Alkane-3'5'-Bisphosphate Cytidine with T4 RNA ligase. Labeled RNA was incubated with 0.5 mg of streptavidin magnetic beads for thirty minutes at room temperature. Beads were then washed 2× in 20 mM Tris (7.5). PABPC1-GST and SNRPA1-GST proteins were expressed using high-yield human intro translation lysate. Lysates were diluted 1:10 in binding buffer before use. For the binding reaction, proteins were incubated with RNA-containing beads (both positive and negative controls), or base beads in 1× binding buffer (PABPC1-10 mM Tris (7.5), 2.5 mM $MgCl_2$, 10 mM KCl, 15% glycerol, 0.5% Tween-20, 10 μg tRNA; SNRPA1-10 mM Tris (7.5), 250 mM NaCl, 1 mM EDTA, 0.5% Tween-20, and 10 μg tRNA) for one hour at 4° C. Beads were washed 3× in 20 mM Tris (7.5), 10 mM NaCl, 0.5% Tween-20. Complexes were eluted using 2× reducing sample buffer. Normalized samples were separated by electrophoresis, transferred, and detected using PABPC1, GST (SNRPA1) antibodies (1:1000 dilution in TBST-0.5% BSA). Exposure time-1 minute. FT—flow-through; 1,2,3—washes, E-elution. RNA used for pull-downs are labeled above respective blots. Lane 1—flow-through (40 μl), Lanes 2-4—washes (40 μl), Lane 5—Elution (20 μl). Similarly, U1A RNA was labeled, and a GST-tagged SNRPA1 was overexpressed in the IVT system. The RNA-bound beads were incubated with the 2-3 μl of the IVT lysate in binding buffer (10 mM Tris-HCl, pH 7.5, 250 mM NaCl, 0.5% Tween-20, 1 mM EDTA, and 10 μg of tRNA) for one hour at 4° C. The results are shown in FIG. 16. RNA used for pull-downs are labeled above respective blots. Lane 1—flow-through (40 μl), Lanes 2-4—washes (40 μl), Lane 5—Elution (20 μl).

EXAMPLE 5

In one embodiment, biotin or another suitable moiety containing a $PEG_{12}$ spacer, known by one skilled in the art, on the labeled nucleotide serves as an affinity handle for isolating RNA:protein complexes. The functionality of a described biotin-labeled RNA to serve as an affinity handle for isolating RNA complexes (containing RNA, DNA, RNA and DNA, or protein) using an affinity resin, was determined using streptavidin magnetic beads. In this embodiment, the protein was crosslinked to the RNA for enrichment.

Poly(A)$_{25}$ RNA was labeled using biotin-$PEG_{12}$-alkane-3'5'-bisphosphate cytidine and T4 RNA ligase. The Poly(A) Binding Protein (PABP), which binds the poly(A) tracts of mRNA, was cloned into a vector containing a GST-tag and expressed in a human cell-free in vitro translation (IVT) system. The lysate was diluted 1:10 for use in the binding reaction. The labeled RNA (50 pmol) was incubated with streptavidin magnetic beads (0.5 mg) for thirty minutes in 20 mM Tris-HCl (7.5), 100 mM NaCl, 1 mM EDTA. After washing, the beads were then incubated with 2-3 μl of diluted IVT lysate cell lysate in Binding Buffer (10 mM Tris-HCl, pH 7.5, 2.5 mM $MgCl_2$, 10 mM KCl, 15% glycerol, 0.5% Tween-20, and 10 μg tRNA) for one hour at 4° C. An unrelated RNA was used as a negative control, and beads were incubated with lysate alone to assess background. After a gentle wash, the binding reaction was crosslinked on ice using UV light. Beads were washed in 20 mM Tris-HCl (7.5), 10 mM NaCl, 0.5% Tween-20, and protein was eluted by heating at 95° C. for five to ten minutes using 1× reducing sample buffer, or eluting with 4 mM biotin in 20 mM Tris (7.5). After separation by electrophoresis, PABP was detected using GST antibody.

The results are shown in FIG. 17. Methods are described for FIG. 16 except that after a gentle wash after the binding reaction, RNA-protein complexes were crosslinked for ten minutes on ice. Exposure time-30 seconds. FT-flow-through; 1,2,3-washes, E elution. RNA used for pull-downs are labeled above respective blots. Lane 1—flow-through (40 μl), Lanes 2-4—washes (40 μl), Lane 5—Elution (20 μl).

All citations are expressly incorporated by reference herein in their entirety, including those throughout the disclosure as well as the following:

Khanan et. Al. (2006) Poly(A)-Binding Protein Binds to A-Rich Sequences via RNA Binding Domains 1+2 and 3+4. RNA Biology. 3: 170-177.

Rimmele and Belasco. (1998) Target discrimination by RNA binding proteins: role of the ancillary protein U2A' and a critical leucine residue in differentiating the RNA-binding specificity of spliceosomal proteins U1A and U2B". RNA. 4: 1386-1396.

DNASU Plasmid Repository, Arizona State University Bio-Design Institute.

U.S. Patent Publication No. 2011/0262917.

England et al. Specific labeling of 3' termini of RNA with T4 RNA ligase (1980) *Methods Enzym.* 65: 65-74.

Brennan and Gumport. T4 RNA ligase catalyzed synthesis of base-analogue-containing oligodeoxyribonucleotides and a characterization of their thermal stabilities. (1985) *Nucleic Acids Res.* 13: 8665-8684.

Hinton et al. The preparative synthesis of oligodeoxyribonucleotides using RNA ligase. (1982) *Nucleic Acids Res.* 10:1877-1894.

Walker et al. T4-induced RNA ligase joins single-stranded oligoribonucleotides (1975) *PNAS* 72: 122-126.

Richardson and Gumport. Biotin and fluorescent labeling of RNA using T4 RNA ligase. (1983) *Nucleic Acids Res.* 11: 6167-6184.

England et al. Dinucleoside pyrophosphates are substrates for T4-induced RNA ligase (1977) *PNAS* 74: 4839-4842.

Keith. Optimization of conditions for labeling the 3' OH end of tRNA using T4 RNA ligase. (1983) *Biochimie* 65: 367-70.

Romaniuk et al. Joining of RNA molecules with RNA ligase (1983) *Methods Enzym* 100: 52-59.

Romaniuk et al. The effect of acceptor ribonucleotide sequence for the T4 RNA ligase reaction. (1982) *European J of Biochem.* 125: 639-643.

Park et al. Useful tools for biomolecule isolation, detection, and identification: acylhydrazone-based cleavable linkers. (2009) *Chemistry & Biology* 16: 763-772.

Shigdel et al. Diazirine-based DNA photo-cross-linking probes for the study of protein-DNA interactions (2008) *Angew. Chem. Int.* 47: 90-93.

Costas et al. RNA-protein crosslinking to AMP residues at internal positions in RNA with a new photocrosslinking ATP analog (2000) *Nucl. Acids. Res.* 28: 1849-1858.

Gomes and Gozzo (2010). Chemical cross-linking with a diazirine photoactivatable cross-linker investigated by MALDI- and ESI-MS/MS. *J. Mass. Spectrom.* 45:892-9.

Liu and Sun. Direct isolation of specific RNA-interacting proteins using a novel affinity medium. (2005) *Nucl. Acids Res.* 33: 1-5.

Bachler et al. StreptoTag: A novel method for the isolation of RNA-binding proteins. (1999). *RNA* 5: 1509-1516.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims.

What is claimed is:

1. A method for labeling a nucleic acid with a modified nucleotide, the method comprising contacting a sample containing the nucleic acid with the modified nucleotide to form a mixture;

adding a ligase to form a reaction mixture; and incubating the reaction mixture under conditions sufficient for the ligase to ligate the modified nucleotide to the nucleic acid, to result in a labeled nucleic acid;

where the modified nucleotide has the structure (II):

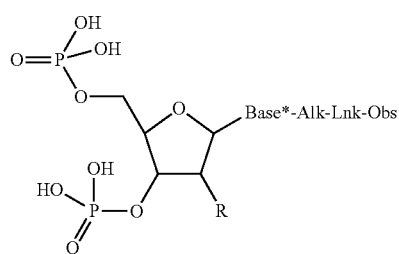

(II)

or a salt, conjugate base, tautomer, or ionized form thereof, where

Base* is a purine or pyrimidine base;

R is H, OH, $CH_3$, or a hydroxyl protecting group;

Alk is a connecting group having the structure -//—$(CH_2)_m$—Y—//- wherein m is an integer ranging from 3 to 6 inclusive, Y is a bond forming group selected from

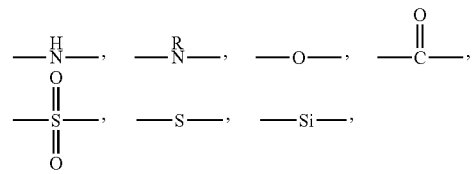

and the leftmost bond is to Base* and the rightmost bond is to Lnk;

Lnk is a linking group having the structure

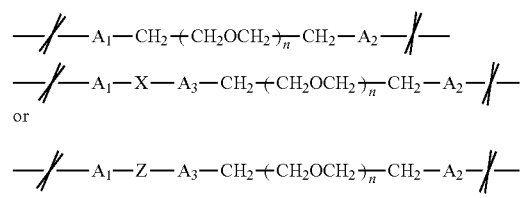

where n is an integer ranging from 2 to 48 inclusive, $A_1$ is a bond forming group selected from

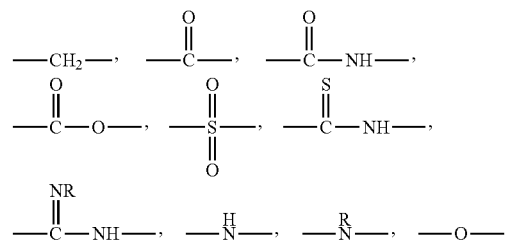

$A_2$ is a bond forming group selected from

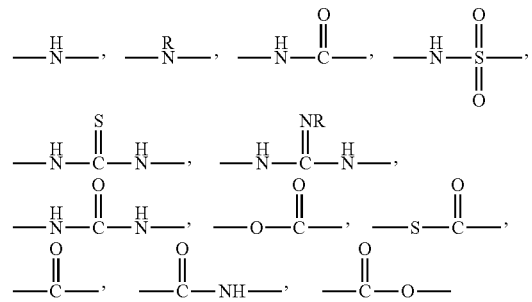

$A_3$ is a bond forming group selected from

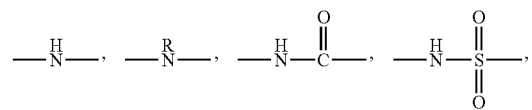

-continued

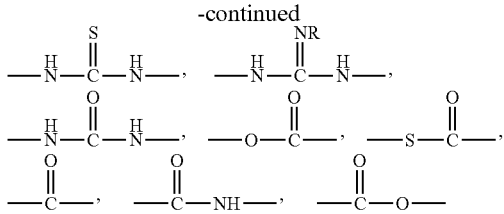

and X is a cleavable group that can undergo silicon-carbon cleavage, nucleophilic cleavage, redox cleavage, photochemical cleavage, enzymatic cleavage, or exchange-based cleavage; Z is a branching group that contains a modifying molecule (Mod); and the leftmost bond is to Alk and the rightmost bond is to Obs; and Obs is an observable label moiety.

2. The method of claim 1, the modified nucleotide wherein the sugar is ribose, and the purine or pyrimidine base is selected from cytosine (C), uracil (U), adenine (A), guanine (G), or inosine (I).

3. The method of claim 2, where the purine or pyridine base is selected from 1-methyladenine, $N^6$-methyladenine, $N^6$-isopentyladenine, N,N-dimethyladenine, 7-deazaadenine, 2-thiocytosine, 3-methylcytosine, $N^4$-acetylcytosine, 2-thiocytosine, 1-methylguanine, 2-methylguanine, 7-methylguanine, $N_2,N_2$-dimethylguanine, 7-deazaguanine, 2-thiouracil, 6-thiopurine, or 2,6-diaminopurine.

4. The method of claim 1, the modified nucleotide wherein the observable label is a chromogen, a fluorophore, a mass label, a spin label, a streptavidin-binding label, or a secondary detection label.

5. The method of claim 1, the modified nucleotide wherein n is an integer selected from 2 to 24 inclusive.

6. The method of claim 1, the modified nucleotide wherein the sugar is ribose; the purine or pyrimidine base is selected from adenine (A), cytosine (C), guanine (G), uracil U), or inosine (I); m is 3; n is 4; and the observable label is a streptavidin-binding compound selected from biotin, desthiobiotin, or iminobiotin.

7. The method of claim 1, the modified nucleotide wherein the sugar is ribose; the purine or pyrimidine base is cytosine (C); m is 3; Lnk is

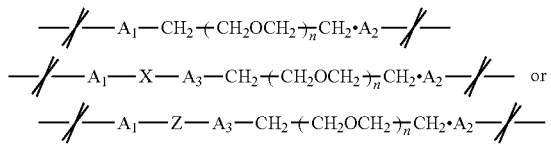

where
n is 4, $A_1$ is

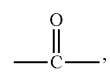

$A_2$ is

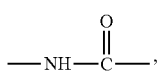

and when present, $A_3$ is

and

Z is a branching group that contains a modifying molecule (Mod), and Obs is selected from the group consisting of biotin, a fluorophore, and an azide.

8. The method of claim 1, wherein the ligase is T4 ligase.

9. The method of claim 8, wherein the ligase is selected from the group consisting of single stranded T4 ligase, double stranded T4 ligase, thermostable T4 ligase, T4 RNA Ligase 1, T4 RNA Ligase 2, T4 RNA Ligase 2, truncated, and T4 RNA Ligase 2, truncated K227Q.

10. The method of claim 1 wherein prior to the contacting step, the sample containing the nucleic acid is heated to a temperature of about 75° C. to about 95° C., and then cooled to a temperature of about 2° C. to about 10° C., wherein the sample optionally contains dimethylsulfoxide (DMSO) at a concentration ranging from 0% to about 25%.

11. The method of claim 1, wherein the reaction mixture further comprises PEG having a molecular weight between about 1500 and 24,000 inclusive and at a concentration ranging from $5\%^{w/v}$ PEG to $20\%^{w/v}$ PEG inclusive.

12. The method of claim 1, wherein the conditions sufficient for the ligase to ligate the modified nucleotide to the nucleic acid comprise incubating the reaction mixture between 30 minutes and 16 hours at a temperature ranging between 16° C. and 37° C.

13. The method of claim 1, wherein the nucleic acid is RNA.

14. A method for detecting a nucleic acid binding biomolecule, the method comprising forming a labeled nucleic acid by
labeling a nucleic acid with a modified nucleotide, the method comprising contacting a sample containing the nucleic acid with the modified nucleotide to form a mixture;
adding a ligase to form a reaction mixture; and
incubating the reaction mixture under conditions sufficient for the ligase to ligate the modified nucleotide to the nucleic acid, to result in a labeled nucleic acid;
incubating the labeled nucleic acid with a biological sample thought to contain the nucleic acid binding biomolecule to form a complex; and
detecting the complex of the nucleic acid binding biomolecule bound to the labeled nucleic acid;
where the modified nucleotide has the structure (II):

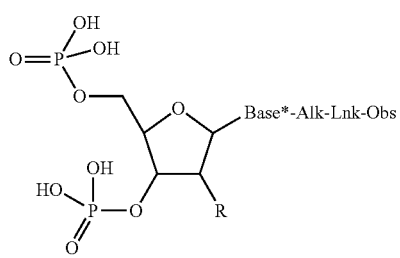

(II)

or a salt, conjugate base, tautomer, or ionized form thereof, where

Base* is a purine or pyrimidine base;

R is H, OH, CH$_3$, or a hydroxyl protecting group;

Alk is a connecting group having the structure -//—(CH$_2$)$_m$—Y—//- wherein m is an integer ranging from 3 to 6 inclusive, Y is a bond forming group selected from

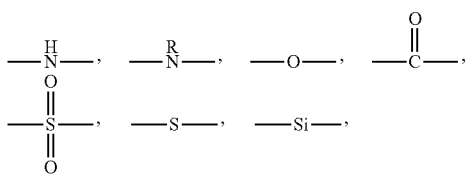

and the leftmost bond is to Base* and the rightmost bond is to Lnk;

Lnk is a linking group having the structure

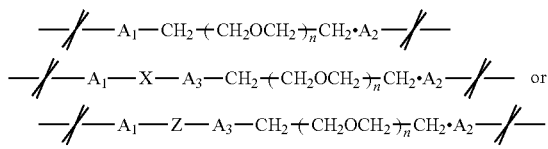

where n is an integer ranging from 2 to 48 inclusive, A$_1$ is a bond forming group selected from

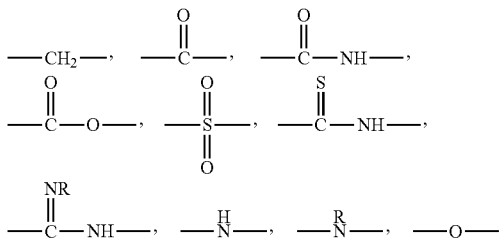

A$_2$ is a bond forming group selected from

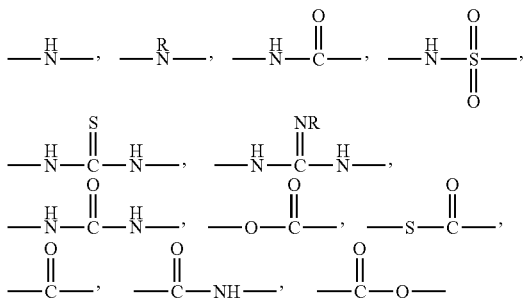

A$_3$ is a bond forming group selected from

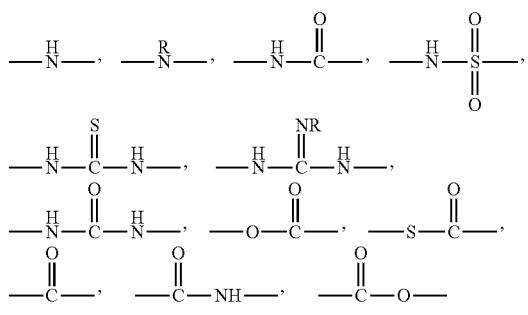

and X is a cleavable group that can undergo silicon-carbon cleavage, nucleophilic cleavage, redox cleavage, photochemical cleavage, enzymatic cleavage, or exchange-based cleavage; Z is a branching group that contains a modifying molecule (Mod); and the leftmost bond is to Alk and the rightmost bond is to Obs; and Obs is an observable label moiety.

15. The method of claim 14, wherein the biological sample is a purified protein, a tissue sample, whole tissue, whole organ, cell culture, cell extract, cell lysate, or in vitro translated protein lysate.

16. The method of claim 14, wherein the labeled nucleic acid is RNA and the nucleic acid binding biomolecule is an RNA-binding protein.

17. The method of claim 16, wherein the complex of the labeled RNA and the RNA-binding protein is stabilized by crosslinking the RNA-binding protein to the labeled RNA by the modifying molecule of the modified nucleotide or by adding crosslinkers after the labeled RNA/RNA-binding protein complex is formed.

18. The method of claim 14, wherein detection of the complex comprises associating the complex with a solid support, eluting the complex from the solid support, and detecting the eluted complex.

19. The method of claim 18, wherein the solid support is a bead, a plate, or a column.

20. The method of claim 18, wherein the Obs of the modified nucleotide is biotin, desthiobiotin or iminobiotin and the solid support comprises a streptavidin.

21. The method of claim 14, wherein detection comprises a mobility shift assay comprising subjecting the complex to electrophoresis and detecting a shift in molecular weight of the complex compared to the nuclei acid binding biomolecule alone.

22. The method of claim 14, wherein detection comprises subjecting the biological sample to electrophoresis, transferring the electrophoresed biological sample to a membrane, probing the membrane with the labeled nucleic acid, and detecting the complex.

23. The method claim 14, wherein detection comprises in situ hybridization.

* * * * *